United States Patent
Seredenin et al.

(10) Patent No.: US 9,683,014 B2
(45) Date of Patent: Jun. 20, 2017

(54) DIPEPTIDE MIMETICS OF NGF AND BDNF NEUROTROPHINS

(71) Applicant: UCHREZHDENIE ROSSIISKOI AKADEMII MEDITSYNSKIKH NAUK NAUCHNO-ISSLEDOVATELSKY INSTITUT FARMAKOLOGII IMENI V.V.ZAKUSOVA RAMN, Moscow (RU)

(72) Inventors: Sergey Borisovich Seredenin, Moscow (RU); Alexandrovna Tatyana Gudasheva, Moscow (RU)

(73) Assignee: UCHREZHDENIE ROSSIISKOI AKADEMII MEDITSYNSKIKH NAUK NAUCHNO-ISSLEDOVATELSKY INSTITUT FARMAKOLOGII IMENI V.V.ZAKUSOVA RAMN, Moscow (RU)

(*) Notice: Subject to any disclaimer, the term of this patent is extended or adjusted under 35 U.S.C. 154(b) by 0 days.

(21) Appl. No.: 14/460,881

(22) Filed: Aug. 15, 2014

(65) Prior Publication Data
US 2015/0111828 A1    Apr. 23, 2015

Related U.S. Application Data

(62) Division of application No. 13/148,830, filed as application No. PCT/RU2010/000067 on Feb. 15, 2010, now abandoned.

(30) Foreign Application Priority Data

Feb. 16, 2009 (RU) ................. 2009105176

(51) Int. Cl.
| | |
|---|---|
| *C07K 5/02* | (2006.01) |
| *C07K 5/06* | (2006.01) |
| *C07K 5/072* | (2006.01) |
| *C07K 5/062* | (2006.01) |
| *C07K 5/065* | (2006.01) |
| *C07K 5/068* | (2006.01) |
| *A61K 38/00* | (2006.01) |

(52) U.S. Cl.
CPC ........... *C07K 5/06104* (2013.01); *C07K 5/02* (2013.01); *C07K 5/06* (2013.01); *C07K 5/0606* (2013.01); *C07K 5/06026* (2013.01); *C07K 5/06069* (2013.01); *C07K 5/06078* (2013.01); *C07K 5/06086* (2013.01); *C07K 5/06113* (2013.01); *A61K 38/00* (2013.01)

(58) Field of Classification Search
None
See application file for complete search history.

(56) References Cited

U.S. PATENT DOCUMENTS

| | | |
|---|---|---|
| 5,958,875 A | 9/1999 | Longo et al. |
| 6,017,878 A | 1/2000 | Saragovi et al. |
| 2003/0130197 A1 | 7/2003 | Smith-Swintosky et al. |

FOREIGN PATENT DOCUMENTS

| | | | |
|---|---|---|---|
| EP | 0335637 A2 * | 10/1989 | ........... C07K 5/1019 |
| WO | 99/07814 A1 | 2/1999 | |
| WO | 00/75176 A1 | 12/2000 | |
| WO | 01/91780 A1 | 12/2001 | |
| WO | 2005/123770 A1 | 12/2005 | |

OTHER PUBLICATIONS

Saragovi, H. U., et al., "Small molecule and protein-based neurotrophic ligands: agonists and antagonists as therapeutic agents", Exp. Opin. Ther. Patents 1999, 9(6), pp. 737-751.
Schulte-Herbruggen, O., et al., Neurotrophic Factors a Tool for Therapeutic Strategies in Neurological, Neuropsychiatric and Neuroimmunological Diseases?, Current Medicinal Chemistry, 2007, 14(22), pp. 2318-2329.
Thoenen, H., et al., "Towards a comprehensive understanding of the trophic support of motoneurons", C. R. Acad. Sci., 1993, 316(9), pp. 1161-1163.
Spina, M. B., et al., "Brain-Derived Neurotrophic Factor Protects Dopamine Neurons Against 6-Hydroxydopamine and N-Methyl-4-Phenylpyridinium Ion Toxicity: Involvement of the Glutathione System", Journal of Neurochemistry, 1992, 59(1), pp. 99-106.
Lindsay, R.M., et al., Neurotrophic Growth Factors and Neurodegenerative Diseases: Therapeutic Potential of the Neurotrophins and .Ciliary Neurotrophic Factor, Neurobiology of Aging. 1994, 15(2), pp. 249-251.
Volonte, C., et al., "Association of a Purine-Analogue-Sensitive Protein Kinase Activity with p75 Nerve Growth Factor Receptors", Molecular Biology of the Cell, Jan. 1993, 4(1), pp. 71-78.
Barbacid, M., "The Trk Family of Neurotrophin Receptors", Journal of Neurobiology, 1994, 25(11), pp. 1386-1403.
(Continued)

*Primary Examiner* — Robert C Hayes
(74) *Attorney, Agent, or Firm* — Ladas & Parry LLP

(57) ABSTRACT

The invention relates to compounds having either agonist or antagonist activities for the neurotrophins NGF and BDNF and represented by monomeric or dimeric substituted dipeptides that are analogs of the exposed portions of loop 1 or loop 4 regions of these neurotrophins near or at a beta-turn of the respective loop. N-acylated substituents of these dipeptides are biostereoisomers of the amino acid residues preceding these dipeptide sequences in the neurotrophin primary structure. The dimeric structure is produced advantageously by using hexamethylenediamine to which dipeptides are attached via their carboxyl groups. The claimed compounds displayed neuroprotective and differentiation-inducing activities in cellular models and enhanced the amount of phosphorylated tyrosine kinase A and the heat shock proteins Hsp32 and Hsp70 in the concentration range of $10^{-9}$ to $10^{-5}$ M. They also displayed neuroprotective, anti-parkinsonian, anti-stroke, anti-ischemic, anti-depressant and anti-amnestic activities in animal models and were active in experimental models of Alzheimer's disease. These in vivo effects of the claimed compounds are displayed in the dose range of 0.01 to 10 mg/kg when administered intraperitoneally.

4 Claims, 16 Drawing Sheets

(56) References Cited

OTHER PUBLICATIONS

McDonald, N. Q., et al., "Crystallization and Characterization of the High Molecular Weight Form of Nerve Growth Factor (7 S NGF)", J. Mol. Biol. 1991, 219(4), pp. 595-601.
Robinson, R. C., et al., "Structure of the Brain-Derived Neurotrophic Factor/Neurotrophin 3 Heterodimer", Biochemistry 1995, 34(13), pp. 4139-4146.
Ibanez, C. F., et al., "An extended surface of binding to Trk tyrosine kinase receptors in NGF and BDNF allows the engineering of a multifunctional pan-neurotrophin", EMBO Journal, 1993, 12(6), pp. 2281-2293.
McDonald, N. Q., et al., "Structural Determinants of Neurotrophin Action", Journal of Biological Chemistry, 1995, 270(34), pp. 19669-19672.
Longo, F. M., "Synthetic NGF Peptide Derivatives Prevent Neuronal Death Via a p75 Receptor-Dependent Mechanism", Journal of Neuroscience Research 48, 1997, pp. 1017.
Bongioanni, P., et al., "Ciliary neurotrophic factor (CNTF) for amyotrophic lateral sclerosis or motor neuron disease (Review)", The Cochran Library, 2009, Issue 4, pp. 1-24.
Longo, F. M., et al., "The in vitro biological effect of nerve growth factor is inhibited by synthetic peptides", Cell Regul., vol. 1, Jan. 1990, pp. 189-195.

\* cited by examiner

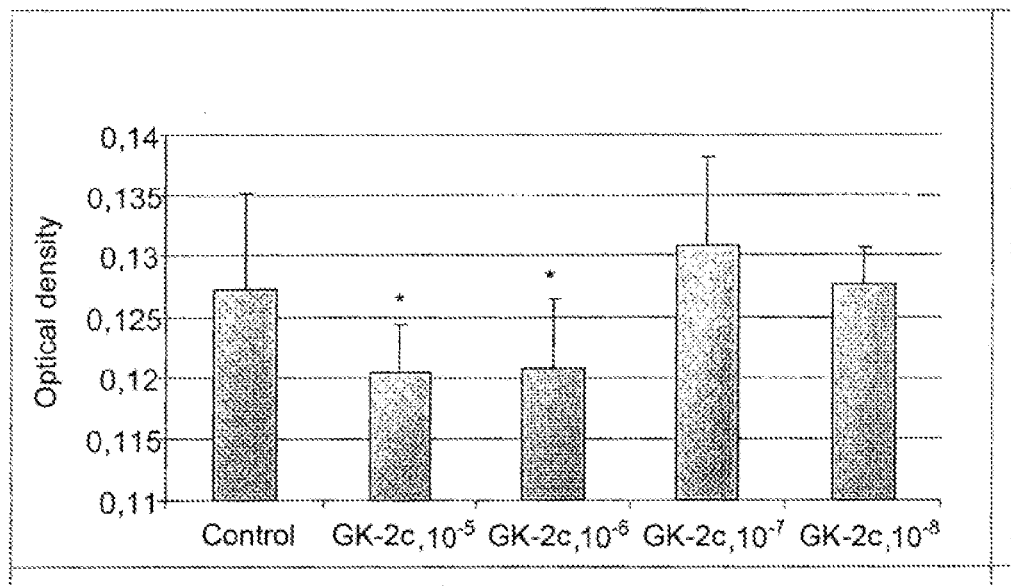
Fig. 1.1
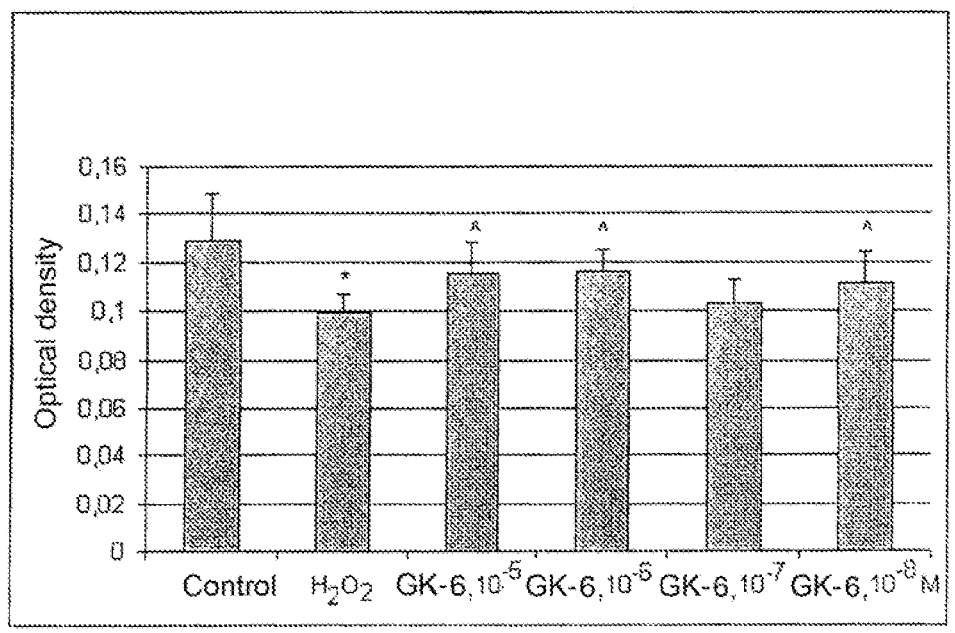
Fig. 1.2

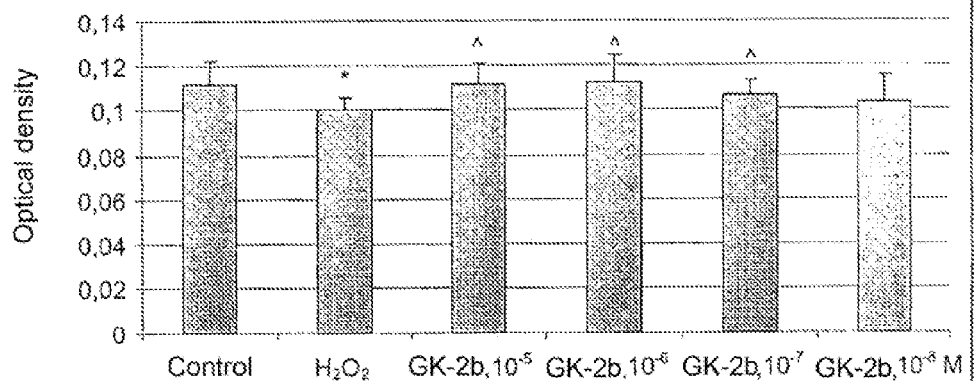
Fig. 1.3
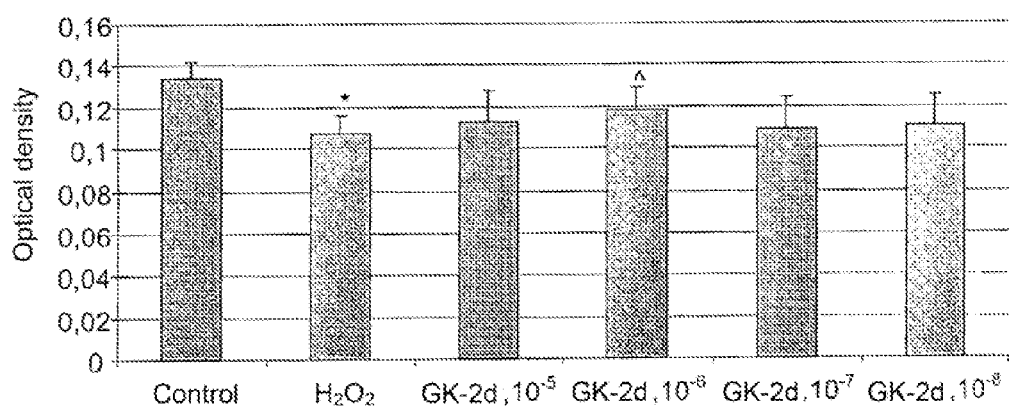
Fig. 1.4

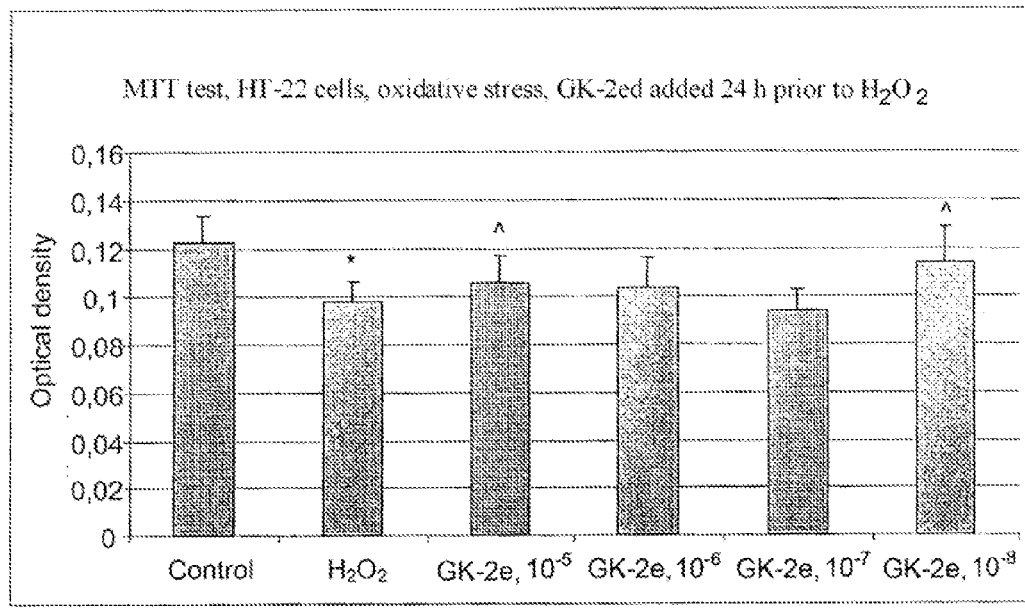
Fig. 1.5
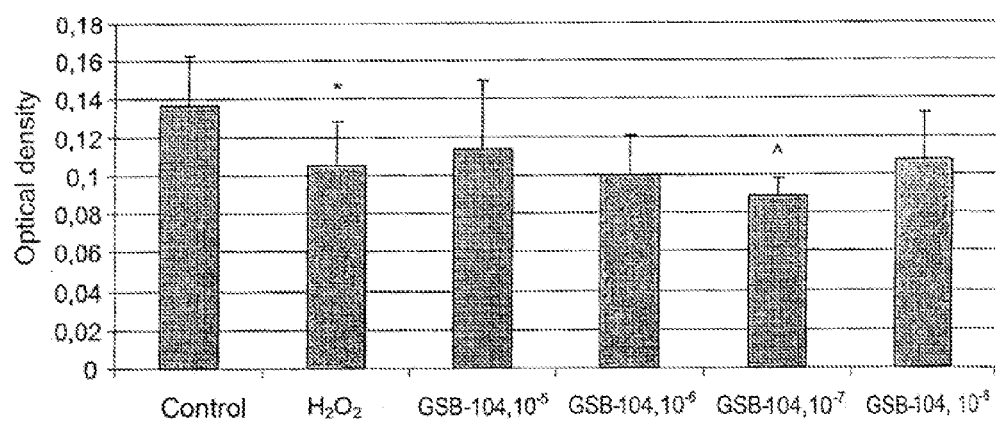
Fig. 1.6

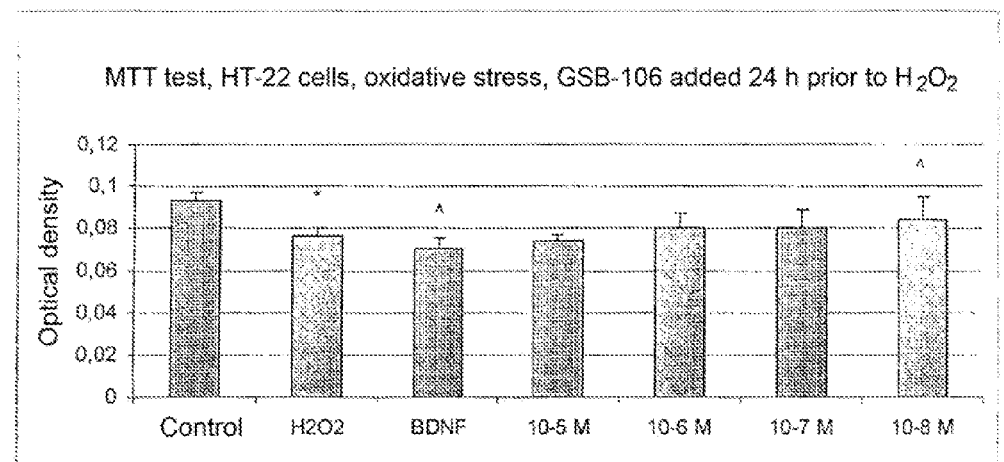
Fig. 1.7
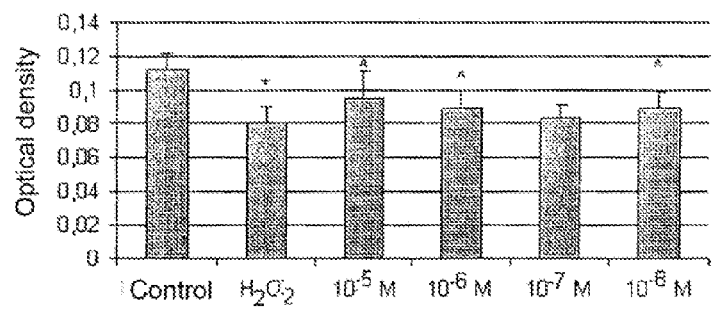
Fig. 1.8
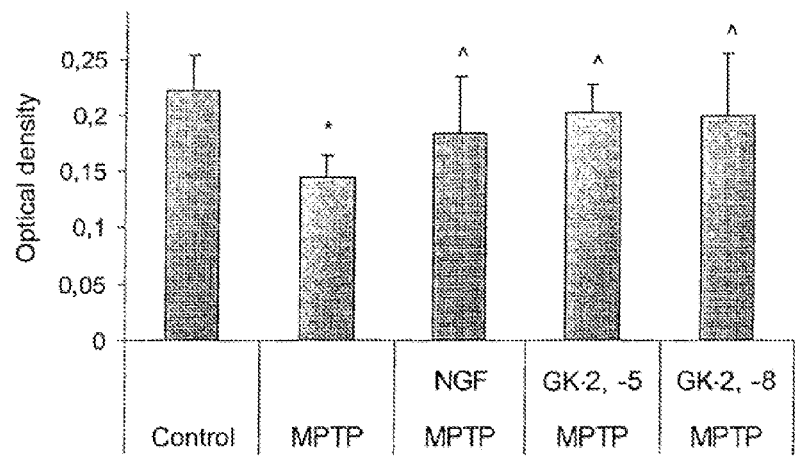
Fig. 1.9

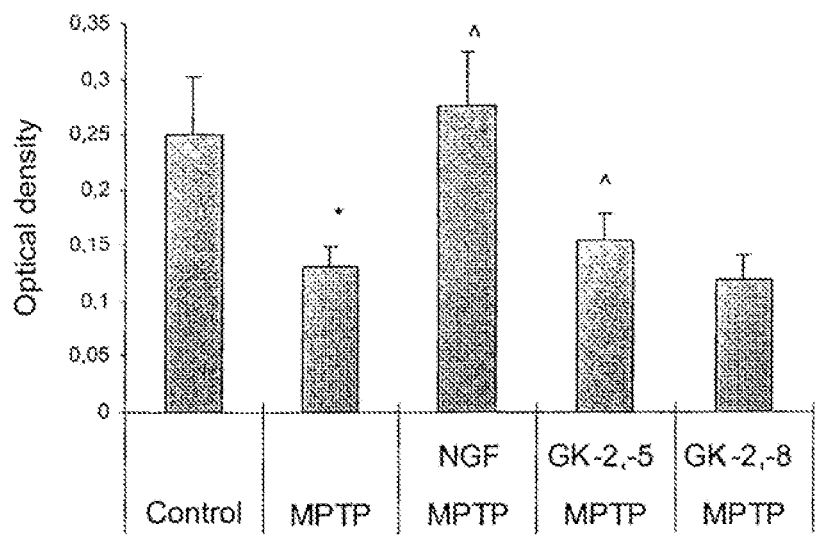
Fig. 1.10
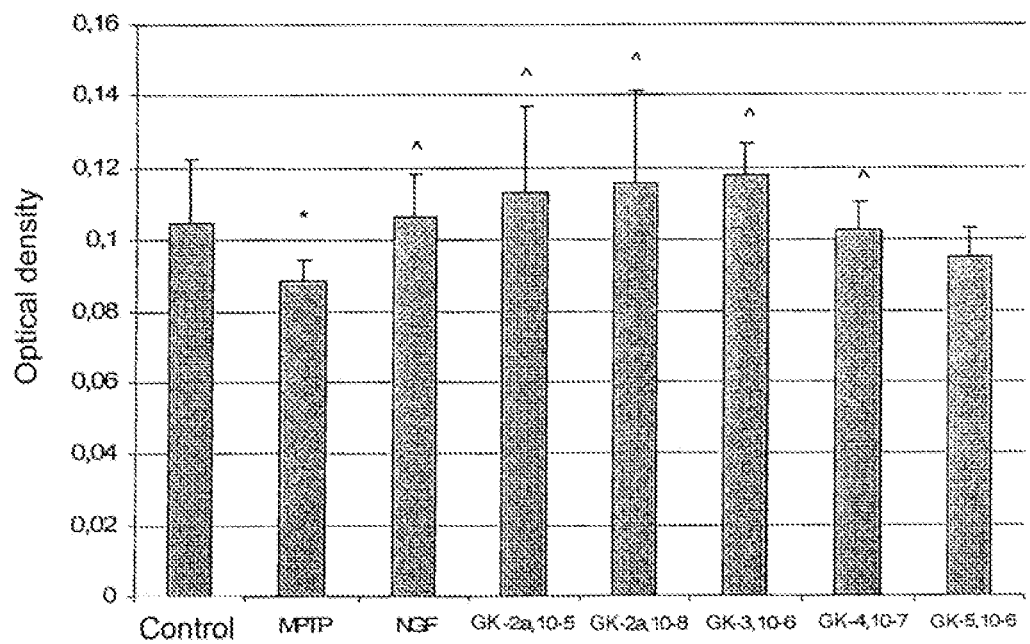
Fig. 1.11

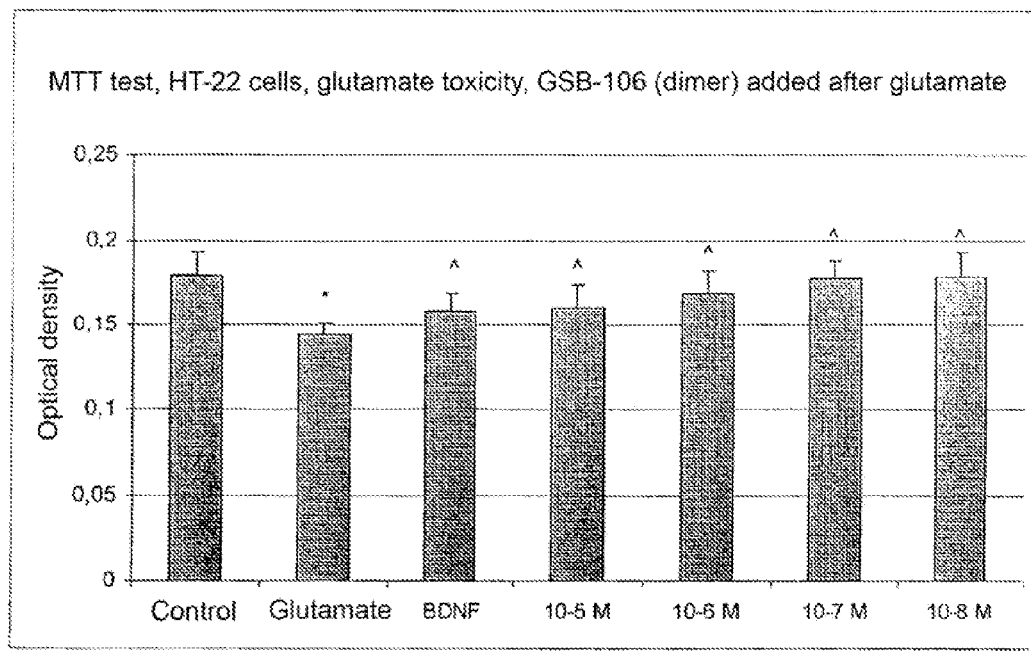
Fig. 1.12
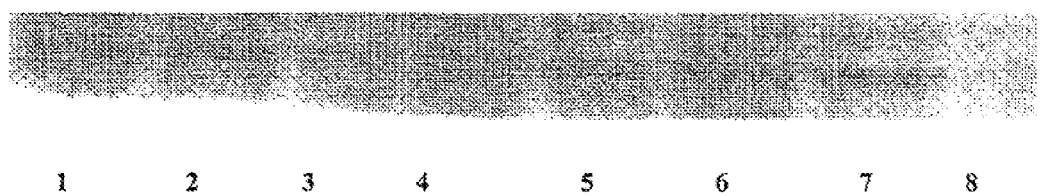
Fig. 1.13

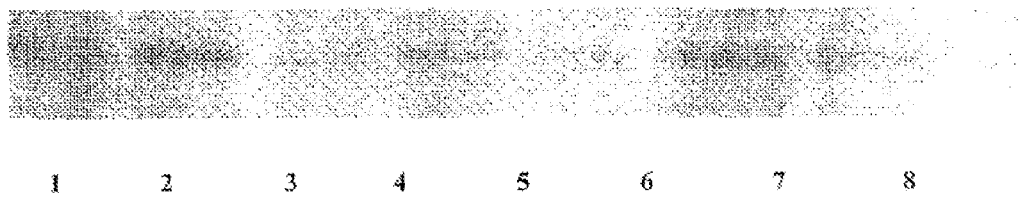
Fig. 1.14
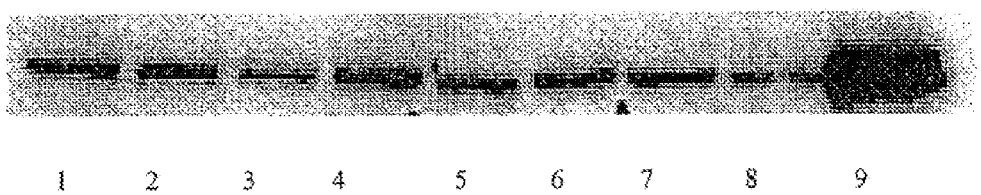
Fig. 1.15
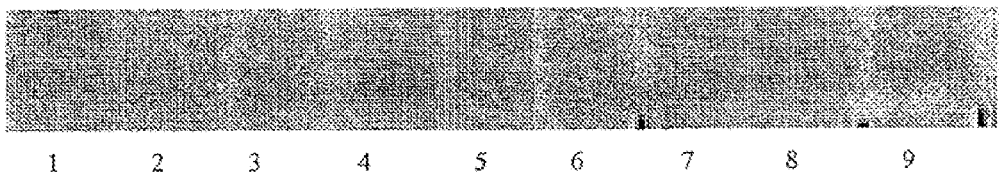
Fig. 1.16

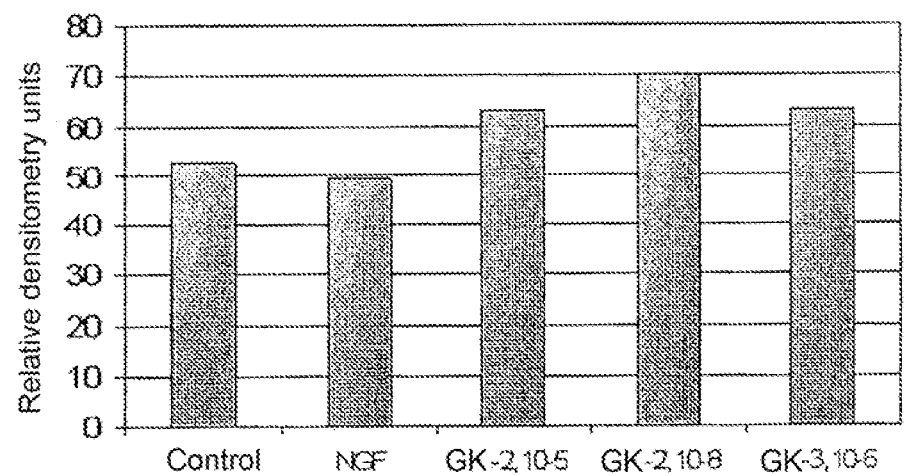
Fig. 1.17
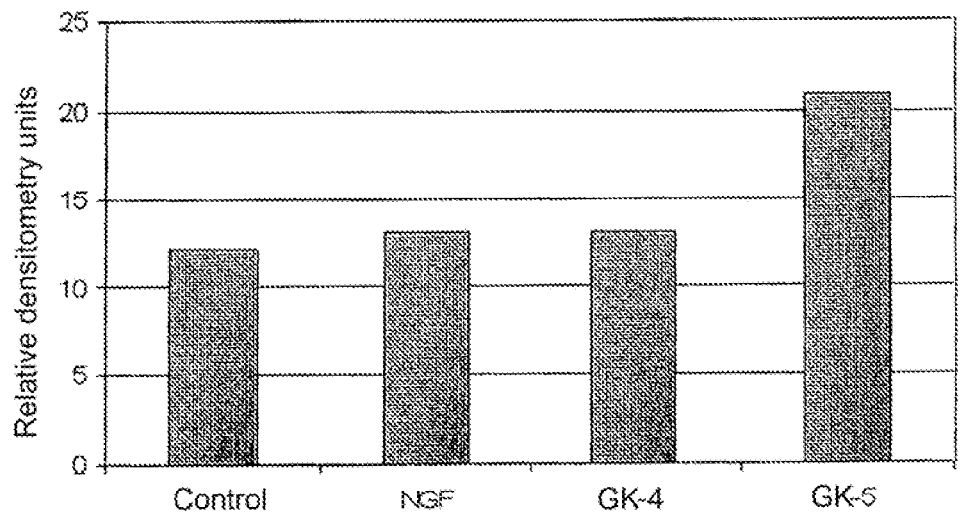
Fig. 1.18

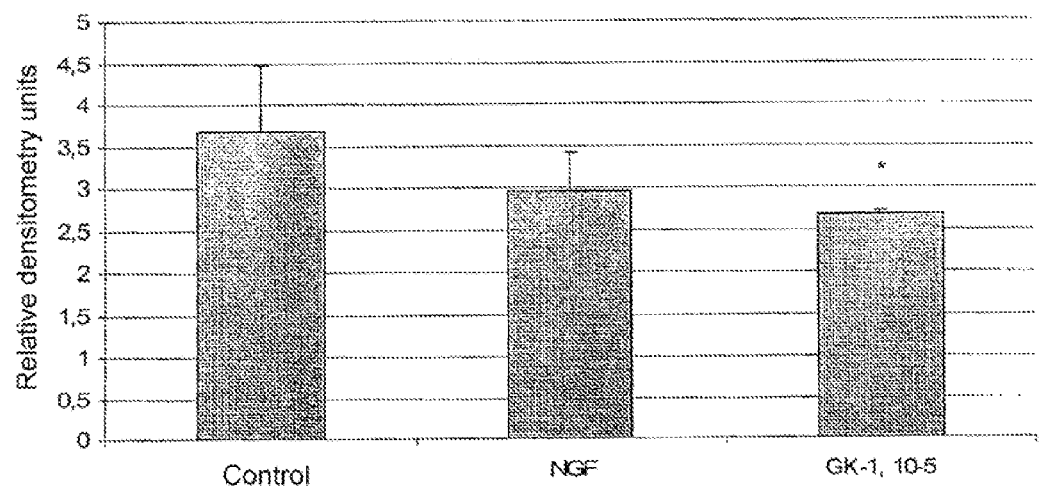
Fig. 1.19
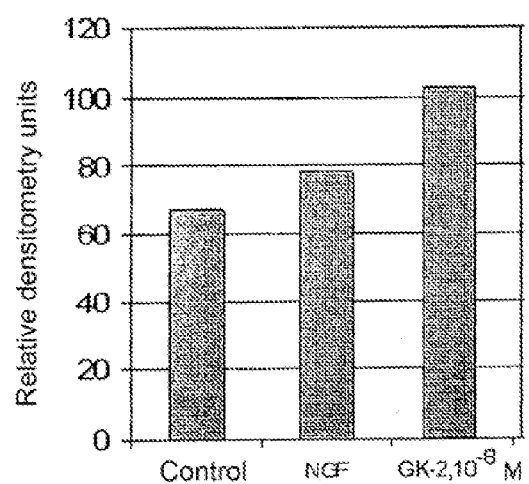
Fig. 1.20

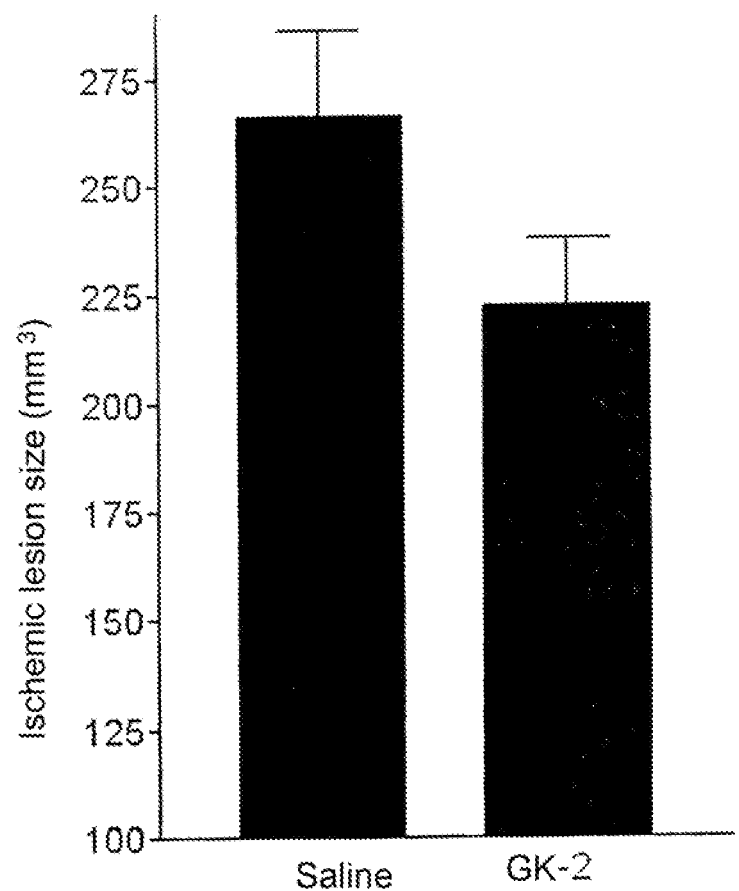
Fig. 2.1

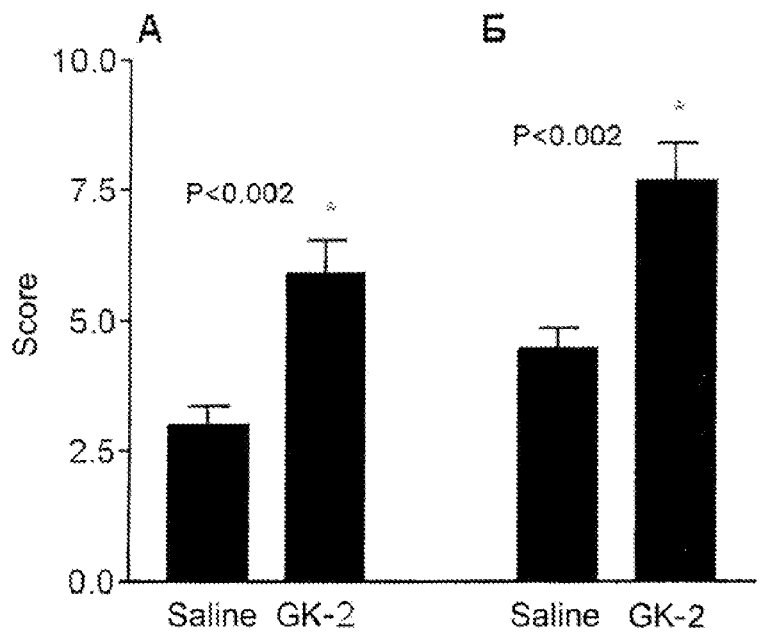
Fig. 2.2
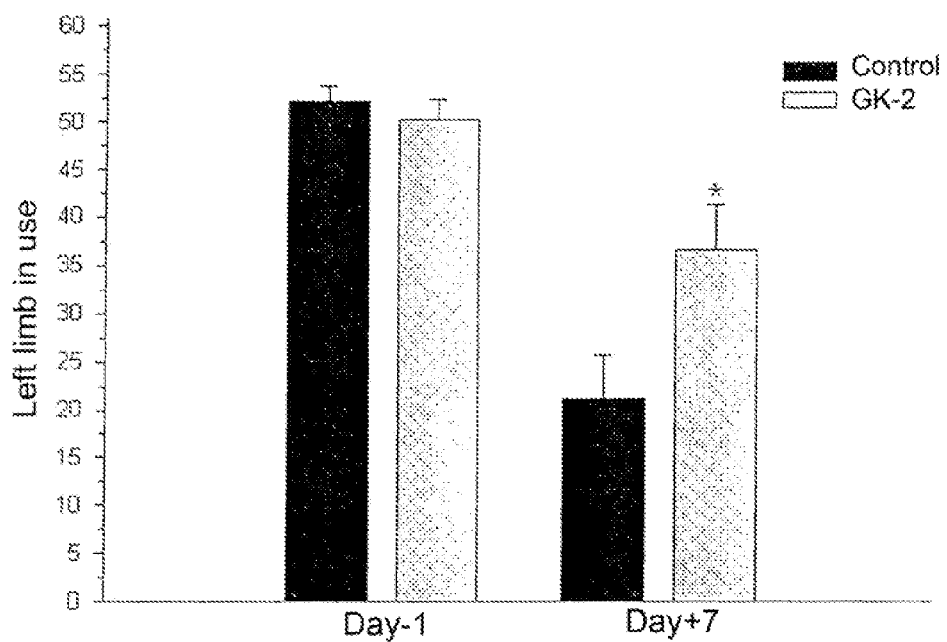
Fig. 2.3

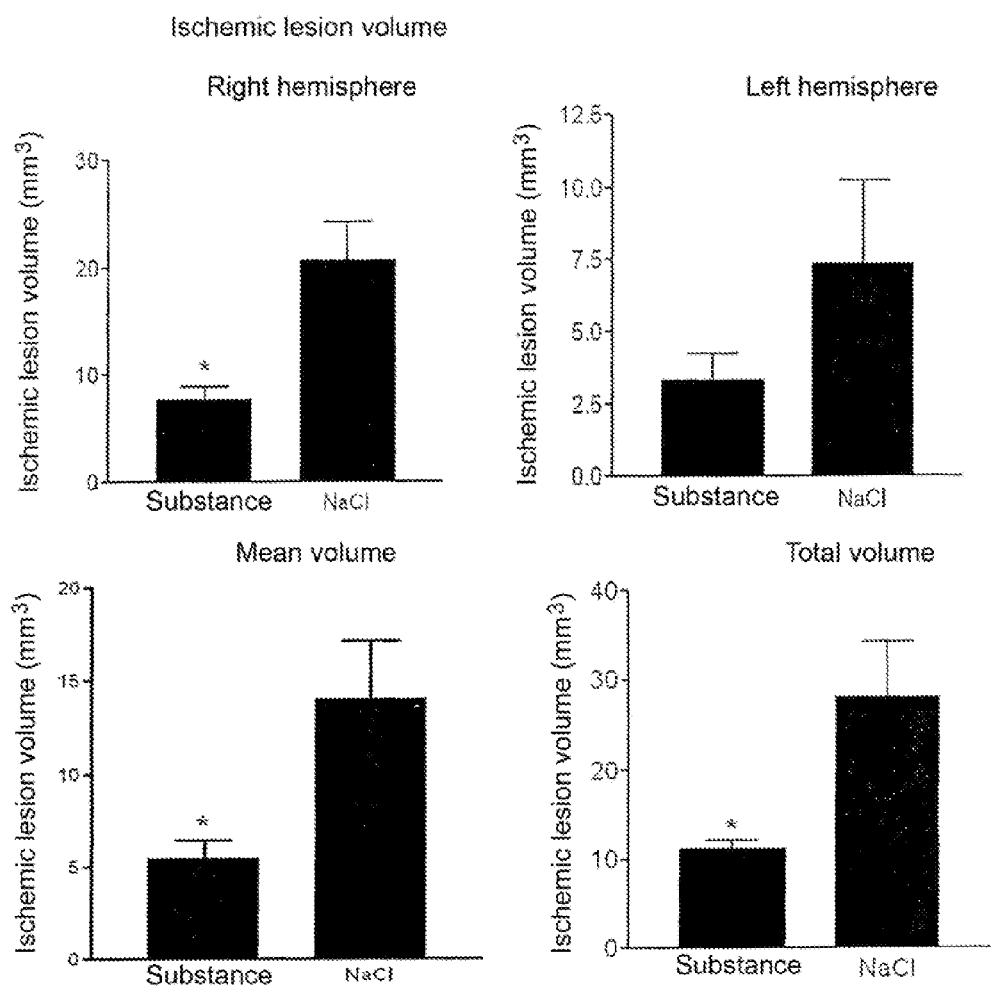
Fig. 2.4

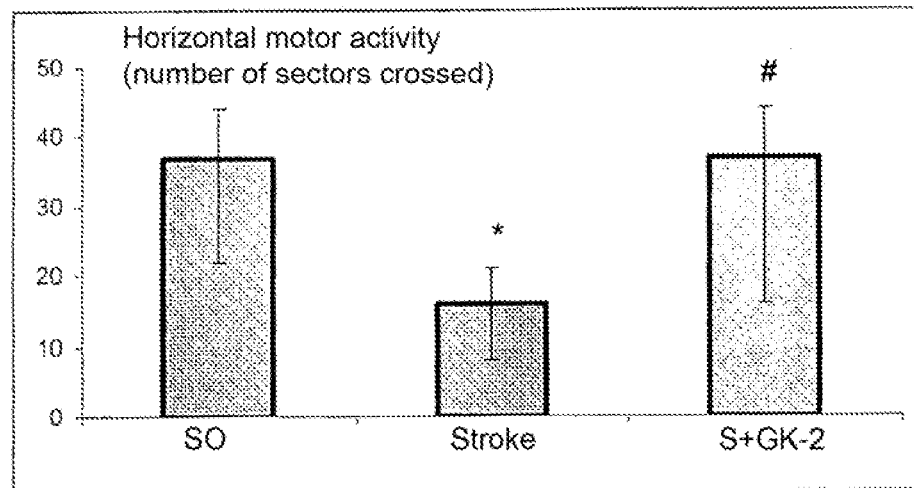
Fig. 2.5
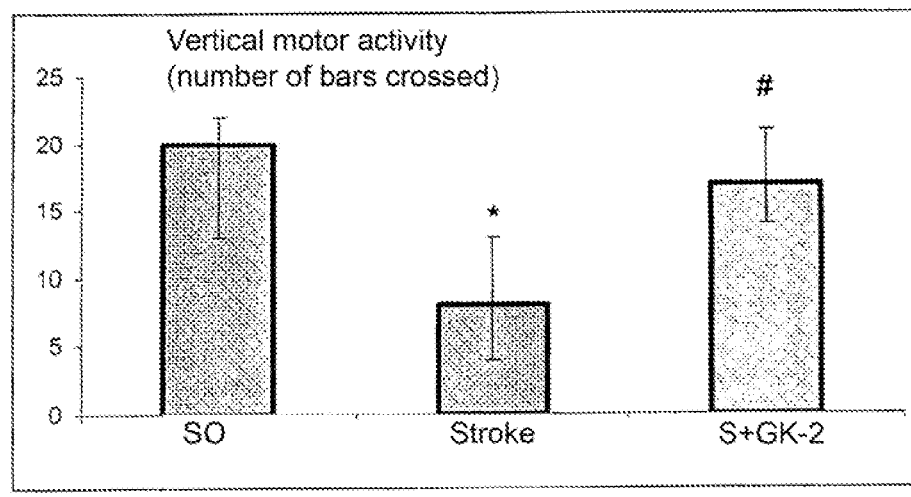
Fig. 2.6

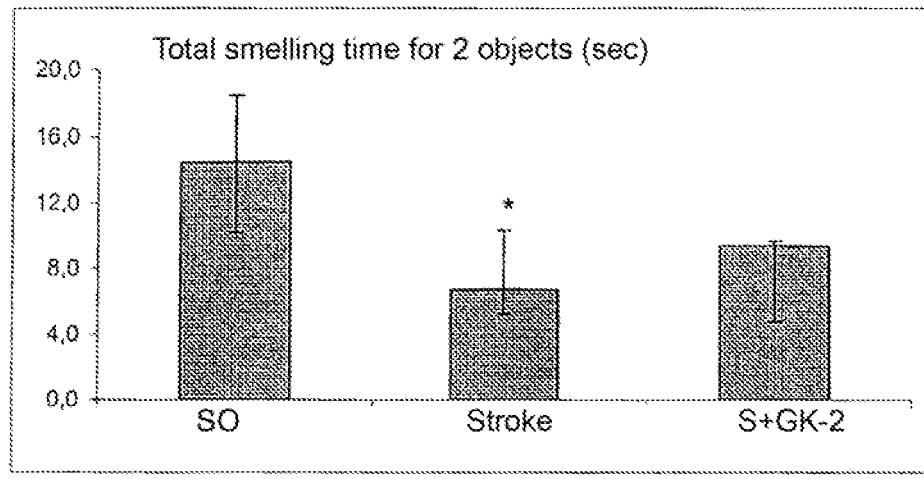
Fig. 2.7
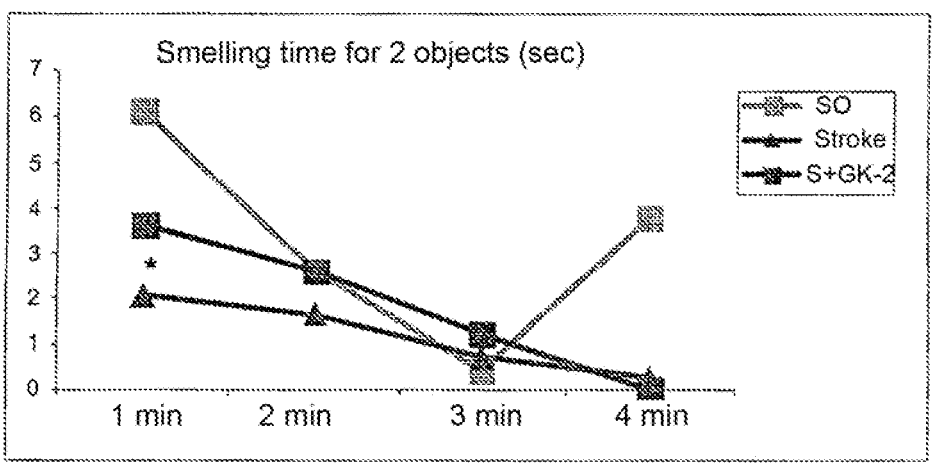
Fig. 2.8

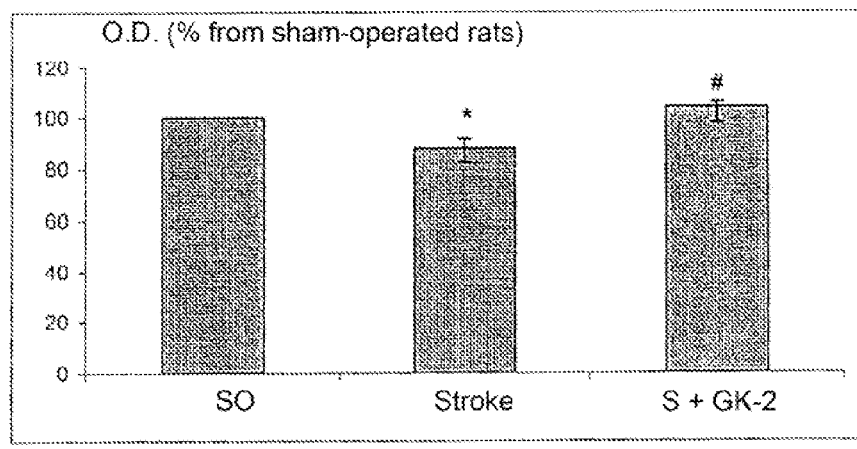
Fig. 2.9
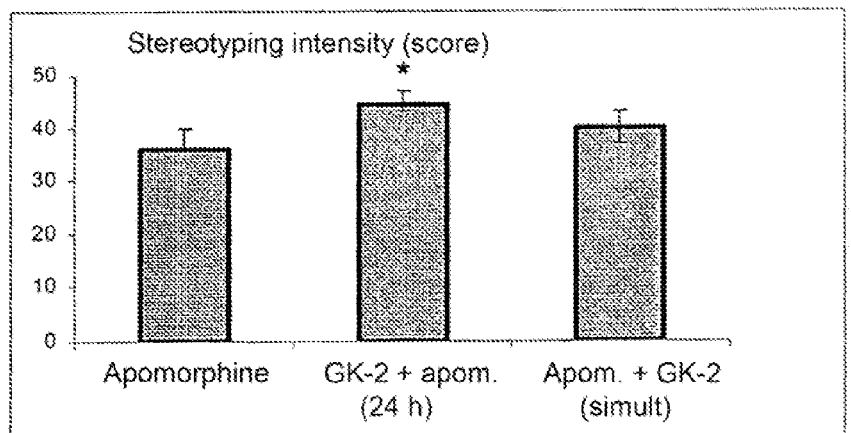
Fig. 2.10
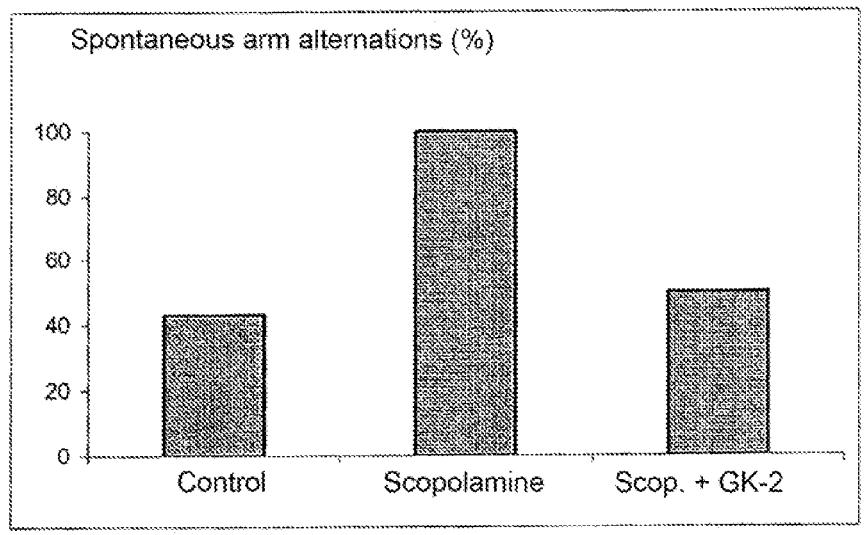
Fig. 2.11

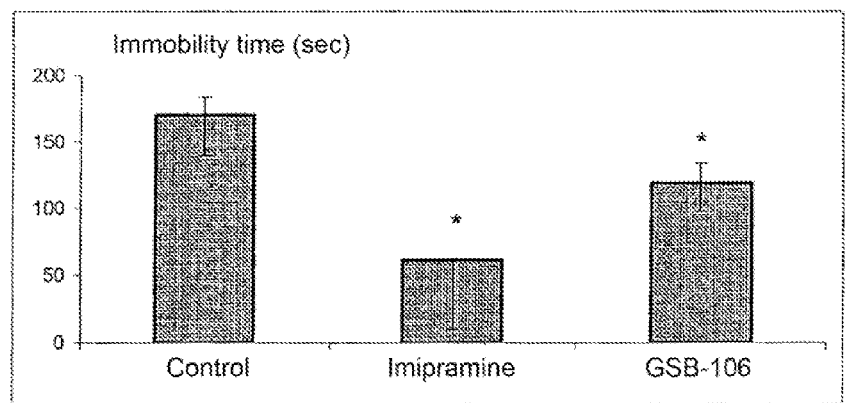
Fig. 2.12
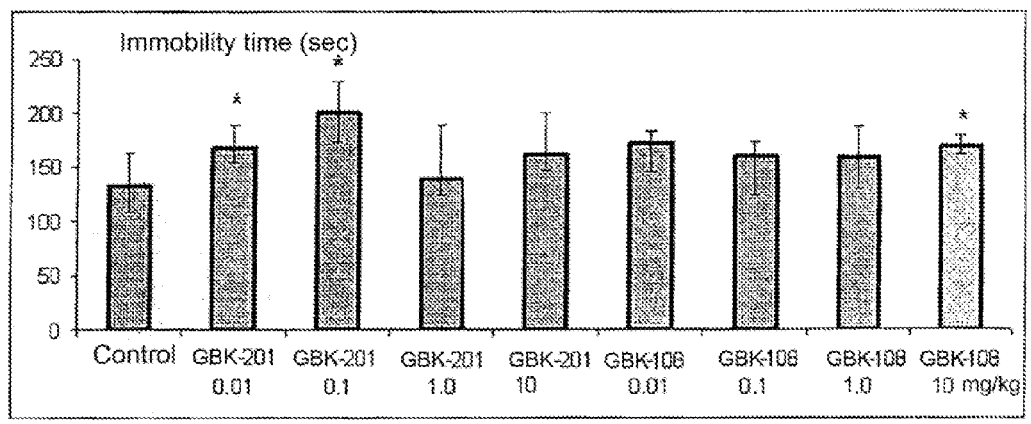
Fig. 2.13

DIPEPTIDE MIMETICS OF NGF AND BDNF NEUROTROPHINS

RELATED APPLICATION

This application is a Divisional of U.S. patent application Ser. No. 13/148,830, filed on Aug. 10, 2011, which is the national phase entry under 35 USC 371 of International Patent Application No. PCT/RU2010/000067, filed on Feb. 15, 2010, which claims priority from Russian Patent Application No. 2009105176 filed on Feb. 16, 2009, the entire contents of which are incorporated herein by reference.

FIELD OF THE INVENTION

The invention relates to the field of bioorganic chemistry, namely to novel substituted dipeptides that are mimetics of the neurotrophic factors, which can be useful as pharmaceutical agents for the regulation of growth, differentiation, survival and programmed neuronal cell death. More specifically, this invention relates to monomeric and dimeric dipeptide mimetics of the NGF and BDNF loop regions, which can be useful for the treatment of neurodegenerative diseases including Parkinson's and Alzheimer's diseases, Huntington's chorea, stroke, cerebral ischemia, cerebral traumas, depression etc.

BACKGROUND OF THE INVENTION

Nerve growth factor (NGF) and brain-derived neurotrophic factor (BDNF) are members of the neurotrophin family which can improve neuronal survival and prevent neurodegeneration resulting from disease or trauma. Sensory, sympathetic and cholinergic neurons are sensitive to NGF. Therapy using NGF is assumed to prevent the development of Alzheimer's disease, to prevent the loss of brain function in stroke and to improve the patient's quality of life in peripheral diabetic neuropathy. In addition, NGF is suggested to be useful for the treatment of neuronal damage and as a targeting agent for neuroectodermal tumors. For reviews on the use of NGF in therapy, see Saragovi H. U. and Burgess K., Expert Opinion in Therapeutic Patents 1999, 9:737-751; Schulte-Herbruggen O. et al., Curr. Med. Chem. 2007, 14(22): 2318-2329.

In the CNS, BDNF acts as a potent trophic factor for cerebral and spinal motor neurons that degenerate in amyotrophic lateral sclerosis (Thoenen H. et al., C. R. Acad. Sci. III, 1993, 316(9): 1158-63), and for dopaminergic neurons of substantia nigra that are lost in Parkinson's disease (Spina M. B. et al., J. Neurochem. 1992, 59(1):99-106). In the periphery, BDNF has a neurotrophic activity for small fibrous neurons involved in a number of sensory neuropaties (Lindsay R. M., Neurobiol. Aging. 1994, 15(2):249-251).

The biological effects of NGF, BDNF and other neurotrophins are mediated by the binding to cellular receptors of two classes: high affinity ($K_d$ of $10^{-11}$) receptors of the tyrosine kinase family and a low affinity ($K_d$ of $10^{-9}$) p75 receptor. The p75 receptor is a glycoprotein with a molecular weight of 75 kDa. It has no intrinsic catalytic activity, but is associated with the ERK family of soluble kinases (Volonte C. et al., Mol. Biol. Cell 1993, 4(1):71-78) and has a role in the protection of neurons against apoptosis. All the neurotrophins can bind to this receptor.

The specificity of individual neurotrophins is determined by their binding to p140$^{trk}$, a particular type of tyrosine kinase (Trk) receptors, with NGF and NT-3 binding to TrkA, while BDNF and NT-4/5 binding to TrkB. The binding is followed by the receptor dimerization, resulting in autophosphorylation of intracellular tyrosine residues of the receptor by internal domains of the kinase. This in turn initiates a cascade of enzymatic reactions that mediate biological effects of neurotrophins, including an increased survival of neurons (Barbacid M., J. Neurobiol. 1994, 25(11): 1386-1403).

Neurotrophins are homodimers composed of two identical subunits each having approximately 120 amino acid residues and bound by hydrophobic interactions. X-ray structure analysis conducted for the NGF homodimer (McDonald N. Q. et al., J. Mol. Biol. 1991, 219(4): 595-601) and for the BDNF/NT-3 heterodimer (Robinson R. C. et al., Biochemistry 1995, 34(13): 4139-46) demonstrated a common 3D structure of neurotrophins. They all contain exposed structural units called loops 1, 2, 3 and 4 which are hairpin structures three of which have beta-turn sections at their ends (the so-called sections A-A", A'''-B and C-D, loops 1, 2, 4) and one section of 3 consecutive reverse turns (called section B-C, loop 3). These hairpin structures are thought to be responsible for the specific binding to a particular type of neurotrophin receptors.

Using site-directed mutagenesis (by transplanting loop 2 from BDNF into NGF), the specific binding of BDNF to TrkB receptor was shown to be determined by loop 2. This chimeric neurotrophin could bind to TrkB rather than TrkA and displayed a BDNF-like activity (Ibanez C. F. et al., EMBO J. 1993, 12(6): 2281-93). Furthermore, additional residues of loops 3 (Gln84) and 4 (Lys96 and Arg97) are important for the TrkB activation, but are thought not to be involved in its binding. All these residues are located on the surface of the molecule.

For NGF, it was shown that a stretch of amino acids from 29 to 35 corresponding to the loop 2 is responsible for the specific binding to TrkA. Synthetic peptides corresponding to the NGF sequence 29-35 were found to be NGF antagonists. Loop 1 was responsible for the binding to p75 receptor (McDonald and Chao. Structural determinants of neurotrophin action. JBC 270, 19669-19672, 1995; Longo et al. Synthetic NGF peptides prevent neuronal death via p75 receptor-dependent mechanism. J. Neurosci. Res., 1997).

The ability of neurotrophins to protect neurons in experimental models of neurodegenerative disease gave rise to the optimism concerning their potential therapeutic applications. In fact, however, neurotrophins were unsuccessful drugs because, being proteins, they are unavailable orally, unable to cross the blood-brain barrier and other biological barriers and are rapidly degraded in the bloodstream. Moreover, neurotrophins have pleiotropic actions and can induce carcinogenesis. The interaction of neurotrophins with the p75 receptor induces neuronal death by apoptosis. A considerable drawback of neurotrophins is the development of pain syndrome upon their use. This is related to the involvement of neurotrophins in the endogenous regulation of pain. Clinical applications of neurotrophins were unsuccessful (Penn R. D. et al., Neurosurgery 1997, 40(1):94-99; discussion 99-100, 1997). This led to attempts at producing their low molecular weight analogs, stable in the bloodstream and capable of crossing the gastro-intestinal and blood-brain barriers. It was suggested that low molecular weight analogs of neurotrophins would produce only partial biological effects due to their presumably selective interaction with some of the binding sites on a subpopulation of the neurotrophin receptors and thus would only activate the desired units of signaling cascades. There are several patents for low molecular weight peptide analogs of neurotrophins. Linear peptides having sequences that correspond to the respective sequences of hairpin structures exhibited an antagonist activity (Longo F. M. et al., Cell Regul. 1990, 1(2): 189-195). Peptide agonists of neurotrophins were obtained from among cyclic peptides able to maintain a conformation similar to the beta-turn conformation of neurotrophin loops. The provision of an agonist activity required the creation of bivalent analogs mimicking the homodimer structure of neurotrophins. Thus, Longo et al. (F. M. Longo et al., 1999, U.S. Pat. No. 5,958,875) have patented cyclic monomeric and dimeric peptides having sequences that correspond to a.a. 43-47 and 92-97 of NGF (loops 2 and 4). The cycles are formed using disulfide bonds at accessory cysteine or penicillamine residues introduced into said peptides. When tested in vitro, bicyclic analogs demonstrated an agonist activity.

Similar compounds have been patented by Saragovi et al. (H. U. Saragovi et al., 2002, U.S. Pat. No. 6,017,878). Cyclic peptide analogs are formed using disulfide or other (ionic, metal chelate etc.) bonds between linear peptides with sequences that fully or partially correspond to a.a. 28-36 of loop 1, 42-49 of loop 2, 59-67 and 91-99 of loops 3 and 4 in NGF. A minimal molecular weight of a cyclic peptide having an agonist activity is 1500 dalton, the peptide comprising 16 amino acids. The peptides are active in vitro.

Richard Hughes (R. A. Hughes et al., 2000, PCT WO 00/75176 A1) has filed a patent application for mono-, bi- and tricyclic peptide analogs of loops 2 and 4 in BDNF having both agonist and antagonist activities. Disulfide bridges are used for the cyclisation, and the cycles are linked both via the disulfide bridges and through carboxyl and amine groups of the side chain amino acids. The spacer length affects the activity, with maximal activity displayed by bivalent analogs with the same distance between the cyclic peptide fragments as in BDNF. An agonist activity is also displayed by monomeric cyclic peptides, analogs of the p75 receptor binding site at loop 4 of BDNF.

Thus, in all cases the binding to neurotrophin receptors is provided by the presence of an extended site that generally corresponds to a pentapeptide (except for a tripeptide site at loop 4 of BDNF that interacts with the p75 receptor), and the formation of an active beta-turn conformation requires that this site is cycled. In the presence of the Trk receptor binding, an agonist activity is achieved by combining two of these cycles into a bivalent entity.

The compounds described in the references cited above, however, neither disclose nor suggest any novel structural variations of the claimed compounds.

SUMMARY OF THE INVENTION

The object of this invention is to produce low molecular weight analogs of the neurotrophins NGF and BDNF having either agonist or antagonist activities. This object has been achieved by using minimal dipeptide sequences of the neurotrophins as ligands of the neurotrophin receptors. We acted on an assumption that an essential interaction between neurotrophin loops and a tyrosine kinase receptor takes place at a supersmall region that is most exposed and coinciding with a central portion of the beta-turn loop region or at least located in the immediate vicinity to it. This corresponds to an N-acylated dipeptide ligand which can maintain a required conformation for relatively long without a covalent cyclisation. In the case of NGF and BDNF loop 4 mimetics, these dipeptides had an antagonist activity since they were able to bind to the Trk receptor but unable to dimerize it. To produce a bivalent structure with an agonist activity, two dipeptides could be combined with a conventional linker consisting of internal methylene groups and terminal active groups, for which any length could be chosen. In the case of loop 1 mimetics, an agonist activity was also displayed by monomeric dipeptides, probably due to their indirect effect via the p75 receptor. In order to block the terminal charged groups of a dipeptide it was necessary to introduce a substituent. Conveniently, substituents were selected so as to mimic the preceding and the subsequent amino acid residues. All this made it possible to produce neurotrophin analogs possessing either agonist or antagonist activities with a minimal molecular weight of less than 1000 daltons. As a result, we found that the object of the invention could be achieved by compounds of general formula I:

$$(R-CH_2-CO-A-B-NH-R')_n \qquad (I)$$

where:

A and B are amino acid residues of a dipeptide sequence AB;

R is a side chain radical of the amino acid residue preceding the dipeptide fragment AB in the neurotrophin sequence or H or a bivalent radical —R—, in particular —$(CH_2)_m$—;

R' is a side chain radical of the amino acid residue following the dipeptide fragment AB in the neurotrophin sequence or H or a bivalent radical —R'—, in particular —$(CH_2)_m$—.

In the presence of a bivalent radical —R'— or —R— n=2 and the compound is a dimer having monomeric dipeptides linked by a C-terminal spacer —R—R— or an N-terminal spacer —R'—R'—. In other cases n=1 and the compound is a substituted monomeric dipeptide.

Exemplary embodiments of the invention are represented by the following compounds:

| | Formula | Code |
|---|---|---|
| | NGF loop 4 analogs: | |
| 1. | HOOC($CH_2)_2$C(O)-Glu-Lys-$NH_2$ | GK-1 |
| 2. | HOOC($CH_2)_2$C(O)-Glu-Lys-NH<br>                                          ($CH_2)_6$<br>HOOC($CH_2)_2$C(O)-Glu-Lys-NH | GK-2 |
| 3. | HOOC($CH_2)_2$C(O)-Glu-Lys-NH<br>                                          ($CH_2)_5$<br>HOOC($CH_2)_2$C(O)-Glu-Lys-NH | GK-2b |
| 4. | HOOC($CH_2)_2$C(O)-Glu-Lys-NH<br>                                          ($CH_2)_4$<br>HOOC($CH_2)_2$C(O)-Glu-Lys-NH | GK-2c |
| 5. | HOOC($CH_2)_2$C(O)-Glu-Lys-NH<br>                                          ($CH_2)_3$<br>HOOC($CH_2)_2$C(O)-Glu-Lys-NH | GK-2d |
| 6. | HOOC($CH_2)_2$C(O)-Glu-Lys-NH<br>                                          ($CH_2)_2$<br>HOOC($CH_2)_2$C(O)-Glu-Lys-NH | GK-2e |

| | Formula | Code |
|---|---|---|
| 7. | HOOC(CH$_2$)$_2$C(O)-Glu-Lys-NH<br>                                                             (CH$_2$)$_5$<br>                                                             C(O)<br>                                                             NH<br>                                                           (CH$_2$)$_3$<br>                                                             NH<br>                                                             C(O)<br>                                                             (CH$_2$)$_5$<br>HOOC(CH$_2$)$_2$C(O)-Glu-Lys-NH | GK-2a |
| 8. | HOOC(CH$_2$)$_2$C(O)-Gly-Lys-NH<br>                                                             (CH$_2$)$_6$<br>HOOC(CH$_2$)$_2$C(O)-Gly-Lys-NH | GK-2w |
| NGF loop 1 analogs: | | |
| 9. | CH$_3$C(O)-Lys-Glu-NH$_2$ | GK-3 |
| 10. | CH$_3$C(O)-Lys-Glu-NH<br>                             (CH$_2$)$_6$<br>CH$_3$C(O)-Lys-Glu-NH | GK-4 |
| 11. | NH$_2$—(CH$_2$)$_5$—C(O)-Gly-Lys-NH$_2$ | GK-5 |
| 12. | NH$_2$—(CH$_2$)$_5$—C(O)-Gly-Lys-NH<br>                                                   (CH$_2$)$_6$<br>NH$_2$—(CH$_2$)$_5$—C(O)-Gly-Lys-NH | GK-6 |
| 13. | CH$_3$C(O)-Gly-Lys-NH—(CH$_2$)$_3$—COOH | GK-7 |
| 14. | C(O)-Gly-Lys-NH—(CH$_2$)$_3$—COOH<br>(CH$_2$)$_4$<br>C(O)-Gly-Lys-NH—(CH$_2$)$_3$—COOH | GK-8 |
| BDNF loop 4 analogs: | | |
| 15. | HOOC(CH$_2$)$_2$C(O)-Ser-Lys-NH$_2$ | GSB-104 |
| 16. | HOOC(CH$_2$)$_2$C(O)-Ser-Lys-NH<br>                                                        (CH$_2$)$_6$<br>HOOC(CH$_2$)$_2$C(O)-Ser-Lys-NH | GSB-106 |
| 17. | HO—(CH$_2$)$_2$C(O)-Lys-Lys-NH<br>                                          (CH$_2$)$_6$<br>HO—(CH$_2$)$_2$C(O)-Lys-Lys-NH | GSB-120 |
| 18. | CH$_3$C(O)-Asp-Ser-NH$_2$ | GBK-108 |
| BDNF loop 1 analogs: | | |
| 19. | HOOC(CH$_2$)$_2$C(O)-Met-Ser-NH$_2$ | GSB-207 |
| 20. | HOOC(CH$_2$)$_2$C(O)-Met-Ser-NH<br>                                                   (CH$_2$)$_7$<br>HOOC(CH$_2$)$_2$C(O)-Met-Ser-NH | GSB-214 |
| 21. | CH$_3$C(O)-Asp-Met-NH$_2$ | GBK-201 |

The examination of biological properties of the claimed compounds revealed that depending on their structure they can display a neuroprotective or a neurodegenerative activity and, depending on which loop they mimic, a predominantly neurotrophic or differentiation-inducing activity.

The compounds having a neuroprotective activity can increase the phosphorylation of tyrosine kinases and the amount of the heat shock proteins Hsp32 and/or Hsp70.

The examination of pharmacological properties of the most active of the claimed compounds GK-2, a loop 4 mimetic, revealed that it has an anti-Parkinsonian, anti-ischemic, anti-amnestic, neuroprotective, anti-stroke activities and is effective in an experimental model of Alzheimer's disease. The evaluation of BDNF mimetics in a classical test for antidepressant activity (Porolt test) revealed that the dimeric mimetics of BDNF loops 1 and 4 possess an antidepressant activity whereas the monomeric mimetics show a prodepressant activity.

BRIEF DESCRIPTION OF THE DRAWINGS

FIG. 1.1. Effects of different molar concentrations of the peptide GK-2c on the survival of HT22 cells.

*$p<0.05$ versus control according to Student's t-test.

FIG. 1.2. Neuroprotective effects of the peptide GK-6 under oxidative stress conditions. MTT test. GK-6 was added 24 h before adding $H_2O_2$.

*$p<0.05$ versus control, ^$p<0.05$ versus $H_2O_2$ according to Student's t-test.

FIG. 1.3. Neuroprotective effects of the peptide GK-2b under oxidative stress conditions.

*$p<0.05$ versus control, ^$p<0.05$ versus $H_2O_2$ according to Student's t-test.

FIG. 1.4. Neuroprotective effects of the peptide GK-2d under oxidative stress conditions.

*$p<0.05$ versus control, ^$p<0.05$ versus $H_2O_2$ according to Student's t-test.

FIG. 1.5. Neuroprotective effects of the peptide GK-2e under oxidative stress conditions.

*$p<0.05$ versus control, ^$p<0.05$ versus $H_2O_2$.

FIG. 1.6. Effects of the peptide GSB-104 on the survival of HT22 cells under oxidative stress conditions when added 24 h before adding $H_2O_2$. MTT test.

*$p<0.05$ versus control, ^$p<0.05$ versus $H_2O_2$ according to Student's t-test.

FIG. 1.7. Effects of the peptide GSB-106 on the survival of HT22 cells under oxidative stress conditions.

*$p<0.05$ versus control, ^$p<0.05$ versus $H_2O_2$ according to Student's t-test.

FIG. 1.8. Effects of the peptide GBK-108 on the survival of HT22 cells under oxidative stress conditions when added 24 h before adding $H_2O_2$.

*$p<0.05$ versus control, ^$p<0.05$ versus $H_2O_2$ according to Student's t-test.

FIG. 1.9. Effects of $10^{-5}$ M and $10^{-8}$ M GK-2 on the survival of PC12 cell line when added at the same time as MPTP.

*p<0.05 versus control, ˆp<0.05 versus MPTP according to Student's t-test.

FIG. 1.10. Effects of $10^{-5}$ M and $10^{-8}$ M GK-2 on the survival of PC12 cell line when added 24 h before adding MPTP.

*p<0.05 versus control, ˆp<0.05 versus MPTP according to Student's t-test.

FIG. 1.11. Effects of GK-2a, GK-3, GK-4, and GK-5 on the survival of PC12 cell line in the model of Parkinson's disease when added 24 h prior to MPTP.

*p<0.05 versus control, ˆp<0.05 versus MPTP according to Student's t-test.

FIG. 1.12. Neuroprotective effects of the peptide GSB-106 under conditions of glutamate neurotoxicity.

*p<0.05 versus control, ˆp<0.05 versus glutamate according to Student's t-test.

FIG. 1.13. Effects of different concentrations of the peptides GK-1 and GK-2 on the amount of Hsp70 in cultured hippocampal neuronal cell line HT22.

Lane 1: heat shock (42° C., 1 h); lane 2: NGF (100 ng/ml); lane 3: control; lane 4: GK-1 ($10^{-5}$ M); lane 5: GK-1 ($10^{-8}$ M); lane 6: GK-2 ($10^{-5}$ M); lane 7: GK-2 ($10^{-8}$ M); lane 8: GK-1+GK-2 ($10^{-5}$ M).

FIG. 1.14. Effects of different concentrations of the peptides GK-1 and GK-2 on the amount of Hsp32 in cultured hippocampal neuronal cell line HT22.

Lane 1: heat shock (42° C., 1 h); lane 2: NGF (100 ng/ml); lane 3: control; lane 4: GK-1 ($10^{-5}$ M); lane 5: GK-1 ($10^{-8}$ M); lane 6: GK-2 ($10^{-5}$ M); lane 7: GK-2 ($10^{-8}$ M); lane 8: GK-1+GK-2 ($10^{-5}$ M).

FIG. 1.15. Effects of the peptides GK-3, GK-4 and GK-5 on the amount of Hsp70 in cultured hippocampal neuronal cell line HT22.

Lanes 1 and 2: control; lanes 3 and 4: NGF (100 ng/ml); lanes 5 and 6: GK-5 ($10^{-6}$ M); lane 7: GK-3 ($10^{-6}$ M); lane 8: GK-4 ($10^{-7}$ M); lane 9: heat shock (42° C., 1 h).

FIG. 1.16. Effects of the peptides GK-3, GK-4 and GK-5 on the amount of Hsp32 in cultured hippocampal neuronal cell line HT22.

Lanes 1 and 2: control; lanes 3 and 4: NGF (100 ng/ml); lanes 5 and 6: GK-5 ($10^{-6}$ M); lane 7: GK-3 ($10^{-6}$ M); lane 8: GK-4 ($10^{-7}$ M); lane 9: heat shock (42° C., 1 h).

FIG. 1.17. Effects of GK-2 and GK-3 on the phosphorylation of tyrosine kinase A in cultured hippocampal neuronal cell line HT22. Exposition for 1 min. Densitometry results of the original Western blot.

FIG. 1.18. Effects of GK-4 and GK-5 on the phosphorylation of tyrosine kinase A in cultured hippocampal neuronal cell line HT22. Exposition for 1 min. Densitometry results of the original Western blot.

FIG. 1.19. Effects of GK-1 ($10^{-5}$ M) on the phosphorylation of tyrosine kinase A in cultured hippocampal neuronal cell line HT22. Exposition for 1 min. Densitometry results of the original Western blot. *p<0.05 versus control according to Student's t-test.

FIG. 1.20. Effects of GK-2 and NGF on the phosphorylation of tyrosine kinase A in cultured hippocampal neuronal cell line HT22. Exposition for 2 min. Densitometry results of the original Western blot.

FIG. 2.1. Effects of GK-2 (1 mg/kg i.p.) on the lesion volume in the rat brain.

FIG. 2.2. Reduction of neurological deficit in post-ischemic rats treated with GK-2 (1 mg/kg i.p.). (A): 4 days after ischemia; (B): 7 days after ischemia, the limb-placing test.

FIG. 2.3. Reduction of neurological deficit in post-ischemic rats treated with GK-2 (1 mg/kg i.p.). (A): 4 days after ischemia; (B): 7 days after ischemia, the cylinder test.

*p<0.05 versus control according to the Mann-Whitney U-test.

FIG. 2.4. Protective effects of GK-2 (1 mg/kg i.p.) in photothrombosis of rat brain prefrontal cortex. *p<0.05 versus NaCl.

FIG. 2.5. Effects of GK-2 (1 mg/kg i.p.) on the horizontal motor activity of the operated rats in the open-field test.

*p=0.01 versus sham-operated rats according to the Mann-Whitney U-test;

*p=0.05 versus operated only rats according to the Mann-Whitney U-test.

FIG. 2.6. Effects of GK-2 (1 mg/kg i.p.) on the vertical motor activity of the operated rats in the open-field test.

*p=0.03 versus sham-operated rats according to the Mann-Whitney U-test;

*p=0.04 versus operated only rats according to the Mann-Whitney U-test.

FIG. 2.7. Effects of GK-2 (1 mg/kg i.p.) on the object smelling time by the operated rats in the object exploration test. *p=0.048 versus sham-operated rats according to the Mann-Whitney U-test.

FIG. 2.8. Effects of GK-2 (1 mg/kg i.p.) on the object smelling kinetics by the operated rats in the object exploration test. *p=0.02 versus sham-operated rats according to the exact Fisher test.

FIG. 2.9. Effects of GK-2 (1 mg/kg i.p.) on the survival of rat cerebral cortex cells following a bilateral ligation of the carotid artery (MTT test).

*p=0.02 versus sham-operated rats according to the Mann-Whitney U-test;

*p=0.04 versus operated only rats according to the Mann-Whitney U-test.

FIG. 2.10. Effects of GK-2 (1 mg/kg i.p.) on the apomorphine-induced stereotyping intensity in rats. *p=0.02 versus apomorphine.

FIG. 2.11. Effects of GK-2 (1 mg/kg i.p.) on the spontaneous arm alternations in the T-maze by scopolamine-treated rats.

*p=0.0015 versus control; #p=0.02 versus active control.

FIG. 2.12. Effects of GSB-106 (1 mg/kg i.p., 24 hrs before the second landing) on the behavioral dispair in mice. *p<0.05 versus control according to the Mann-Whitney U-test.

FIG. 2.13. Effects of different doses of GBK-108 and GBK-201 (24 hrs before the second landing) on the behavioral dispair in mice. *p<0.05 versus control according to the Mann-Whitney U-test.

DETAILED DESCRIPTION OF THE INVENTION

The compounds of formula I above were prepared by methods of peptide synthesis well-known in the art. A general preparation process for the target compounds comprises mixing and coupling of the desired amino acids, as a rule, in a homogeneous phase.

The coupling in a homogeneous phase may be accomplished in the following manner:

(a) coupling of an amino acid having a free carboxyl group and a protected another reactive group with an amino acid having a free amine group and protected other reactive groups, in the presence of a coupling agent;

(b) coupling of an amino acid having an activated carboxyl group and a protected another reactive group with an amino acid having a free amine group and protected other reactive groups;

(c) coupling of an amino acid having a free carboxyl group and a protected another reactive group with an amino acid having an activated amine group and protected other reactive groups.

The carboxyl group can be activated by converting it into an acid chloride, azido, anhydride group or an activated ester such as N-hydroxysuccinimide, N-hydroxybenzotriazole, pentaclorophenyl or p-nitrophenyl ester. The amine group can be activated by converting it into a phosphitamide or by the "phosphorase" method.

The most general methods for the coupling reaction are the carboxydiimide method, the azide method, the mixed anhydride method and the activated ester method. These methods are described in "The Peptides", vol. 1, 1965 (Academic Press), E. Schroeder, K. Lubke; or "The Peptides", vol. 1, 1979 (Academic Press), E. Gross, J. Meienhofer.

The preferred coupling method for the preparation of peptides of formula I is the activated ester method, which is advantageously performed by using a succinimide, pentaclorophenyl or p-nitrophenyl ester of the amine-protected amino acid. The preferred solvent is dimethylformamide.

The mixed anhydride method was also employed under Anderson's conditions: G. W. Anderson et al., J. Am. Chem. Soc., 89, 5012-5017 (1967).

The reactive groups which should be prevented from participating in the coupling reaction can be protected by easily removable groups, such as by hydrolysis or reduction. For example, the carboxyl group can be protected by esterification with ethanol, methanol, t-butanol or benzyl alcohol.

The amine group is typically protected by acidic groups, e.g. by aliphatic, aromatic, heterocyclic carboxylic acid residues, such as acetyl, benzoyl, pyridinecarboxy groups, or by acidic groups derived from carbonic acid such as ethoxycarbonyl, benzyloxycarbonyl, t-butyloxycarbonyl groups; or by acidic groups derived from a sulfonic acid such as p-toluenesulfonyl group.

Commercially available protected amino acids were used for the synthesis of the claimed compounds, mostly in the form of carbobenzoxy derivatives and t-butyloxycarbonyl derivatives of the respective amine groups. The carboxyl groups were protected by benzyl and t-butyl esters. The hydroxyl group of serine was protected by a benzyl ester.

N-acylated derivatives were prepared by using the respective anhydrides, in particular succinic or acetic anhydride.

Amides of the peptides of formula I are prepared by ammonolysis (i.e. the reaction with $NH_3$) of an alkyl ester of the respective dipeptide or by reaction with an amino acid in the form of a desired amide. Amides of the dipeptides can also be prepared by any suitable method such as by an amine treatment in the presence of a coupling agent.

Diamines were used for spacers, particularly hexamethylenediamine, which were introduced in the reaction with a carboxy component under conditions of peptide synthesis as described above.

The protective groups were removed in accordance with the nature of a particular group, namely, the carbobenzoxyl groups and benzyl groups were removed by hydrogenolysis by passing hydrogen in methanol over a 10% palladium on carbon, the t-butyloxycarbonyl groups and t-butyl groups were removed in an acidic medium by HCl in dioxane or by anhydrous trifluoracetic acid.

EXAMPLES

The following abbreviations are used hereinafter:
Ad: adipyl
Asp: aspartyl
Boc: tret-butyloxycarbonyl
Bzl: benzyl
DCCD: dicyclohexylcarbodiimide
DEAE: diethylaminoethyl
DETMDA: N,N-diethyltrimethylenediamin
DIEA: diisopropylethylamine
DMFA: dimethylformamide
DMPDA: dimethylpropyldiamine
DMSO: dimethylsulfoxide
Glu: glutamyl
Gly: glycyl
HPLC: high performance liquid chromatography
IDEA: isopropyldiethylamine
Lys: lysyl
Met: methionyl
Np: nitrophenyl
OSU: oxysuccinyl
Pfp: pentafluorophenyl
PMR: proton magnetic resonance
PyBOP: benzotriaxolyloxytris(pyrrolidino)phosphonium hexafluorophosphate
sat.: saturated
Ser: seryl
SP: sulfopropyl
t-Bu: tret-butyl
TEA: triethylamine
TFA: trifluoracetic acid
THF: tetrahydrofuran
TLC: thin layer chromatography
Ts: p-toluenesulfate
Z: carbobenzoxy In the examples:
melting temperatures were determined in open-end capillaries without any correction;

specific optical rotation values were determined using an automated Perkin-Elmer 241 polarometer;

proton magnetic resonance (PMR) spectra were acquired using a Bruker AC-250 spectrometer, with chemical shifts expressed in ppm relative to tetramethylsilane, and the following abbreviations were used to denote the resonance signals: s, singlet; d, doublet; dd, double doublet; t, triplet; q, quadruplet; m, multiplet;

thin layer chromatography was performed on Kieselgel 60 plates (Merck, Germany), developed with ninhydrine, iodine vapor or by UV irradiation;

TLC was conducted in the following solvent systems: chloroform-methanol-acetic acid-water, 15:10:2:3 (A); n-butanol-pyridine-acetic acid-water, 15:10:3:6 (B); chloroform-methanol, 9:1 (C); chloroform-ethanol, 9:1 (D); n-butanol-acetic acid-water, 4:1:1 (E); hexane-ethyl acetate, 2:1 (F); hexane-ethyl acetate, 4:1 (G); ethyl acetate (H); dioxane-water, 10:1 (I), chloroform-methanol-water, 80:10:1 (J); pyridine-water-acetic acid-ethyl acetate, 20:11:6:120 (K); chloroform-methanol-water-acetic acid, 60:45:6.4:13.6 (L).

$R_f$ values are respectively denoted as $R_f(X)$ meaning an $R_f$ value in the system X (A, B, C etc.).

Elemental analysis data for the compounds in regard to the relative percentages of C, H and N may deviate from theoretical values by not more than 0.4%.

Example 1

The synthesis of N-monosuccinyl-glutamyl-lysine amide, $HOOC(CH_2)_2CO$-Glu-Lys-$NH_2$ (GK-1)

a) The preparation of N-benzyloxycarbonyl-γ-t-butyl-glutamyl-$N^\epsilon$-t-butyloxycarbonyl-lysine amide, Z-Glu(OBu$^t$)-Lys(Boc)-$NH_2$ A solution of 4.0 g (8.4 mmol) N-benzyloxycarbonyl-$N^\epsilon$-tert-butyloxycarbonyl-lysine N-oxysuccinimide ester (Z-Lys(Boc)-OSu) in 20 ml DMFA was treated with 2 ml conc. ammonia for 5 min followed by dilution with water, and the precipitated N-benzyloxycarbonyl-$N^\epsilon$-tert-butyloxycarbonyl-lysine amide (Z-Lys(Boc)-$NH_2$) was filtered off. The resulting product was dissolved in methanol, then 3.0 g of 10% Pd/C was added and hydrogenated at room temperature. The catalyst was filtered off, the solvent was removed in vacuo, and the residue was taken up in 20 ml DMFA. To this solution 3.9 g (9.0 mmol) N-benzyloxycarbonyl-γ-t-butyl-glutamic acid N-oxysuccinimide ester (Z-Glu(OBu$^t$)—OSu) was added. The reaction mixture was stirred for 6 h at room temperature (TLC control), then 2 ml DMPDA was added and allowed to stand for 30 min. The reaction mixture was diluted with 200 ml ethyl acetate and washed successively with 100 ml water, 100 ml 2% $H_2SO_4$, and 100 ml 3% $Na_2CO_3$ followed by evaporation. The residue was recrystallized from 80 ml methanol and 30 ml water. It was used without drying.

b) The preparation of N-monosuccinyl-γ-t-butyl-glutamyl-$N^\epsilon$-t-butyloxycarbonyl-lysine amide, $HOOC(CH_2)_2$CO-Glu(OBu$^t$)-Lys(Boc)-$NH_2$ The Z-Glu(OBu$^t$)-Lys(Boc)-$NH_2$ prepared in (a) was hydrogenated in methanol over 10% Pd/C at room temperature. When the starting compound disappeared (TLC control), the catalyst was filtered off, and the solvent was removed in vacuo. The residue was taken up in 20 ml DMFA and 1.2 g (12.0 mmol) succinic anhydride was added. The reaction mixture was stirred at room temperature until the reaction was complete (TLC control), then 2 ml DMPDA was added and allowed to stand for 30 min. The reaction mixture was diluted with 200 ml ethyl acetate and washed successively with 100 ml water, 100 ml 2% $H_2SO_4$, and 100 ml 3% $Na_2CO_3$. The product was crystallized following the evaporation of the ethyl acetate solution. It was used without drying.

c) The preparation of N-monosuccinyl-glutamyl-lysine amide, $HOOC(CH_2)_2$CO-Glu-Lys-$NH_2$ (GK-1)

The $HOOC(CH_2)_2$CO-Glu(OBu$^t$)-Lys(Boc)-$NH_2$ prepared in (b) was treated with 30 ml HCl in dioxane, whereby the compound was dissolved and formed a sticky precipitate in the course of the reaction. After standing for 30 min, the solvent was poured off, and the residue was washed with diethyl ether and taken up in 50 ml water followed by the addition of 100 ml acetic acid. The resulting paste containing the product in the acetate form was applied onto a DEAE-Sephadex column, 5×15 cm. The column was eluted with 0.1 M pyridine-acetate buffer. The relevant fractions were collected (TLC control), evaporated and dried in vacuo to yield 1.3 g (total recovery 36%) of a white crystalline product. $R_f$ 0.50 (A), $R_f$ 0.22 (B); m.p. 216° C. (decomp.); $[\alpha]^{25}_D$ −37.0° (c=0.1; water). $C_{15}H_{26}N_4O_7$.

$^1H$ NMR (DMSO-$d_6$-$CF_3$COOD): 1.33 (2H, m, $C^\gamma H_2$ Lys), 1.54 (2H, m, $C^\delta H_2$ Lys), 1.50 and 1.72 (2H, 2m, $C^\beta H_2$ Lys), 1.74 and 1.92 (2H, 2m, $C^\beta H_2$ Glu), 2.29 (2H, t, $C^\gamma H_2$ Glu), 2.44 (4H, m, HOOC$\underline{CH_2CH_2}$CO—), 2.78 (2H, m, $C^\epsilon H_2$ Lys), 4.18 (1H, m, $C^\alpha H$ Lys), 4.23 (1H, m, $C^\alpha H$ Glu), 7.08 and 7.30 (2H, 2s, $NH_2$ amide), 7.72 (3H, m, $NH_3^+$ Lys), 7.88 (1H, d, NH Lys), 8.17 (1H, d, NH Glu). The $\underline{H}OOC(CH_2)_2CO$— and —COO$\underline{H}$ Glu are exchangeable with HDO.

Example 2

The synthesis of bis-(N-monosuccinyl-glutamyl-lysine) hexamethylenediamide, $(HOOC(CH_2)_2CO$-Glu-Lys-$NH)_2$—$(CH_2)_6$ (GK-2)

a) The preparation of bis-(N-benzyloxycarbonyl-$N^\epsilon$-t-butyloxycarbonyl-lysine) hexamethylenediamide, (Z-Lys(Boc)-$NH)_2$—$(CH_2)_6$ A solution of 4.3 g (9.0 mmol) N-benzyloxycarbonyl-$N^\epsilon$-t-butyloxycarbonyl-lysine N-oxysuccinimide ester (Z-Lys(Boc)-OSu) and 0.5 g (4.3 mmol) hexamethylenediamine in 20 ml DMFA was stirred for 4 h at room temperature, forming a cloudy solution. The reaction mixture was diluted with 80 ml water and allowed to stand for a few hours. The solidified precipitate was filtered off and washed with water. It was used without drying.

b) The preparation of bis-(N-benzyloxycarbonyl-γ-t-butyl-glutamyl-$N^\epsilon$-t-butyloxycarbonyl-lysine) hexamethylenediamide, (Z-Glu(OBu$^t$)-Lys(Boc)-$NH)_2$—$(CH_2)_6$ The (Z-Lys(Boc)-$NH)_2$—$(CH_2)_6$ prepared in (a) was hydrogenated in methanol over 10% Pd/C at room temperature. When the starting compound disappeared (TLC control), the catalyst was filtered off, and the solvent was removed in vacuo. The residue was taken up in 20 ml DMFA and 3.9 g (9.0 mmol) N-benzyloxycarbonyl-γ-t-butyl-glutamic acid N-oxysuccinimide ester (Z-Glu(OBu$^t$)—OSu) was added. The solution was stirred overnight at room temperature, then 2 ml DMPDA was added and allowed to stand for 30 min. The reaction mixture was diluted with 200 ml ethyl acetate and washed successively with 100 ml water, 100 ml 2% $H_2SO_4$, and 100 ml 3% $Na_2CO_3$. The ethyl acetate fraction was evaporated, and the residue was recrystallized from 80 ml methanol and 30 ml water. It was used without drying.

c) The preparation of bis-(N-monosuccinyl-γ-t-butyl-glutamyl-$N^\epsilon$-t-butyloxycarbonyl-lysine) hexamethylenediamide, $(HOOC(CH_2)_2CO$-Glu(OBu$^t$)-Lys(Boc)-$NH)_2$—$(CH_2)_6$ The (Z-Glu(OBu$^t$)-Lys(Boc)-$NH)_2$—$(CH_2)_6$ prepared in (b) was hydrogenated in methanol over 10% Pd/C at room temperature. When the starting compound disappeared (TLC control), the catalyst was filtered off, and the solvent was removed in vacuo. The residue was taken up in 20 ml DMFA and 1.2 g (12.0 mmol) succinic anhydride was added. The reaction mixture was stirred at room temperature until the reaction was complete (TLC control), then 2 ml DMPDA was added and allowed to stand for 30 min. The reaction mixture was diluted with 200 ml ethyl acetate and washed successively with 100 ml water, 100 ml 2% $H_2SO_4$, and 100 ml 3% $Na_2CO_3$. Following the evaporation of the ethyl acetate solution, the product was recrystallized. It was used without drying.

d) The preparation of bis-(N-monosuccinyl-glutamyl-lysine) hexamethylenediamide, $(HOOC(CH_2)_2CO$-Glu-Lys-$NH)_2$—$(CH_2)_6$ (GK-2)

The $(HOOC(CH_2)_2CO$-Glu(OBu$^t$)-Lys(Boc)-$NH)_2$—$(CH_2)_6$ prepared in (c) was dissolved in acetic acid and treated with 30 ml 4M HCl in dioxane. After standing for 40 min, the solvent was poured off, and the residue was washed with diethyl ether and taken up in 50 ml water followed by treating with an Amberlite IRA-410 resin under stirring until the pH was stabilized at pH ~2. The purification was performed by the C8 reversed phase HPLC using a 0 to 15% isopropanol gradient in 0.1M acetic acid. The relevant fractions were collected (TLC control), evaporated and dried in vacuo to yield 1.3 g (total recovery 32%) of the product as a white solid. $R_f$ 0.41 (A), $R_f$ 0.20 (B); m.p. 120-128° C. (no fixed m.p., highly hygroscopic); $[\alpha]^{25}{}_D$ –47.0° (c=0.1; water).

$^1$H NMR (DMSO-$d_6$-CF$_3$COOD): 1.24 and 1.40 (8H, m, NHCH$_2$CH$_2$CH$_2$CH$_2$CH$_2$CH$_2$NH—), 1.38 (4H, m, 2C$^\gamma$H$_2$ Lys), 1.53 (4H, m, 2C$^\delta$CH$_2$ Lys), 1.50 and 1.67 (4H, each m, 2C$^\beta$H$_2$ Lys), 1.78 and 1.90 (4H, each m, 2C$^\beta$H$_2$ Glu), 2.29 (4H, t, 2C$^\gamma$H$_2$ Glu), 2.44 (8H, m, 2HOOCCH$_2$CH$_2$CO—), 2.77 (4H, m, 2C$^\epsilon$H$_2$ Lys), 3.04 (4H, m, —NHCH$_2$CH$_2$CH$_2$CH$_2$CH$_2$NH—), 4.14 (2H, m, 2C$^\alpha$H Lys), 4.23 (2H, m, 2C$^\alpha$H Glu), 7.70 (6H, m, 2NH$_3{}^+$ Lys), 7.72 (2H, t, —NHCH$_2$CH$_2$CH$_2$CH$_2$CH$_2$CH$_2$NH—), 7.90 (2H, d, 2NH Lys), 8.18 (2H, d, 2NH Glu). The 2 HOOC(CH$_2$)$_2$CO— and 2 —COOH Glu are exchangeable with HDO.

Example 3

The synthesis of N-acetyl-lysyl-glutamic acid amide, CH$_3$CO-Lys-Glu-NH$_2$ (GK-3)

a) The preparation of γ-benzyl-glutamic acid amide, H-Glu(OBzl)-NH$_2$ 8.0 g (17.4 mmol) of N-t-butyloxycarbonyl-γ-benzyl-glutamic acid p-nitrophenyl ester (Boc-Glu(OBzl)-ONp) were dissolved in 30 ml DMFA, 3.5 ml aqueous ammonia was added and allowed to stand for 5 min. Then to the reaction mixture 100 ml water, 50 ml diethyl ether and 100 ml of hexane were added and allowed to stand at +5° C. for a few hours. The precipitate was filtered off, and the solid residue was washed with water and hexane. The resulting product was dissolved in 80 ml TFA, and the solution was kept for 1 h at room temperature. The solvent was removed in vacuo, and the residue was allowed to crystallize with ether. The residue that crystallized gradually was filtered off and washed with ether to yield 5.8 g (96%) of the product. M.p. 68-70° C., $[\alpha]^6{}_D$ +10.0° (c=0.3; water-ethanol, 1:2).

b) The preparation of N-t-butyloxycarbonyl-N$^\epsilon$-benzyloxycarbonyl-lysyl-γ-benzyl-glutamic acid amide, Boc-Lys(Z)-Glu(OBzl)-NH$_2$ 2.5 ml (18.0 mmol) TEA was added to a solution of 5.8 g (16.7 mmol) γ-benzyl-glutamic acid amide (H-Glu(OBzl)-NH$_2$) trifluoracetate and 9.0 g (18.0 mmol) N-t-butyloxycarbonyl-N$^\epsilon$-benzyloxycarbonyl-lysine p-nitrophenyl ester (Boc-Lys(Z)—ONp) in 30 ml DMFA under stirring and kept overnight at room temperature. When the reaction was complete (TLC control), 2 ml DMPDA was added and allowed to stand for 1 h. Then 200 ml water and 200 ml diethyl ether were added to the solution. The precipitate was filtered off and washed with water and ether to yield 9.3 g (93%) of the product. M.p. 122° C., $[\alpha]^{27}{}_D$ –10.7° (c=0.3; DMFA).

c) The preparation of N$^\epsilon$-benzyloxycarbonyl-lysyl-γ-benzyl-glutamic acid amide, H-Lys(Z)-Glu(OBzl)-NH$_2$ A solution of 9.3 g (15.5 mmol) Boc-Lys(Z)-Glu(OBzl)-NH$_2$ in 70 ml TFA was allowed to stand for 1 h. The solvent was removed in vacuo, and the residue was triturated with diethyl ether. The crystallizing precipitate was filtered off to yield 9.1 g (96%) of the product in the form of trifluoracetate. M.p. 145-146° C., $[\alpha]^{26}{}_D$ +13.3° (c=0.3; water-ethanol, 1:2).

d) The preparation of N-acetyl-lysyl-glutamic acid amide, CH$_3$CO-Lys-Glu-NH$_2$ (GK-3)

9.1 g (14.9 mmol) H-Lys(Z)-Glu(OBzl)-NH$_2$ trifluoracetate and 3.0 g (16.6 mmol) acetic acid p-nitrophenyl ester (AcONp) were dissolved in 30 ml DMFA, and 2.3 ml (16.6 mmol) TEA was added under stirring. The reaction mixture was stirred for 3 h at room temperature (TLC control), and then 200 ml ether and 200 ml water were added. The precipitate was filtered off and dried in vacuo. The resulting product was dissolved in 150 ml methanol, then 3.0 g 10% Pd/C was added and hydrogenated under stirring at 40° C. using 3 ml (59.9 mmol) conc. ammonium formate being added in portions. After stirring for 4 h, the catalyst was filtered off and washed with methanol, and the filtrate was evaporated. The resulting product was dissolved in 500 ml water and purified on a 100 ml SP-Sephadex column using a 0.1 to 0.2 M pyridine-acetate buffer gradient. The relevant fractions (TLC control) were collected, evaporated and re-evaporated with isopropanol. The residue was triturated with methanol, and the crystallizing solid precipitate was filtered off and dried in vacuo to yield 2.2 g (40%; total recovery 34%) of the product as white crystals. $R_f$ 0.43 (A), $R_f$ 0.27 (B); m.p. 198-199° C.; $[\alpha]^{26}{}_D$ –32.3° (c=1; water). $C_{13}H_{24}N_4O_5$.

$^1$H NMR (DMSO-$d_6$-CF$_3$COOD): 1.32 (2H, m, C$^\gamma$H$_2$ Lys), 1.52 (2H, m, C$^\delta$H$_2$ Lys), 1.65 and 1.80 (2H, 2m, C$^\beta$H$_2$ Lys), 1.85 (3H, s, CH$_3$CO—), 2.00 and 1.82 (2H, 2m, C$^\beta$H$_2$ Glu), 2.21 (2H, t, C$^\beta$H$_2$ Glu), 2.75 (2H, m, C$^\epsilon$H$_2$ Lys), 4.17 (2H, m, C$^\alpha$H$_2$ Lys, C$^\alpha$H$_2$ Glu), 7.07 and 7.81 (2H, 2s, NH$_2$ amide), 7.68 (3H, m, N$^\epsilon$H$_3{}^+$ Lys), 7.91 (1H, d, NH Glu), 8.08 (1H, d, NH Lys). The COOH Glu signal is exchangeable with HDO.

Example 4

The synthesis of bis-(N-acetyl-lysyl-glutamic acid) hexamethylenediamide, (CH$_3$CO-Lys-Glu-NH)$_2$—(CH$_2$)$_6$ (GK-4)

a) The preparation of bis-(γ-benzyl-glutamic acid)hexamethylenediamide, (H-Glu(OBzl)-NH)$_2$—(CH$_2$)$_6$ 6.0 g (13.1 mmol) N-t-butyloxycarbonyl-γ-benzyl-glutamic acid (Boc-Lys(Z)—ONp) p-nitrophenyl ester (Boc-Glu(OBzl)-ONp) and 0.76 g (6.5 mmol) hexamethylenediamine were dissolved in 30 ml DMPDA and stirred overnight at room temperature. When the reaction was complete (TLC control), 1 ml DMPDA was added and allowed to stand for 1 h at room temperature. Then 150 ml ethyl acetate and 200 ml water were added to the solution and washed with 150 ml 3% H$_2$SO$_4$ and 100 ml water. The ethyl acetate fraction was evaporated, and the resulting solid residue was dissolved in 80 ml TFA and allowed to stand for 1 h at room temperature. The solvent was then distilled off, and the residue was triturated with diethyl ether. After standing at +5° C. for a few hours, the ether was poured of, and the solid residue was dried in vacuo to yield 4.9 g (96%) of the product.

b) The preparation of bis-(N-t-butyloxycarbonyl-N$^\epsilon$-benzyloxycarbonyl-lysyl-γ-benzyl-glutamic acid) hexamethylenediamide, (Boc-Lys(Z)-Glu(OBzl)-NH)$_2$—(CH$_2$)$_6$ 4.9 g (6.2 mmol) (H-Glu(OBzl)-NH)$_2$—(CH$_2$)$_6$ and 6.6 g (13.2 mmol) N-t-butyloxycarbonyl-N$^\epsilon$-benzyloxycarbonyl-lysine p-nitrophenyl ester (Boc-Lys(Z)—ONp) were dissolved in 30 ml DMPDA, and 1.8 ml (13.2 mmol) TEA was added under stirring. The reaction mixture was stirred overnight at room temperature. When the reaction was complete (TLC control), 2 ml DMPDA was added and allowed to stand for 1 h. Then 200 ml water and 200 ml diethyl ether were added to the solution. The precipitate was filtered off and washed with water and ether to yield 6.3 g (80%) of the product. M.p. 137-138° C., $[\alpha]^{21}_D$ −15.2° (c=1; DMFA).

c) The preparation of bis-(N$^\epsilon$-benzyloxycarbonyl-lysyl-γ-benzyl-glutamic acid) hexamethylenediamide, (H-Lys(Z)-Glu(OBzl)-NH)$_2$—(CH$_2$)$_6$ A solution of 6.3 g (5.0 mmol) (Boc-Lys(Z)-Glu(OBzl)-NH)$_2$—(CH$_2$)$_6$ in 70 ml TFA was allowed to stand for 1 h. The solvent was removed in vacuo, and the residue was triturated with diethyl ether. The crystallizing precipitate was filtered off to yield 6.2 g (95%) of the product. M.p. 172-174° C., $[\alpha]^{27}_D$ +3.6° (c=1; DMFA).

d) The preparation of bis-(N-acetyl-N$^\epsilon$-benzyloxycarbonyl-lysyl-γ-benzyl-glutamic acid) hexamethylenediamide, (CH$_3$CO-Lys(Z)-Glu(OBzl)-NH)$_2$—(CH$_2$)$_6$ 1.8 ml (12.7 mmol) TEA was added under stirring to a solution of 6.2 g (4.8 mmol) (H-Lys(Z)-Glu(OBzl)-NH)$_2$—(CH$_2$)$_6$ and 2.3 g (12.7 mmol) acetic acid p-nitrophenyl ester (AcONp) in 30 ml DMFA. The reaction mix was stirred at room temperature for 3 h. The product formed a precipitate in the course of the reaction (TLC control). Then 200 ml diethyl ether and 200 ml water were added to the reaction mixture. The precipitate was filtered off and dried in vacuo to yield 5.1 g (92%) of the product. M.p. 220-222° C., $[\alpha]^{21}_D$ −11.2° (c=1; DMFA).

e) The preparation of bis-(N-acetyl-lysyl-glutamic acid) hexamethylenediamide, (CH$_3$CO-Lys-Glu-NH)$_2$—(CH$_2$)$_6$ (GK-4)

5.1 g (4.4 mmol) (CH$_3$CO-Lys(Z)-Glu(OBzl)-NH)$_2$—(CH$_2$)$_6$ were dissolved in 150 ml methanol, then 3.0 g 10% Pd/C was added to the suspension and hydrogenated under stirring at 40° C. using 3 ml (59.9 mmol) conc. ammonium formate solution being added in portions. After stirring for 4 h, the catalyst was filtered off and washed with methanol, and the filtrate was evaporated. The resulting product was dissolved in 500 ml water and purified on a 100 ml SP-Sephadex column using a 0.1 to 0.2 M pyridine-acetate buffer gradient. The relevant fractions were collected (TLC control) and evaporated, and then re-evaporated with isopropanol. The residue was triturated with methanol, and the crystallizing solid precipitate was filtered off and dried in vacuo to yield 3.4 g (93%; total recovery 63%) of the product as white crystals. R$_f$ 0.30 (A), R$_f$ 0.20 (B); m.p. 205-206° C.; $[\alpha]^{27}_D$ −39.3° (c=1; water). C$_{32}$H$_{58}$N$_8$O$_{10}$.

$^1$H NMR (DMSO-d$_6$-CF$_3$COOD): 1.21 (4H, m, —NHCH$_2$CH$_2$CH$_2$CH$_2$CH$_2$CH$_2$NH—), 1.33 (8H, m, —NHCH$_2$CH$_2$CH$_2$CH$_2$CH$_2$CH$_2$NH—, 2C$^\gamma$H$_2$ Lys), 1.52 (4H, m, 2C$^\delta$H$_2$ Lys), 1.90 and 1.75 (4H, each m, 2C$^\beta$H$_2$ Glu), 1.85 (6H, s, 2CH$_3$CO—), 2.25 (4H, t, 2C$^\gamma$H$_2$ Glu), 2.74 (4H, m, 2C$^\epsilon$H$_2$ Lys), 3.02 (4H, m, —NHCH$_2$CH$_2$CH$_2$CH$_2$CH$_2$CH$_2$NH—), 4.17 (4H, m, 2C$^\alpha$H Lys, 2C$^\alpha$H Glu), 7.81 (2H, t, —NHCH$_2$CH$_2$CH$_2$CH$_2$CH$_2$CH$_2$NH—), 7.70 (6H, m, 2NH$_3^+$ Lys), 7.94 (2H, d, 2NH Glu), 8.11 (2H, d, 2NH Lys). The 2 COOH Glu signals are exchangeable with HDO.

Example 5

The synthesis of N-(6-aminocaproyl)-glycyl-lysine amide, H$_2$N(CH$_2$)$_5$CO-Gly-Lys-NH$_2$ (GK-5)

a) The preparation of N-benzyloxycarbonyl-glycyl-N$^\epsilon$-t-butyloxycarbonyl-lysine amide, Z-Gly-Lys(Boc)-NH$_2$ A solution of 7.0 g (14.6 mmol) N-benzyloxycarbonyl-N$^\epsilon$-t-butyloxycarbonyl-lysine N-oxysuccinimide ester (Z-Lys(Boc)-OSu) in 20 ml DMFA was treated with 5 ml ammonia for 10 min. Then 100 ml water with ice was added to the reaction mix. The precipitate was filtered off and washed with water. Thus 5.3 g (96%) of N-benzyloxycarbonyl-N$^\epsilon$-t-butyloxycarbonyl-lysine amide (Z-Lys(Boc)-NH$_2$) was obtained. The product was dissolved in methanol, and 3.0 g of 10% Pd/C was added to the suspension and hydrogenated under stirring at room temperature using 3 ml (59.9 mmol) conc. ammonium formate supplemented with a small amount of acetic acid. When the starting compound disappeared (TLC control), the catalyst was filtered off and washed with methanol, and the filtrate was evaporated. The residue was taken up in DMFA and 4.8 g (14.6 mmol) N-benzyloxycarbonyl-glycine p-nitrophenyl ester (Z-Gly-ONp) was added. The reaction mixture was stirred overnight at room temperature. When the reaction was complete (TLC control), 1 ml DMPDA was added and allowed to stand for 30 min. Then 300 ml ethyl acetate was added to the solution and washed successively with 200 ml water, 50 ml sat. NaCl, and 3% K$_2$CO$_3$ (3×150 ml). The ethyl acetate fraction was evaporated, and the residue was recrystallized from diethyl ether to yield 4.3 g (71%) of the product.

b) The preparation of N-t-butyloxycarbonyl-6-aminocaproic acid N-oxysuccinimide ester, Boc-NH(CH$_2$)$_5$CO—OSu 13.1 g (60.0 mmol) di-tert-butylpyrocarbonate was added to a solution of 7.0 g (53.4 mmol) 6-aminocaproic acid in 80 ml DMFA. The reaction mixture was stirred for 2 h at room temperature. The DMFA was removed in vacuo, the residue was dissolved in ethyl acetate and 6.9 g (60.0 mmol) N-hydroxysuccinimide and 12.4 g (60.0 mmol) DCCD were added. The reaction mixture was stirred overnight at room temperature. On the next day the precipitated dicyclohexylurea was filtered off, the solution was evaporated, and the residue was recrystallized from an isopropanol-hexane 1:1 mixture to yield 16.0 g (96%) of the product.

c) The preparation of N—(N-t-butyloxycarbonyl-6-aminocaproyl)glycyl-N$^\epsilon$-t-butyloxycarbonyl-lysine, Boc-NH(CH$_2$)$_5$CO-Gly-Lys(Boc)-NH$_2$ 4.3 g (10.0 mmol) Z-Gly-Lys(Boc)-NH$_2$ was hydrogenated in methanol using 3 ml (59.9 mmol) conc. ammonium formate solution supplemented with acetic acid. When the starting compound disappeared (TLC control), the catalyst was filtered off and washed with methanol, and the filtrate was evaporated. The residue was taken up in DMFA and 3.9 g (12.4 mmol) Boc-NH(CH$_2$)$_5$CO—OSu was added. The reaction mixture was stirred overnight at room temperature. When the reaction was complete (TLC control), 1 ml DMPDA was added and allowed to stand for 30 min. The reaction mixture was diluted with 200 ml ethyl acetate and 150 ml water, and the aqueous layer was extracted in 200 ml ethyl acetate. The ethyl acetate fraction was washed with 100 ml water, the solvent was evaporated, and 200 ml diethyl ether was added to the residue and allowed to crystallize in the cold. The precipitate was filtered off and washed with ether to yield 3.1 g (60%) of the product.

d) The preparation of N-(6-aminocaproyl)glycyl-lysine amide, H$_2$N(CH$_2$)$_5$CO-Gly-Lys-NH$_2$ 3.1 g (6.0 mmol) Boc-NH(CH$_2$)$_5$CO-Gly-Lys(Boc)-NH$_2$ were treated with 100 ml TFA for 1 h. The reaction mixture was then evaporated, and the residue was triturated with 200 ml diethyl ether. The ether was poured off, and the resulting product was dissolved in 500 ml water and purified on a 100 ml SP-Sephadex column using a 0.1 to 0.6 M pyridine-acetate buffer gradient. The relevant fractions (TLC control) were collected, evaporated and re-evaporated with isopropanol. The residue was dried in vacuo to yield 2.5 g (96%; total recovery 39%) of the product as a hygroscopic white solid. R$_f$ 0.65 (A), R$_f$ 0.51 (B); m.p. 50-52° C.; $[\alpha]^{25}_D$ −7.8° (c=0.17; water).

¹H NMR (DMSO-d₆-CF₃COOD): 1.27 and 1.47 (12H, m, —C$^\beta$H₂C$^\gamma$H₂C$^\delta$H₂— Lys, NH₂CH₂CH₂CH₂C H₂CH₂CO—), 2.12 (2H, t, NH₂CH₂CH₂CH₂CH₂C H₂CO—), 2.64 (4H, m, NH₂CH₂CH₂CH₂CH₂CH₂CO—, C$^\epsilon$H₂ Lys), 3.65 and 3.72 (2, 2dd, CH₂ Gly), 4.13 (1H, m, C$^\alpha$H Lys), 7.08 and 7.52 (2H, 2s, NH₂ amide), 8.11 (1H, d, NH Lys), 8.46 (1H, t, NH Gly). N$^\epsilon$H₂ Lys and N H₂CH₂CH₂CH₂CH₂CH₂CO— are exchangeable with HDO.

Example 6

The synthesis of bis-(N-(6-aminocaproyl)glycyl-lysine) hexamethylenediamide, (H₂N(CH₂)₅CO-Gly-Lys-NH)₂—(CH₂)₆ (GK-6)

a) The preparation of bis-(N-benzyloxycarbonyl-glycyl-N$^\epsilon$-t-butyloxycarbonyl-lysine) hexamethylenediamide, (Z-Gly-Lys(Boc)-NH)₂—(CH₂)₆

A solution of 7.2 g (15.0 mmol) N-benzyloxycarbonyl-N$^\epsilon$-t-butyloxycarbonyl-lysine N-oxysuccinimide ester (Z-Lys(Boc)-OSu) and 0.85 g (7.3 mmol) hexamethylenediamine in 20 ml DMFA was stirred overnight at room temperature. When the reaction was complete (TLC control), 1 ml DMPDA was added and allowed to stand for 30 min followed by the addition of 10 ml acetic acid. The product was then precipitated overnight at +5° C. by adding 150 ml water, whereby the resulting oil was gradually hardened. The precipitate was filtered off and washed with water. The product was dissolved in methanol, and 3.0 g of 10% Pd/C was added to the suspension and hydrogenated under stirring at room temperature using 3 ml (59.9 mmol) conc. ammonium formate solution supplemented with a small amount of acetic acid. When the starting compound disappeared (TLC control), the catalyst was filtered off and washed with methanol, and the filtrate was evaporated. The residue was taken up in DMFA and 5.0 g (15.0 mmol) N-benzyloxycarbonyl-glycine p-nitrophenyl ester (Z-Gly-ONp) was added. The reaction mix was stirred overnight at room temperature. When the reaction was complete (TLC control), 1 ml DMPDA was added and allowed to stand for 30 min. The reaction mixture was diluted with 300 ml ethyl acetate and washed successively with 200 ml water, 50 ml sat. NaCl, 200 ml 2% H₂SO₄, and 3% K₂CO₃ (3×150 ml). The ethyl acetate fraction was evaporated, and the residue was recrystallized from diethyl ether to yield 5.6 g (80%) of the product.

b) The preparation of bis-(N—(N-t-butyloxycarbonyl-6-aminocaproyl)glycyl-N$^\epsilon$-t-butyloxycarbonyl-lysine) hexamethylenediamide, Boc-NH(CH₂)₅CO-Gly-Lys(Boc)-NH)₂—(CH₂)₆

5.6 g (5.9 mmol) (Z-Gly-Lys(Boc)-NH)₂—(CH₂)₆ was hydrogenated in methanol under stirring at room temperature using 3 ml (59.9 mmol) conc. ammonium formate solution supplemented with 3.0 g of 10% Pd/C and a small amount of acetic acid. When the starting compound disappeared (TLC control), the catalyst was filtered off and washed with methanol, and the filtrate was evaporated. The residue was taken up in DMFA and 4.3 g (13.8 mmol) N-t-butyloxycarbonyl-6-aminocaproic acid N-oxysuccinimide ester (Boc-NH(CH₂)₅CO—OSu, for which the synthesis is described in Example 5, section b) was added. The reaction mix was stirred overnight at room temperature. When the reaction was complete (TLC control), 1 ml DMPDA was added and allowed to stand for 30 min. The reaction mixture was diluted with 200 ml ethyl acetate and 150 ml water, and the aqueous layer was extracted in 200 ml ethyl acetate. The ethyl acetate fraction was washed with 100 ml water, and the solvent was evaporated. 200 ml diethyl ether was added to the residue and allowed to crystallize overnight in the cold. The precipitate was filtered off and washed with ether to yield 6.2 g (95%) of the product.

c) The preparation of bis-(N-(6-aminocaproyl)glycyl-lysine) hexamethylenediamide, (H₂N(CH₂)₅CO-Gly-Lys-NH)₂—(CH₂)₆ (GK-6)

6.2 g (5.6 mmol) Boc-NH(CH₂)₅CO-Gly-Lys(Boc)-NH)₂—(CH₂)₆ were treated with 100 ml TFA for 1 h. The reaction mixture was then evaporated, and the residue was triturated with 200 ml diethyl ether. The ether was poured off, and the resulting product was dissolved in 500 ml water and purified on a 100 ml SP-Sephadex column using a 0.1 to 0.6 M pyridine-acetate buffer gradient. The relevant fractions (TLC control) were collected, evaporated and re-evaporated with isopropanol. The resulting residue was dried in vacuo and purified on a C8 reversed phase HPLC column using a 0 to 20% isopropanol gradient in 0.1M acetic acid. The fraction corresponding to the product was evaporated and dried in vacuo to yield 3.8 g (95%; total recovery 72%) of the final product as an oil. R$_f$ 0.50 (A), R$_f$ 0.08 (B); m.p. 50-52° C.; [α]$^{27}_D$ −129.6° (c=0.17; water).

¹H NMR (DMSO-d₆): 1.10-1.70 (32H, m, 2 —C$^\beta$H₂C$^\gamma$ H₂C$^\delta$H₂— Lys, 2 NH₂CH₂CH₂CH₂CH₂CH₂CO—, NHCH₂CH₂CH₂CH₂CH₂CH₂NH—), 2.12 (4H, t, 2 NH₂CH₂CH₂CH₂CH₂CH₂CO—), 2.65 (8H, m, 2 NHC H₂CH₂CH₂CH₂CH₂CO—, 2 C$^\epsilon$H₂ Lys), 3.01 (4H, m, —NHCH₂CH₂CH₂CH₂CH₂CH₂NH), 3.66 and 3.69 (4H, each dd, 2 CH₂ Gly), 4.14 (2H, m, 2 C$^\alpha$H, Lys), 8.09 (2H, t, NHCH₂CH₂CH₂CH₂CH₂CH₂NH—), 8.19 (2H, d, 2 NH Lys), 8.45 (2H, t, 2 NH Gly). 2 N$^\epsilon$H₂ Lys and 2 N H₂CH₂CH₂CH₂CH₂CH₂CO— are exchangeable with HDO.

Example 7

The synthesis of bis-(N-monosuccinyl-glutamyl-lysyl-6-aminohexanoic acid) trimethylenediamide, (HOOC(CH₂)₂CO-Glu-Lys-NH(CH₂)₅CO—NH)₂—(CH₂)₃ (GK-2a)

a) The preparation of succinic acid monobenzyl ester, HOOC(CH₂)₂CO—OBzl

A mixture of 10.00 g (100.00 mmol) succinic anhydride and 11 ml (101.70 mmol) benzyl alcohol was heated to reflux for 6 h. The reaction mixture was brought to room temperature and washed with diethyl ether. The ether solution was filtered from the insoluble succinic acid precipitate and washed with a sat. NaHCO₃ solution (3×40 ml). The aqueous layer containing HOOC(CH₂)₂CO—OBzl sodium salt was separated from the ether layer containing a side product of the reaction, succinic acid dibenzyl ester, insoluble in weakly basic aqueous media. The aqueous solution was acidified with 2N HCl, thereby precipitating a white crystalline mass. The precipitate was filtered off, washed with cold water and dried in vacuo to yield 10.00 g (48%) of a white crystalline product. M.p. 58-59° C. From the literature: m.p. 58-59° C. (J. Chem. Soc., 1955, 1097).

b) The preparation of monobenzylsuccinic acid succinimide ester, BzlO—OC(CH₂)₂CO—OSu 7.50 g (36.02 mmol) HOOC(CH₂)₂CO—OBzl and 4.17 g (36.20 mmol) N-hydroxy-succinimide were dissolved at room temperature in 70 ml THF. The resulting solution was cooled down to 0° C. A solution of 7.47 g (36.20 mmol) DCCD in 30 ml THF cooled to 0° C. was added thereto under vigorous stirring. The reaction mixture was stirred at 0° C. for 6 h. The white precipitate of dicyclohexylurea was filtered off. The solvent was removed in vacuo. The resulting viscous oily mass was dissolved in 50 ml methylene chloride, and the solution was allowed to stand at 0° C. for 24 h. The resulting precipitate was filtered off. The filtrate was evaporated in vacuo to yield 10.78 g (98%) of an oily, crystallizable product.

c) The preparation of glutamic acid γ-benzyl ester, H-Glu(OBzl)-OH

A mixture of 29.40 g (0.20 mol) glutamic acid, 82 ml (0.80 mol) benzyl alcohol and 41.85 g (0.22 mol) p-toluenesulfonic acid monohydrate was heated at 100-105° C. for 25 min under vigorous stirring until it was homogeneous and clear. The reaction mixture was allowed to cool down, and then 300 ml benzene was added. The resulting solution was washed with water (5×200 ml), and the aqueous phase containing the H-Glu(OBzl)-OH salt of p-toluenesulfonic acid and the unreacted glutamic acid was separated from the organic phase. To the resulting aqueous solution under stirring crystalline $NaHCO_3$ was added in small portions to bring the pH to 6. This brought about the formation of a white crystalline precipitate. The solution containing the precipitate was allowed to stand for a few hours at +5° C. The precipitate was then filtered off, washed several times with cold water and dried in vacuo to yield 12.00 g (30%) of the product. M.p. 169-170° C. From the literature: m.p. 169-170° C. (J. Chem. Soc., 1950, 3239).

d) The preparation of N-benzylsuccinyl-γ-benzyl-glutamic acid, BzlO—OC(CH$_2$)$_2$CO-Glu(OBzl)-OH 7.12 g (30.00 mmol) glutamic acid γ-benzyl ester (H-Glu(OBzl)-OH) was suspended in 50 ml DMFA. The resulting suspension was cooled down to 0° C., then under vigorous stirring a solution of 5.19 ml (30.00 mmol) DIEA in 10 ml DMFA was added followed by a solution of 9.16 g (30.00 mmol) BzlO—OC(CH$_2$)$_2$CO—OSu in 50 ml DMFA. The cooling was ceased after the resulting reaction mix became homogeneous. The reaction mixture was stirred for 18 h at room temperature. Then under vigorous stirring 400 ml of a cold 5% citric acid solution was added to the reaction mixture leading to the formation of a white finely dispersed crystal precipitate. The resulting suspension was washed with ethyl acetate (3×200 ml). The organic phases were combined, washed with 200 ml sat. NaCl and dried over anhydrous Na$_2$SO$_4$. The solvent was removed in vacuo to yield 11.94 g (93%) of a light-yellow oily product.

e) The preparation of N-benzylsuccinyl-γ-benzyl-glutamic acid N-oxysuccinimide ester, BzlO—OC(CH$_2$)$_2$CO-Glu(OBzl)-OSu 11.81 g (27.63 mmol) BzlO—OC(CH$_2$)$_2$CO-Glu(OBzl)-OH and 3.44 g (29.93 mmol) N-hydroxysuccinimide were dissolved at room temperature in 60 ml THF. The solution was cooled down to 0° C. To this solution under vigorous stirring a solution of 6.18 g (29.93 mmol) DCCD in 20 ml THF cooled to 0° C. was added. The reaction mixture was stirred at 0° C. for 24 h. The white precipitate of dicyclohexylurea was filtered off. The solvent was removed in vacuo. The resulting viscous oily mass was dissolved in 35 ml methylene chloride. The solution was allowed to stand at 0° C. for 24 h. The resulting precipitate was filtered off, and the filtrate was evaporated in vacuo to yield 14.06 g (97%) of an oily product.

f) The preparation of N-t-butyloxycarbonyl-N$^\epsilon$-(2-chlorobenzyloxycarbonyl)lysine N-oxysuccinimide ester, Boc-Lys(2-Cl—Z)—OSu 6.00 g (14.46 mmol) N-t-butyloxycarbonyl-N$^\epsilon$-(2-chlorobenzyloxycarbonyl)lysine (Boc-Lys(2-Cl—Z)—OSu) and 1.83 g (15.91 mmol) N-hydroxysuccinimide were dissolved at room temperature in 35 ml THF. The solution was cooled down to 0° C. To this solution under vigorous stirring a solution of 3.28 g (15.91 mmol) DCCD in 10 ml THF cooled to 0° C. was added. The reaction mixture was stirred at 0° C. for 24 h. The white precipitate of dicyclohexylurea was filtered off. The solvent was removed in vacuo. The resulting viscous oily mass was dissolved in 20 ml methylene chloride. The solution was allowed to stand at 0° C. for 24 h. The resulting precipitate was filtered off, and the filtrate was evaporated in vacuo to yield 6.90 g (93%) of an oily product.

g) The preparation of N-t-butyloxycarbonyl-N$^\epsilon$-(2-chlorobenzyloxycarbonyl)lysyl-6-aminohexanoic acid, Boc-Lys(2-Cl—Z)—NH(CH$_2$)$_5$COOH 1.58 g (12.05 mmol) 6-aminohexanoic acid was suspended in 10 ml water. To the suspension 4.8 ml 2N NaOH, 1.01 g (12.05 mmol) NaHCO$_3$ and 12 ml DMFA were added at room temperature under stirring. The resulting suspension was cooled down to 0° C. and a solution of 6.17 g (12.05 mmol) Boc-Lys(2-Cl—Z)—OSu in 12 ml DMFA was added under vigorous stirring. The reaction mixture was stirred for 1 h at 0° C. followed by the addition of 24 ml DMFA-H$_2$O 1:1 mixture. The reaction mixture was gradually brought to room temperature followed by stirring for 24 h. Then 150 ml of a cold 5% citric acid solution was added under vigorous stirring. The reaction mixture was washed with ethyl acetate (3×50 ml). The combined ethyl acetate phases were washed with sat. NaCl (3×50 ml) and dried over anhydrous Na$_2$SO$_4$. The solvent was removed in vacuo to yield 5.97 g (94%) of a light-yellow oily product.

g) The preparation of N$^{\epsilon\text{-}}$(2-chlorobenzyloxycarbonyl)lysyl-6-aminohexanoic acid, Lys(2-Cl—Z)—NH(CH$_2$)$_5$COOH 5.96 g (11.29 mmol) Boc-Lys(2-Cl—Z)—NH(CH$_2$)$_5$COOH was added under stirring to 50 ml 4M HCl/dioxane at room temperature. The reaction mix was stirred for 2 h at room temperature. The solvent was then removed in vacuo at 25-30° C. The oily residue was washed with methylene chloride. The insoluble oily mass was gradually undergoing crystallization that resulted in the formation of a white crystalline precipitate which was filtered off, washed several times with methylene chloride and dried in vacuo to yield 3.72 g (71%) of a white crystalline product.

h) The preparation of N-benzylsuccinyl-γ-benzyl-glutamyl-N$^\epsilon$-(2-chlorobenzyl-oxycarbonyl)lysyl-6-aminohexanoic acid, BzlO—OC(CH$_2$)$_2$CO-Glu(OBzl)-Lys(2-Cl—Z)—NH(CH$_2$)$_5$COOH 3.70 g (7.97 mmol) Lys(2-Cl—Z)—NH(CH$_2$)$_5$COOH was dissolved in 15 ml DMFA. The solution was cooled down to 5° C. A solution of 1.8 ml (15.94 mmol) N-methylmorpholine in 5 ml DMFA and a solution of 4.18 g (7.97 mmol) BzlO—OC(CH$_2$)$_2$CO-Glu(OBzl)-OSu in 15 ml DMFA were added thereto. The reaction mixture was stirred for 2 days at room temperature. The precipitate was filtered off, and the solvent was removed in vacuo at 25-30° C. To the residue 50 ml of a cold 10% citric acid solution and 100 ml ethyl acetate were added. The ethyl acetate layer was separated from the aqueous layer which was additionally washed with ethyl acetate (3×50 ml). The combined organic phases were washed with sat. NaCl (2×50 ml) and dried over anhydrous Na$_2$SO$_4$. The solvent was removed in vacuo. The residue was triturated with diethyl ether at room temperature leading to the crystallization of the product. The resulting crystals were washed with ether and dried in vacuo to yield 4.81 g (72%) of a crystalline product.

i) The preparation of N-benzylsuccinyl-γ-benzyl-glutamyl-N$^\epsilon$-(2-chlorobenzyl-oxycarbonyl)lysyl-6-aminohexanoic acid N-oxysuccinimide ester, BzlO—OC(CH$_2$)$_2$CO-Glu(OBzl)-Lys(2-Cl—Z)—NH(CH$_2$)$_5$CO—OSu 4.80 g (5.73 mmol) BzlO—OC(CH$_2$)$_2$CO-Glu(OBzl)-Lys(2-Cl—Z)—NH(CH$_2$)$_5$COOH and 0.73 g (6.30 mmol) N-hydroxysuccinimide were dissolved at room temperature in 35 ml THF. To this solution under vigorous stirring a solution of 1.30 g (6.30 mmol) DCCD in 5 ml THF was added. The reaction mixture was stirred at room temperature for 36 h. The white precipitate of dicyclohexylurea was filtered off. The solvent was removed in vacuo. The resulting viscous crystalline mass was dissolved in 30 ml methylene chloride. The solution was allowed to stand at 0° C. for 24 h. The resulting precipitate was filtered off, and the filtrate was dried in vacuo to yield 5.35 g (100%) of the product as a viscous crystalline mass.

j) The preparation of bis-(N-benzylsuccinyl-γ-benzyl-glutamyl-N$^\epsilon$-(2-chlorobenzyloxycarbonyl)lysyl-6-aminohexanoic acid) trimethylenediamide, (BzlO—OC(CH$_2$)$_2$CO-Glu(OBzl)-Lys(2-Cl—Z)—NH(CH$_2$)CO—NH)$_2$—(CH$_2$)$_3$ To a solution of 0.2 ml (2.85 mmol) propylenediamine in 15 ml DMFA cooled down to 0° C. under nitrogen first a solution of 1 ml (5.70 mmol) DIEA in 5 ml DMFA and then a cold solution of 5.33 g (5.70 mmol) BzlO—OC(CH$_2$)$_2$CO-Glu(OBzl)-Lys(2-Cl—Z)—NH(CH$_2$)$_5$CO—OSu in 30 ml DMFA were added under stirring. The reaction mixture was stirred for 1 h at 0° C. and for a further 24 h at room temperature. The solvent was removed in vacuo at 25-30° C. To the oily residue under vigorous stirring 50 ml of a cold 10% citric acid solution was added. The crystalline precipitate was filtered off and washed successively with 50 ml 5% NaHCO$_3$, water (2×50 ml), acetone (2×50 ml), ethyl acetate (2×50 ml), and diethyl ether followed by drying in vacuo to yield 3.08 g (63%) of a white crystalline product.

k) The preparation of bis-(N-monosuccinyl-glutamyl-lysyl-6-aminohexanoic acid) trimethylenediamide, (HOOC(CH$_2$)$_2$CO-Glu-Lys-NH(CH$_2$)$_5$CO—NH)$_2$—(CH$_2$)$_3$ (GK-2a)

2.50 g (1.46 mmol) (BzlO—OC(CH$_2$)$_2$CO-Glu(OBzl)-Lys(2-Cl—Z)—NH(CH$_2$)$_5$CO—NH)$_2$—(CH$_2$)$_3$ was dissolved at room temperature in 30 ml ethanol, then 5 ml cyclohexene was added followed by a careful addition of 1.0 g 10% Pd/C under stirring. The resulting suspension was heated to reflux under stirring and continued for 5 h. The reaction mixture was cooled to room temperature, and the catalyst was filtered off. The solvent was evaporated, and the residue was washed with hexane and diethyl ether followed by drying in vacuo to yield 1.38 g (93%; total recovery 42%) of the final product as white crystals. R$_f$ 0.41 (A), R$_f$ 0.20 (B); m.p. 118-121° C.; [α]$^{25}_D$ −30.0° (c=1; water).

$^1$H NMR (DMSO-d$_6$): 1.09-1.96 (26H, m, 2 —C$^\beta$H$_2$C$^\gamma$H$_2$C$^\delta$H$_2$— Lys, 2 NHCH$_2$CH$_2$CH$_2$CH$_2$CH$_2$CO—, NHCH$_2$CH$_2$CH$_2$NH—), 1.74 and 1.89 (4H, each m, C$^\beta$H$_2$ Glu), 2.03 (4H, t, 2 NHCH$_2$CH$_2$CH$_2$CH$_2$CH$_2$CO—), 2.26 (4H, m, 2C$^\gamma$H$_2$ Glu), 2.39 (8H, m, 2 HOOCCH$_2$CH$_2$CO—), 2.74 (4H, m, 2 C$^\epsilon$H$_2$ Lys), 3.00 (8H, m, 2 —NHCH$_2$CH$_2$CH$_2$CH$_2$CH$_2$CO—, —NHCH$_2$CH$_2$CH$_2$CO—), 4.10 (2H, m, 2 C$^\alpha$H Lys), 4.16 (2H, m, 2 C$^\alpha$H Glu), 7.74 (2H, t, —NHCH$_2$CH$_2$CH$_2$NH—), 7.84 (2H, t, 2 —NHCH$_2$CH$_2$CH$_2$CH$_2$CH$_2$CO—), 7.94 (2H, d, 2 NH Lys), 8.22 (2H, d, 2 NH Glu). 2 HOOC(CH$_2$)$_2$CO—, 2 —COOH Glu and 2 —N$^\epsilon$H$_2$ Lys are exchangeable with HDO.

Example 8

The synthesis of bis-(N-monosuccinyl-glutamyl-lysine)pentamethylenediamide (GK-2b), bis-(N-monosuccinyl-glutamyl-lysine)tetramethylenediamide (GK-2c), bis-(N-monosuccinyl-glutamyl-lysine)trimethylenediamide (GK-2d), and bis-(N-monosuccinyl-glutamyl-lysine)ethylenediamide (GK-2e), (HOOC(CH$_2$)$_2$CO-Glu-Lys-NH)$_2$—(CH$_2$)$_n$, where n=2, 3, 4, 5 a) The preparation of N-monobenzylsuccinyl-γ-benzyl-glutamyl-N$^\epsilon$-(2-chlorobenzyloxycarbonyl)lysine, BzlO—OC(CH$_2$)$_2$CO-Glu(OBzl)-Lys(2-Cl—Z)—OH To a solution of 6.55 g (18.65 mmol) N$^\epsilon$-(2-chlorobenzyloxycarbonyl)lysine hydrochloride (H-Lys(2-Cl—Z)—OH.HCl) in 35 ml DMFA at +5° C. a solution of 4.1 ml (37.30 mmol) N-methylmorpholine in 10 ml DMFA and a solution 9.78 g (18.65 mmol) BzlO—OC(CH$_2$)$_2$CO-Glu(OBzl)-OSu (for which the synthesis is described in Example 7, section e) in 35 ml DMFA were added. The reaction mixture was stirred for 2 days at room temperature. The precipitate was filtered off, and the solvent was removed in vacuo. To the residue 100 ml of a cold 10% citric acid solution and 200 ml ethyl acetate were added. The ethyl acetate layer was separated from the aqueous layer which was additionally washed with ethyl acetate (3×100 ml). The combined organic phases were washed with sat. NaCl (2×50 ml), dried over anhydrous Na$_2$SO$_4$ and evaporated. The residue was triturated with diethyl ether at room temperature leading to the crystallization of the product. The resulting crystals were washed with ether and dried in vacuo to yield 12.43 g (92%) of a light-yellow crystalline product. M.p. 80-82° C.

b) The preparation of N-monobenzylsuccinyl-γ-benzyl-glutamyl-N$^\epsilon$-(2-chlorobenzyloxycarbonyl)lysine succinimide ester, BzlO—OC(CH$_2$)$_2$CO-Glu(OBzl)-Lys(2-Cl—Z)—OSu To a solution of 11.30 g (15.60 mmol) BzlO—OC(CH$_2$)$_2$CO-Glu(OBzl)-Lys(2-Cl—Z)—OH and 1.98 g (17.16 mmol) N-hydroxysuccinimide in 100 ml THF cooled down to 0° C. under vigorous stirring a solution of 3.54 g (17.16 mmol) DCCD in 20 ml THF also cooled down to 0° C. was added. The reaction mixture was stirred at 0° C. for 36 h. The white precipitate of dicyclohexylurea was filtered off. The solvent was removed in vacuo. The resulting viscous crystalline mass was dissolved in 30 ml methylene chloride, and the solution was allowed to stand at 0° C. for 24 h. The resulting precipitate was filtered off. The solvent was evaporated, and the residue was dried in vacuo to yield 12.80 g (100%) of the product as a viscous crystalline mass.

c) The preparation of bis-(N-benzylsuccinyl-γ-benzyl-glutamyl-N$^\epsilon$-(2-chlorobenzyloxycarbonyl)lysine)pentamethylenediamide, (BzlO—OC(CH$_2$)$_2$CO-Glu(OBzl)-Lys(2-Cl—Z)—NH)$_2$—(CH$_2$)$_5$ To a solution of 228 mg (1.95 mmol) pentamethylenediamine in 10 ml DMFA cooled down to 0° C. under nitrogen first a solution of 429 µl (3.90 mmol) N-methylmorpholine in 5 ml DMFA and then a cold solution of 3.20 g (3.90 mmol) BzlO—OC(CH$_2$)$_2$CO-Glu(OBzl)-Lys(2-Cl—Z)—OSu in 15 ml DMFA were added under stirring. The reaction mixture was stirred for 1 h at 0° C. and for a further 24 h at room temperature. The solvent was removed in vacuo at 25-30° C. To the oily residue under vigorous stirring 50 ml of a cold 10% citric acid solution was added. The precipitated crystals were filtered off and washed successively with 50 ml 5% NaHCO$_3$, water (2×50 ml), acetone (2×50 ml), ethyl acetate (2×50 ml), and diethyl ether followed by drying in vacuo to yield 1.71 g (51%) of a white crystalline product.

$^1$H NMR (DMSO-d$_6$): 1.10-1.46 (14H, m, 2C$^\gamma$H$_2$C$^\delta$H$_2$ Lys, NHCH$_2$CH$_2$CH$_2$CH$_2$CH$_2$NH), 1.48 and 1.60 (4H, 2m, 2C$^\beta$H$_2$ Lys), 1.76 and 1.92 (4H, 2m, 2 C$^\beta$H$_2$ Glu), 2.38 (4H, m, 2C$^\gamma$H$_2$ Glu), 2.49 and 2.54 (8H, 2m, 2COCH$_2$CH$_2$CO), 2.96 (8H, m, 2C$^\epsilon$H Lys, NHCH$_2$CH$_2$CH$_2$CH$_2$CH$_2$NH), 4.12 (2H, m, 2C$^\alpha$H$_2$ Lys), 4.26 (2H, m, 2C$^\alpha$H Glu), 5.04 (4H, s, 2OCH$_2$C$_6$H$_5$ Lys), 5.07 (8H, s, 2OCH$_2$C$_6$H$_5$ Glu, 2C$_6$H$_5$CH$_2$OOCCH$_2$CH$_2$CO), 7.25-7.48 (28H, m, 4C$_6$H$_5$, 2C$_6$H$_4$Cl), 7.43 (2H, t, 2N$^\epsilon$H Lys), 7.74 (2H, t, NHCH$_2$CH$_2$CH$_2$CH$_2$CH$_2$NH), 7.83 (2H, d, 2NH Lys), 8.15 (2H, d, 2NH Glu).

d) The preparation of bis-(N-monosuccinyl-glutamyl-lysine)pentamethylenediamide, (HOOC(CH$_2$)$_2$CO-Glu-Lys-NH)$_2$—(CH$_2$)$_5$ (GK-2b)

1.65 g (0.97 mmol) (HOOC(CH$_2$)$_2$CO-Glu(OBzl)-Lys(2-Cl—Z)—NH)$_2$—(CH$_2$)$_6$ was dissolved at room temperature in 30 ml ethanol, then 5 ml cyclohexene was added followed by a careful addition of 1.0 g 10% Pd/C under stirring. The resulting suspension was heated to reflux under stirring and continued for 5 h. The reaction mixture was cooled to room temperature, and the catalyst was filtered off. The solvent was evaporated, and the residue was washed with hexane and diethyl ether followed by drying in vacuo to yield 777 mg (98%; total recovery 40%) of a greenish efflorescent solid. R$_f$ 0.41 (A), R$_f$ 0.20 (B); [α]$^{25}_D$ −35.2° (c=0.5; water-methanol 1:1).

$^1$H NMR (DMSO-d$_6$): 1.10-1.70 (18H, m, 2C$^\beta$H$_2$C$^\gamma$H$_2$C$^\delta$H$_2$ Lys, —NHCH$_2$CH$_2$CH$_2$CH$_2$CH$_2$NH—), 1.73 and 1.88 (2H, each m, 2C$^\beta$H$_2$ Glu), 2.26 (4H, m, 2C$^\gamma$H$_2$ Glu), 2.40 (8H, m, 2HOOCCH$_2$CH$_2$CO—), 2.74 (4H, m, 2C$^\epsilon$H$_2$ Lys), 3.00 (4H, m, —NHCH$_2$CH$_2$CH$_2$CH$_2$CH$_2$NH—), 4.08 (2H, m, 2C$^\alpha$H Lys), 4.18 (2H, m, 2C$^\alpha$H Glu), 7.73 (4H, t, —NHCH$_2$CH$_2$CH$_2$CH$_2$CH$_2$NH—), 7.95 (2H, d, 2NH Lys), 8.26 (2H, d, 2NH Glu). 2HOOC(CH$_2$)$_2$CO— and 2 —COOH Glu are exchangeable with HDO.

For the synthesis of GK-2c, GK-2d, and GK-2e, 3.20 g (3.90 mmol) BzlO—OC(CH$_2$)$_2$CO-Glu(OBzl)-Lys(2-Cl—Z)—OSu and 1.95 mmol tetramethylenediamine, propylenediamine, and ethylenediamine each were used per synthesis, respectively. All the compounds were synthetized according to the protocol disclosed for GK-2b.

Bis-(N-monosuccinyl-glutamyl-lysine)tetramethylenediamide (HOOC(CH$_2$)$_2$CO-Glu-Lys-NH)$_2$—(CH$_2$)$_4$ (GK-2c)

A white efflorescent solid. R$_f$ 0.41 (A), R$_f$ 0.20 (B); [α]$^{25}_D$ −33.3° (c=1.0; water).

$^1$H NMR (DMSO-d$_6$): 1.10-1.70 (16H, m, −2 —C$^\beta$H$_2$C$^\gamma$H$_2$C$^\delta$H$_2$— Lys, —NHCH$_2$CH$_2$CH$_2$CH$_2$NH—), 1.73 and 1.89 (4H, each m, 2C$^\beta$H$_2$ Glu), 2.26 (4H, m 2C$^\gamma$H$_2$ Glu), 2.40 (8H, m, 2HOOCCH$_2$CH$_2$CO—), 2.74 (4H, m, 2C$^\epsilon$H$_2$ Lys), 3.02 (4H, m, —NHCH$_2$CH$_2$CH$_2$CH$_2$NH), 4.09 (2H, m, 2C$^\alpha$H Lys), 4.18 (2H, m, 2C$^\alpha$H Glu), 7.80 (2H, t, —NHCH$_2$CH$_2$CH$_2$CH$_2$NH—), 7.93 (2H, d, 2NH Lys), 8.21 (2H, d, 2NH Glu). 2 HOOC(CH$_2$)$_2$CO—, 2 —COOH and 2 —N$^\epsilon$H$_2$ Lys are exchangeable with HDO.

Bis-(N-monosuccinyl-glutamyl-lysine)trimethylenediamide (HOOC(CH$_2$)$_2$CO-Glu-Lys-NH)$_2$—(CH$_2$)$_3$ (GK-2d)

A white efflorescent solid. R$_f$ 0.41 (A), R$_f$ 0.20 (B); [α]$^{25}_D$ −35.2° (c=0.5; water-methanol 1:1).

$^1$H NMR (DMSO-d$_6$): 1.11-1.70 (14H, m, 2 —C$^\beta$H$_2$C$^\gamma$H$_2$C$^\delta$H$_2$— Lys, —NHCH$_2$CH$_2$CH$_2$NH—), 1.75 and 1.88 (4H, each m, 2C$^\beta$H$_2$ Glu), 2.26 (4H, m, 2C$^\gamma$H$_2$ Glu), 2.39 (8H, m, 2 HOOCCH$_2$CH$_2$CO—), 2.75 (4H, m, 2C$^\epsilon$H$_2$ Lys), 3.02 (4H, m, —NHCH$_2$CH$_2$CH$_2$NH—), 4.11 (2H, m, 2C$^\alpha$H Lys), 4.15 (2H, m, 2C$^\alpha$H Glu), 7.84 (2H, t, —NHCH$_2$CH$_2$CH$_2$NH—), 7.96 (2H, d, 2NH Lys), 8.25 (2H, d, 2NH Glu). 2 HOOC(CH$_2$)$_2$CO—, 2 —COOH and 2 N$^\epsilon$H$_2$ Lys are exchangeable with HDO.

Bis-(N-monosuccinyl-glutamyl-lysine)ethylenediamide (HOOC(CH$_2$)$_2$CO-Glu-Lys-NH)$_2$—(CH$_2$)$_2$ (GK-2e)

A grey efflorescent solid. R$_f$ 0.41 (A), R$_f$ 0.20 (B); [α]$^{25}_D$ −31.6° (c=0.5; water-methanol 1:1).

$^1$H NMR (DMSO-d$_6$): 1.10-1.70 (12 H, m, 2 —C$^\beta$H$_2$C$^\gamma$H$_2$C$^\delta$H$_2$— Lys), 1.73 and 1.88 (4H, each m, 2C$^\beta$H$_2$ Glu), 2.26 (4H, m, C$^\gamma$H$_2$ Glu), 2.39 (8H, m, 2HOOCCH$_2$CH$_2$CO—), 2.75 (4H, m, 2C$^\epsilon$H$_2$ Lys), 3.10 (4H, m, —NHCH$_2$CH$_2$NH—), 4.11 (2H, m, C$^\alpha$H Lys), 4.18 (2H, m, 2C$^\alpha$H Glu), 7.84 (2H, t, —NHCH$_2$CH$_2$NH—), 7.96 (2H, d, 2NH Lys), 8.24 (2H, d, 2NH Glu). 2 HOOCCH$_2$CH$_2$CO—, 2 —COOH and 2 —N$^\epsilon$H$_2$ Lys are exchangeable with HDO.

Example 9

The synthesis of N-acetyl-glycyl-lysyl-γ-aminobutyric acid, CH$_3$CO-Gly-Lys-NH(CH$_2$)$_3$COOH (GK-7)

a) The preparation of γ-aminobutyric acid benzyl ester tosylate, H—NH(CH$_2$)$_3$CO—OBz.TsOH A solution of 10.32 g (0.10 mol) γ-aminobutyric acid, 20.93 g (0.11 mol) p-toluenesulfonic acid monohydrate and 50 ml (0.48 mol) benzyl alcohol in 100 ml benzene was heated to reflux under stirring for 5 h until there was no further water release, with a total water release of ~4 ml (a Dean-Stark nozzle was used). The solution was cooled and 200 ml diethyl ether was added leading to the formation of a precipitate. The mixture was allowed to stand overnight at +5° C. The precipitated crystals were filtered off from the stock solution and washed with diethyl ether (2×200 ml). The precipitate was dissolved in 500 ml boiling ethyl acetate. The resulting hot solution was allowed to cool for 4 h at room temperature and to stand overnight at +5° C. The precipitated crystals were filtered off and washed with 200 ml cold ethyl acetate and 200 ml diethyl ether. Drying in vacuo at 40° C. yielded 35.85 g (98%) of the product in the form of crystals. M.p. 105° C.

$^1$H NMR (DMSO-d$_6$): 1.80 (2H, m, —NHCH$_2$CH$_2$CH$_2$CO—), 2.28 (3H, s, —CH$_3$ TsOH), 2.48 (2H, t, —NHCH$_2$CH$_2$CH$_2$CO—), 2.82 (2H, m, —NHCH$_2$CH$_2$CH$_2$CO—), 5.10 (2H, s, —OCH$_2$C$_6$H$_5$), 7.12 and 7.49 (4H, m, C$_6$H$_4$-TsOH), 7.36 (5H, m, —OCH$_2$C$_6$H$_5$), 7.67 (3H, br. s, NH$_3^+$).

b) The preparation of N-t-butyloxycarbonyl-glycine pentafluorophenyl ester, Boc-Gly-OPfp To a solution of 17.52 g (0.10 mol) Boc-Gly-OH and 20.25 g (0.11 mol) pentafluorophenol in 250 ml THF cooled down to 0° C. under stirring a solution of 21.70 g (0.11 mol)

DCCD in 50 ml THF was added dropwise within 10 min. The solution was stirred overnight in an ice bath. The white precipitate of dicyclohexylurea was filtered off and washed with THF (2×100 ml). The combined filtrate was evaporated, and the residue was dissolved in 150 ml diethyl ether. The solution was allowed to stand at +4° C. for 4 h and filtered again to remove traces of the dicyclohexylurea precipitate followed by evaporation to a state of fluid oil. The residue was dissolved in 300 ml boiling hexane, and the resulting solution was allowed to stand for 2 h at room temperature and further at +5° C. overnight. The precipitated crystals were filtered off, washed with cold hexane (2×150 ml) and dried in vacuo at 50° C. for 4 h to yield 35.53 g (92%) of the product.

$^1$H NMR (DMSO-$d_6$): 1.37 and 1.40 (9H, 2s, ($CH_3$)$_3$CO—), 4.12 and 4.15 (2H, 2d, $CH_2$ Gly), 7.17 and 7.56 (1H, 2t, NH Gly).

c) The preparation of N-t-butyloxycarbonyl-N$^\epsilon$-benzyloxycarbonyl-lysine pentafluorophenyl ester, Boc-Lys(Z)—OPfp The preparation was similar to that of Boc-Gly-OPfp (Example 9, section b). 38.04 g (0.10 mol) Boc-Lys(Z)—OH and 20.25 g (0.11 mol) pentafluorophenol yielded 51.92 g (95%) of the product. M.p. 76-77° C.

d) The preparation of N-t-butyloxycarbonyl-N$^\epsilon$-benzyloxycarbonyl-lysyl-γ-aminobutyric acid benzyl ester, Boc-Lys(Z)—NH($CH_2$)$_3$CO—OBzl To a solution of 8.75 g (16.02 mmol) Boc-Lys(Z)—OPfp and 6.29 g (17.20 mmol) H—NH($CH_2$)$_3$CO—OBz.TsOH in 70 ml DMFA under stirring 2.5 ml (14.30 mmol) DIEA was added dropwise within 5 min. The reaction mixture was stirred at room temperature for 3 h. Then the solution was transferred to a separating funnel and 300 ml water, 100 ml ethyl acetate and 50 ml diethyl ether were added. Following the extraction the organic layer was separated, washed with 5% $H_2SO_4$, sat. $Na_2SO_4$, 5% $NaHCO_3$, and sat. $Na_2SO_4$, dried over anhydrous $Na_2SO_4$ and evaporated. The resulting oil was crystallized within 2 days. The crystals were washed with hexane (2×100 ml) and dried in vacuo to yield 8.10 g (91%) of the product. M.p. 77° C.

$^1$H NMR (DMSO-$d_6$): 1.10-1.57 (6H, m, —C$^\beta$$\underline{H}_2$C$^\gamma$$\underline{H}_2$C$^\delta$$\underline{H}_2$— Lys), 1.66 (2H, m, —NHCH$_2$C$\underline{H}_2$CH$_2$CO—), 2.35 (2H, t, —NHCH$_2$CH$_2$C$\underline{H}_2$CO—), 2.96 (2H, m, C$^\epsilon$$\underline{H}_2$ Lys), 3.07 (2H, m, —NHC$\underline{H}_2$CH$_2$CH$_2$CO—), 3.78 (1H, m, C$^\alpha$H Lys), 4.99 (2H, s, —CO—OC$\underline{H}_2$C$_6$H$_5$ Lys(Z)), 5.07 (2H, s, —OCH$_2$C$_6$H$_5$), 6.76 (1H, d, NH Lys), 7.21 (1H, t, N$^\epsilon$H Lys), 7.34 (10H, m, —CO—OCH$_2$C$_6$$\underline{H}_5$ Lys(Z), —OCH$_2$C$_6$$\underline{H}_5$), 7.80 (1H, t, —N$\underline{H}$CH$_2$CH$_2$CH$_2$CO—).

e) The preparation of N$^\epsilon$-benzyloxycarbonyl-lysyl-γ-aminobutyric acid benzyl ester hydrochloride, Lys(Z)—NH($CH_2$)$_3$CO—OBzl.HCl 20 ml 4M HCl/dioxane was added to a solution of 3.23 g (5.80 mmol) Boc-Lys(Z)—NH($CH_2$)$_3$CO—OBzl in 5 ml dioxane. At 30 min the reaction mix was evaporated in vacuo, and the residue was triturated with 70 ml diethyl ether. The resulting mixture was allowed to stand at +4° C. for 4 h, and the crystalline precipitate was filtered off, washed with cold diethyl ether (2×50 ml) and dried in vacuo at 50° C. for 3 h to yield 2.84 g (99%) of the product. M.p. 113-114° C.

$^1$H NMR (DMSO-$d_6$): 1.25 (2H, m, C$^\gamma$$\underline{H}_2$ Lys), 1.39 (2H, m, C$^\delta$$\underline{H}_2$ Lys), 1.70 (4H, m, C$^\beta$$\underline{H}_2$ Lys, —NHCH$_2$C$\underline{H}_2$CH$_2$CO—), 2.40 (2H, t, —NHCH$_2$CH$_2$C$\underline{H}_2$CO—), 2.96 (2H, m, C$^\epsilon$$\underline{H}_2$ Lys), 3.13 (2H, m, —NHC$\underline{H}_2$CH$_2$CH$_2$CO—), 3.66 (1H, m, C$^\alpha$H Lys), 5.00 and 5.08 (4H, 2s, —C$\underline{H}_2$C$_6$H$_5$), 7.23 (1H, t, N$^\epsilon$H Lys), 7.35 (10H, m, —CO—OCH$_2$C$_6$$\underline{H}_5$ Lys(Z), —OCH$_2$C$_6$$\underline{H}_5$), 8.17 (3H, m, $NH_3^+$ Lys), 8.55 (1H, t, N$\underline{H}$CH$_2$CH$_2$CH$_2$CO—).

f) The preparation of glycyl-N$^\epsilon$-benzyloxycarbonyl-lysyl-γ-aminobutyric acid benzyl ester trifluoroacetate, H-Gly-Lys(Z)—NH($CH_2$)$_3$CO—OBzl.TFA 1.48 ml (8.00 mmol) DIEA was added to a solution of 2.05 g (6.00 mmol) Boc-Gly-OPfp and 2.73 g (5.55 mmol) Lys(Z)—NH($CH_2$)$_3$CO—OBzl.HCl in 30 ml THF and 15 ml DMFA. The reaction mixture was stirred at room temperature for 4 h. To this solution 0.2 ml (2.00 mmol) N,N-dimethylethylenediamine was added, stirred for a further 20 min and concentrated by half. The reaction mix was transferred to a separating funnel and 100 ml water and 100 ml ethyl acetate were added. When the extraction was complete, the organic layer was separated and washed successively with 5% $H_2SO_4$, sat. $Na_2SO_4$, 5% $NaHCO_3$, and sat. $Na_2SO_4$, then it was dried over anhydrous $Na_2SO_4$ and evaporated. The solidified amorphous mass was taken up in 50 ml TFA. At 30 min the solution was evaporated, and the residue was triturated with 50 ml diethyl ether. The resulting mixture was allowed to stand at +5° C. for 4 h, and the crystalline precipitate was filtered off, washed with cold diethyl ether (2×50 ml) and dried in vacuo at 50° C. for 3 h to yield 3.24 g (93%) of the product.

g) The preparation of N-acetyl-glycyl-N$^\epsilon$-benzyloxycarbonyl-lysyl-γ-aminobutyric acid benzyl ester, $CH_3$CO-Gly-Lys(Z)—NH($CH_2$)$_3$CO—OBzl 0.4 ml (4.00 mmol) acetic anhydride was added to a solution of 0.50 g (4.34 mmol) N-hydroxysuccinimide in 10 ml THF followed by stirring for 2 h. To this solution 10 ml DMFA was added followed by 1.68 g (2.68 mmol) H-Gly-Lys(Z)—NH($CH_2$)$_3$CO—OBzl.TFA and 1 ml (5.70 mmol) DIEA. The reaction mixture was stirred for 2 h, then transferred to a separating funnel and 100 ml water and 100 ml ethyl acetate were added. When the extraction was complete, the organic layer was separated and washed successively with 5% $H_2SO_4$, sat. $Na_2SO_4$, 5% $NaHCO_3$, and sat. $Na_2SO_4$, then it was dried over anhydrous $Na_2SO_4$ and evaporated. The residue was taken up in a mixture of 5 ml ethyl acetate and 0.5 ml methanol and chromatographed on a column packed with 100 g Silica gel 60, 230-400 mesh ASTM. The product was eluted by an ethyl acetate/methanol 9:1 mixture. The combined fractions were evaporated, and the solid residue was triturated with 40 ml diethyl ether and filtered off, washed with cold ether (2×50 ml) and dried in vacuo at 50° C. for 3 h to yield 1.40 g (92%) of the product as white crystals. M.p. 139-140° C.

$^1$H NMR (DMSO-$d_6$): 1.22-1.66 (6H, m, —C$^\beta$$\underline{H}_2$C$^\gamma$$\underline{H}_2$C$^\delta$$\underline{H}_2$— Lys), 1.66 (2H, m, —NHCH$_2$C$\underline{H}_2$CH$_2$CO—), 2.35 (2H, m, —NHCH$_2$CH$_2$C$\underline{H}_2$CO—), 2.94 (2H, m, C$^\epsilon$$\underline{H}_2$ Lys), 3.06 (2H, m, —NHC$\underline{H}_2$CH$_2$CH$_2$CO—), 3.68 (2H, d, CH$_2$ Gly), 4.13 (1H, m, C$^\alpha$H Lys), 4.99 (2H, s, —CO—OC$\underline{H}_2$C$_6$H$_5$ Lys(Z)), 5.07 (2H, s, —OC$\underline{H}_2$C$_6$H$_5$), 7.20 (1H, d, N$^\epsilon$H Lys), 7.33 (10H, m, —CO—OCH$_2$C$_6$$\underline{H}_5$ Lys(Z), —OCH$_2$C$_6$$\underline{H}_5$), 7.88 (1H, t, N$\underline{H}$CH$_2$CH$_2$CH$_2$CO—), 7.94 (1H, d, NH Lys), 8.10 (1H, t, NH Gly).

h) The preparation of N-acetyl-glycyl-lysyl-γ-aminobutyric acid, $CH_3$CO-Gly-Lys-NH($CH_2$)$_3$COOH (GK-7)

1.27 g (2.40 mmol) $CH_3$CO-Gly-Lys(Z)—NH($CH_2$)$_3$CO—OBzl was dissolved in a mixture of 15 ml methanol, 1 ml water and 2 ml acetic acid. To this solution 1 g 10% Pd/C suspended in 5 ml methanol and 4 ml (39.49 mmol) cyclohexene were added. The reaction mix was heated to reflux under stirring for 30 min followed by cooling. The catalyst was filtered off and washed with methanol (2×10 ml). The combined filtrates were evaporated, and the resulting oil was taken up in 50 ml water. The aqueous solution was washed with 50 ml ethyl acetate, then the aqueous layer was concentrated, and the residue was taken up in 25 ml acetic acid and evaporated. The resulting oil was dried in vacuo to yield 882 mg (94%, total recovery 71%) of a white solid. M.p. 198-202° C. $C_{14}H_{26}N_4O_5$.

$^1$H NMR (DMSO-$d_6$): 1.26 (2H, m, $C^\gamma H_2$ Lys), 1.48 (2H, m, $C^\delta H_2$ Lys), 1.62 (2H, m, —NHCH$_2$C$\underline{H}_2$CH$_2$COOH), 1.78 (2H, m, $C^\beta H_2$ Lys), 1.85 (3H, s, C$\underline{H}_3$CO—), 2.08 (2H, m, —NHCH$_2$CH$_2$C$\underline{H}_2$COOH), 2.69 (2H, m, $C^\epsilon H_2$ Lys), 2.91 and 3.10 (2H, m, —NHC$\underline{H}_2$CH$_2$CH$_2$COOH), 3.70 (2H, d, CH$_2$ Gly), 4.13 (1H, m, $C^\alpha \underline{H}$ Lys), 8.10 (1H, d, NH Lys), 8.31 (1H, t, —N$\underline{H}$CH$_2$CH$_2$CH$_2$COOH), 8.40 (1H, t, NH Gly).

Example 10

The synthesis of N,N'-adipyl-bis-(glycyl-lysyl-γ-aminobutyric acid), Ad-(Gly-Lys-NH(CH$_2$)$_3$COOH)$_2$ (GK-8)

a) The preparation of adipic acid di-N$^\epsilon$-oxysuccinimide ester, (CH$_2$)$_4$(COOSu)$_2$ To a solution of 7.31 g (50.00 mmol) adipic acid and 13.81 g (120.00 mmol) N-hydroxysuccinimide in 200 ml THF under cooling to 0° C. a solution of 22.70 g (110.00 mmol) DCCD in 50 ml methylene chloride was added. The reaction mixture was stirred overnight in an ice bath. Then the reaction mixture was filtered to remove the dicyclohexylurea precipitate, and the filtrate was evaporated to produce a crystalline mass. Since the weight of the precipitate upon filtration was greater than the calculated weight of dicyclohexylurea, the precipitate was stirred with 200 ml DMFA and filtered off into the flask containing the crystalline residue to further separate the product from the remaining dicyclohexylurea. Thus essentially all the crystalline residue was dissolved in the dimethylformamide filtrate. The resulting dimethylformamide solution was filtered again to remove a small amount of dicyclohexylurea and evaporated. The resulting crystalline mass was triturated with a mixture of 200 ml ethyl acetate and 100 ml THF to allow a trace of N-hydroxysuccinimide to pass into the solution. The crystalline product was filtered off, washed with 150 ml ethyl acetate followed by diethyl ether (2×150 ml) and dried in vacuo at 50° C. for 4 h to yield 12.92 g (76%) of the product.

b) The preparation of N-adipyl-bis-(glycyl-N$^\epsilon$-benzyloxycarbonyl-lysyl-γ-aminobutyric acid benzyl ester), Ad-(Gly-Lys(Z)—NH(CH$_2$)$_3$CO—OBzl)$_2$ 3 ml (2.73 mmol) N-methylmorpholine was added to a solution of 375 mg (1.10 mmol) (CH$_2$)$_4$(COOSu)$_2$ and 1.50 g (2.39 mmol) H-Gly-Lys(Z)—NH(CH$_2$)$_3$CO—OBzl.TFA (for which the preparation is described in Example 9, section f). Then the solution was filtered, evaporated to a state of fluid oil (~ by ⅔), and 100 ml 1N HCl was added to the residue. The resulting precipitate was washed successively with 50 ml 1N HCl, water (2×50 ml), ethyl acetate (2×50 ml), and diethyl ether (2×50 ml) followed by drying in vacuo at 50° C. for 4 h. The residue was taken up in a mixture of 15 ml chloroform and 2 ml methanol and applied onto a silica gel layer (Silica gel 60, 230-400 mesh ASTM) on a 100 ml filter using a chloroform-methanol-acetic acid 20:2:1 mixture as the eluent. The appropriate fraction (500 ml) was evaporated, and the solid residue was triturated with 50 ml diethyl ether and filtered off, then washed with ether (2×50 ml) to yield 1.20 g (94%) of the product. M.p. 186-187° C.

$^1$H NMR (DMSO-$d_6$): 1.15-1.45 (12H, m, 2 —C$^\beta \underline{H}_2$C$^\gamma$ $\underline{H}_2$C$^\delta \underline{H}_2$— Lys), 1.45 (8H, m, (CH$_2$)$_4$ Ad), 1.65 (4H, m, 2—NHCH$_2$C$\underline{H}_2$CH$_2$CO—), 2.10 (4H, m, 2 C$^\epsilon$H$_2$ Lys), (4H, t, 2 —NHCH$_2$CH$_2$C$\underline{H}_2$CO—), 3.06 (4H, m, —NHC $\underline{H}_2$CH$_2$CH$_2$CO—), 3.68 (4H, each d, 2 CH$_2$ Gly), 4.12 (2H, m, 2 C$^\alpha \underline{H}$ Lys), 4.98 (4H, each s, 2 —CO—OC$\underline{H}_2$C$_6$H$_5$ Lys(Z)), 5.07 (4H, each s, 2 —C$\underline{H}_2$C$_6$H$_5$), 7.21 (2H, each t, 2 N$^\epsilon \underline{H}$ Lys), 7.27-7.37 (20H, m, 2 —CO—OCH$_2$C$_6\underline{H}_5$ Lys(Z), 2-CH$_2$C$_6\underline{H}_5$), 7.91 (2H, each t, 2 —N $\underline{H}$CH$_2$CH$_2$CH$_2$CO—), 7.94 (2H, each d, 2 NH Lys), 8.05 (2H, each t, 2 NH Gly).

c) The preparation of N-adipyl-bis-(glycyl-lysyl-γ-aminobutyric acid), Ad-(Gly-Lys-NH(CH$_2$)$_3$COOH)$_2$ (GK-8)

1.16 g (1.00 mmol) Ad-(Gly-Lys(Z)—NH(CH$_2$)$_3$CO—OBzl)$_2$ was dissolved in a mixture of 20 ml methanol, 1 ml water and 5 ml acetic acid. To this solution 1 g 10% Pd/C suspended in 5 ml methanol and 4 ml (39.49 mmol) cyclohexene were added. The reaction mix was heated to reflux under stirring for 30 min followed by cooling. The catalyst was filtered off and washed with methanol (3×10 ml) and a water-acetic acid 1:1 mixture (3×10 ml). The combined filtrates were evaporated, and the resulting oil was taken up in a mixture of 50 ml water and 5 ml acetic acid. The resulting solution was washed with 50 ml ethyl acetate and concentrated, and the residue was taken up in 25 ml acetic acid and evaporated again. The resulting oil was dried in vacuo to yield 0.76 g (94%, total recovery 67%) of an oily product in the form of diacetate.

$^1$H NMR (DMSO-$d_6$): 1.16-1.77 (20H, m, 2 —C$^\beta \underline{H}_2$C$^\gamma$ $\underline{H}_2$C$^\delta \underline{H}_2$— Lys, —COCH$_2$C$\underline{H}_2$C$\underline{H}_2$CH$_2$CO—, 2 —NHCH$_2$C$\underline{H}_2$CH$_2$CO—), 1.83 (6H, s, 2 C$\underline{H}_3$COOH), 2.13 (8H, m, 2 —NHCH$_2$CH$_2$C$\underline{H}_2$CO—, —COC$\underline{H}_2$CH$_2$CH$_2$C $\underline{H}_2$CO—), 2.72 (4H, m, 2 C$^\epsilon$H$_2$ Lys), 3.00 (4H, m, 2 —NHC $\underline{H}_2$CH$_2$CH$_2$CO—), 3.70 (4H, d, 2 CH$_2$ Gly), 4.32 (2H, m, 2 C$^\alpha \underline{H}$ Lys), 8.10 (2H, t, 2 —N$\underline{H}$CH$_2$CH$_2$CO—), 8.11 (2H, d, 2 NH Lys), 8.33 (2H, t, 2 NH Gly).

Example 11

The synthesis of N-monosuccinyl-seryl-lysine amide, HOOC(CH$_2$)$_2$CO-Ser-Lys-NH$_2$ (GSB-104)

a) The preparation of N-t-butyloxycarbonyl-N$^\epsilon$-(2-chlorobenzyloxycarbonyl)-lysine amide, Boc-Lys(2-Cl—Z)—NH$_2$ To a solution of 1.5 g (3.62 mmol) Boc-Lys(2-Cl—Z)—OH in 10 ml DMFA at –10° C. were successively added 0.34 ml (3.62 mmol) N-methylmorpholine and 0.52 ml (3.62 mmol) isobutylformate each time maintaining the temperature below –5° C. Then 10 ml DMFA saturated with ammonia (pH 8) was added. The reaction mix was stirred at –10° C. for 1 h and at room temperature for another hour. The solvent was removed in vacuo, and the residue was taken up in 30 ml chloroform and washed successively with water, 5% NaHCO$_3$, 1N HCl and water again. The resulting solution was evaporated and dried in vacuo to yield 1.3 g (87%) of a white powder. $R_f$ 0.49 (C); m.p. 105-106° C.; $[\alpha]^{20}_D$ –8.5° (c=0.4; chloroform).

$^1$H NMR (DMSO-$d_6$): 1.36 (9H, s, —CO—OC(CH$_3$)$_3$), 1.17-1.65 (6H, m, —C$^\beta \underline{H}_2$C$^\gamma \underline{H}_2$C$^\delta \underline{H}_2$— Lys), 2.97 (2H, m, C$^\epsilon$H$_2$ Lys), 3.80 (1H, m, C$^\alpha \underline{H}$ Lys), 5.07 (2H, s, —CO—OC $\underline{H}_2$C$_6$H$_4$Cl), 6.73 (1H, d, NH Lys), 6.96 and 7.25 (2H, 2s, NH$_2$ amide), 7.37 (1H, t, N$^\epsilon \underline{H}$ Lys), 7.30-7.50 (4H, m, —CO—OCH$_2$C$_6\underline{H}_4$Cl).

b) The preparation of N$^\epsilon$-(2-chlorobenzyloxycarbonyl)-lysine amide trifluoracetate, H-Lys(2-Cl—Z)—NH$_2$.TFA A solution of 400 mg Boc-Lys(2-Cl—Z)—NH$_2$ in 3 ml TFA and 3 ml dichloromethane was stirred at room temperature for 30 min. Then the solvent was removed in vacuo, and the residue was evaporated twice with 10 ml ether and dried in vacuo to yield 410 mg (99%) of the product in the form of trifluoracetate salt. M.p. 67-71° C.

$^1$H NMR (DMSO-d$_6$): 1.31 (2H, m, C$^\gamma$H$_2$ Lys), 1.40 (2H, m, C$^\delta$H$_2$ Lys), 1.70 (2H, m, C$^\beta$H$_2$ Lys), 2.99 (2H, m, C$^\epsilon$H$_2$ Lys), 3.68 (1H, m, C$^\alpha$H Lys), 5.08 (2H, s, —CO—OCH$_2$C$_6$H$_4$Cl), 7.31-7.52 (4H, m, —CO—OCH$_2$C$_6$H$_4$Cl), 7.57 and 7.88 (2H, 2s, NH$_2$ amide), 8.09 (3H, s, NH$_3^+$ Lys).

c) The preparation of N-t-butyloxycarbonyl-O-benzyl-seryl-N$^\epsilon$-(2-chlorobenzyl-oxycarbonyl)-lysine amide, Boc-Ser(OBzl)-Lys(2-Cl—Z)—NH$_2$ 0.43 ml (2.46 mmol) DIEA was added to a solution of 240 mg (0.82 mmol) Boc-Ser(OBzl)-OH and 532.2 mg (0.90 mmol) PyBOP in 10 ml DMFA. The resulting solution was added to a solution of 350 mg (0.82 mmol) H-Lys(2-Cl—Z)—NH$_2$.TFA in 10 ml DMFA. The solution was allowed to stand overnight. Then 0.5 ml DETMDA was added to the reaction mixture and stirred for 30 min. The reaction mass was diluted with 200 ml ethyl acetate and washed successively with water, 2% H$_2$SO$_4$, 3% K$_2$CO$_3$, and sat. NaCl followed by drying over anhydrous MgSO$_4$. Then the solvent was removed in vacuo, and the residue was dried in vacuo to yield 0.51 g of a white powder. The powder was found by HPLC to comprise 2 components of R$_f$ 0.35 and R$_f$ 0.40 (D). The separation by HPLC yielded 330 mg (68.2%) of the final product as a white powder. R$_f$ 0.35 (D); m.p. 127-129° C.; [α]$^{20}_D$ -2.5° (c=0.4; DMFA).

$^1$H NMR (DMSO-d$_6$): 1.15-1.85 (6H, m, —C$^\beta$H$_2$C$^\gamma$H$_2$C$^\delta$H$_2$— Lys), 1.37 (9H, s, —CO—OC(CH$_3$)$_3$), 2.93 (2H, m, C$^\epsilon$H$_2$ Lys), 3.58 (2H, m, C$^\beta$H$_2$ Ser), 4.17 (1H, m, C$^\alpha$H Lys), 4.21 (1H, m, C$^\alpha$H Ser), 4.46 (2H, s, —CH$_2$C$_6$H$_5$Ser(OBzl)), 5.06 (1H, s, —CO—OCH$_2$C$_6$H$_4$Cl), 7.05 (1H, d, NH Ser), 7.09 and 7.25 (2H, 2s, NH$_2$ amide), 7.2-7.5 (9H, m, —CH$_2$C$_6$H$_5$ Ser(OBzl), —CO—OCH$_2$C$_6$H$_4$Cl), 7.45 (2H, t, N$^\epsilon$H Lys), 7.87 (1H, d, NH Ser).

d) The preparation of O-benzyl-seryl-N$^\epsilon$-(2-chlorobenzyloxycarbonyl)-lysine amide trifluoracetate, H-Ser(OBzl)-Lys(2-Cl—Z)—NH$_2$.TFA A solution of 287 mg (0.5 mmol) Boc-Ser(OBzl)-Lys(2-Cl—Z)—NH$_2$ in 2 ml TFA was stirred for 30 min followed by evaporation. The residue was crystallized with ether to yield 265 mg (90%) of the product as white crystals. R$_f$ 0.03 (D); m.p. 153-155° C.; [α]$^{20}_D$ +6.25° (c=0.4; DMFA).

$^1$H NMR (DMSO-d$_6$): 1.27 (2H, m, C$^\gamma$H$_2$ Lys), 1.39 (2H, m, C$^\delta$H$_2$ Lys), 1.54 and 1.65 (2H, m, C$^\beta$H$_2$ Lys), 2.97 (2H, m, C$^\epsilon$H$_2$ Lys), 3.67 and 3.74 (2H, 2d, C$^\beta$H$_2$ Ser), 4.11 (1 H, m, C$^\alpha$H Ser), 4.24 (1H, m, C$^\alpha$H Lys), 4.54 (2H, s, —CH$_2$C$_6$H$_5$ Ser(OBzl)), 5.07 (2H, s, —CO—OCH$_2$C$_6$H$_4$Cl), 7.14 and 7.45 (9H, m, —CH$_2$C$_6$H$_5$ Ser(OBzl), —CO—OCH$_2$C$_6$H$_4$Cl), 7.35 (1H, t, N$^\epsilon$H Lys), 8.25 (3H, br. s, NH$_3^+$ Ser), 8.57 (1H, d, NH Lys).

e) The preparation of N-monosuccinyl-O-benzyl-seryl-N$^\epsilon$-(2-chlorobenzyl-oxycarbonyl)-lysine amide, HOOC(CH$_2$)$_2$CO-Ser(OBzl)-Lys(2-Cl—Z)—NH$_2$ 0.06 ml (0.44 mmol) TEA was added to a solution of 240 mg (0.40 mmol) H-Ser(OBzl)-Lys(2-Cl—Z)—NH$_2$.TFA in 4 ml DMFA. The solution was stirred for 15 min and 60 mg (1.2 mmol) succinic anhydride was added. The reaction mix was stirred overnight and, when the starting compound disappeared (TLC control), 25 ml water was added. The resulting white precipitate was filtered off, washed with water and dried to yield 207 mg (88%) of the product. R$_f$ 0.28 (C); m.p. 158-166° C.

$^1$H NMR (DMSO-d$_6$): 1.25 (2H, m, C$^\gamma$H$_2$ Lys), 1.35 (2H, m, C$^\delta$H$_2$ Lys), 1.52 and 1.68 (2H, 2m, C$^\beta$H$_2$ Lys), 2.41 (4H, m, HOOCCH$_2$CH$_2$CO—), 2.94 (2H, m, C$^\epsilon$H$_2$ Lys), 3.58 and 3.60 (2H, 2d, C$^\beta$H$_2$ Ser), 4.13 (1H, m, C$^\alpha$H Lys), 4.47 (1H, m, C$^\alpha$H Ser), 4.48 (2H, s —CH$_2$C$_6$H$_5$ Ser(OBzl)), 5.07 (2H, s, —CO—OCH$_2$C$_6$H$_4$Cl), 7.06 and 7.14 (2H, 2s, NH$_2$ amide), 7.20-7.50 (9H, m, —CH$_2$C$_6$H$_5$ Ser(OBzl), —CO—OCH$_2$C$_6$H$_4$Cl), 7.34 (1H, t, N$^\epsilon$H Lys), 7.92 (1H, d, NH Lys), 8.25 (1H d, NH Ser).

f) The preparation of N-monosuccinyl-seryl-lysine amide, HOOC(CH$_2$)$_2$CO-Ser-Lys-NH$_2$ (GSB-104)

180 mg (0.30 mmol) 10% Pd/C was added to a solution of 180 mg (0.30 mmol) HOOC(CH$_2$)$_2$CO-Ser(OBzl)-Lys(2-Cl—Z)—NH$_2$ in 10 ml DMFA and stirred under hydrogen for 2 days until the starting compound disappeared (TLC control). Then the catalyst was filtered off, and the filtrate was evaporated to yield 95 mg (100%, total recovery 51.7%) of the product as a hygroscopic powder. R$_f$ 0 (C), R$_f$ 0.35 (E); [α]$^{20}_D$ -15.75° (c=0.4; DMFA).

$^1$H NMR (DMSO-d$_6$): 1.29 (2H, m, C$^\gamma$H$_2$ Lys), 1.79 (2H, m, C$^\beta$H$_2$ Lys), 2.03 (2H, m, C$^\delta$H$_2$ Lys), 2.51 (2H, 2d, HOOCCH$_2$CH$_2$CO—), 2.68 (2H, 2d, HOOCCH$_2$CH$_2$CO—), 3.91 and 4.16 (2H, 2d, C$^\beta$H$_2$ Ser), 4.53 (1H, m, C$^\alpha$H Lys), 4.62 (1H, m, C$^\alpha$H Ser), 4.78 (1H, s, —COOH Ser), 7.21 (2H, s, NH$_2$ amide), 8.31-8.35 (5H, m, N$^\epsilon$H$_3^+$ Lys, NH Ser, NH Lys).

Example 12

The synthesis of bis-(N-monosuccinyl-seryl-lysine) hexamethylenediamide, (HOOC(CH$_2$)$_2$CO-Ser-Lys-NH)$_2$—(CH$_2$)$_6$ (GSB-106)

a) The preparation of N-t-butyloxycarbonyl-N$^\epsilon$-(2-chlorobenzyloxycarbonyl)-lysine pentafluorophenyl ester, Boc-Lys(2-Cl—Z)—OPfp 3.33 g (18 mmol) pentafluorophenol was added to a solution of 7.6 g (17 mmol) Boc-Lys(2-Cl—Z)—OH in 80 ml THF. The solution was cooled to -5° C., and then a solution of 3.50 g (17 mmol) DCCD in 20 ml THF was added gradually thereto while keeping the temperature below 0° C. The reaction mix was stirred at -5° C. for 3 h and allowed to stand overnight at +4° C. The white precipitate of dicyclohexylurea was filtered off, the filtrate was evaporated, and the oily residue was crystallized from an ethyl acetate-hexane mixture (15 ml/80 ml). The resulting crystals were filtered off, washed with hexane and dried in vacuo to yield 7.18 g of the product. The mother solution was also evaporated and recrystallized from an ethyl acetate-hexane mixture (5 ml/50 ml) to yield an additional 1.05 g of the product. The total yield was 8.23 g (89%). R$_f$ 0.42 (F), R$_f$ 0.13 (G); m.p. 134-135° C.; [α]$^{20}_D$ -25.75° (c=0.4; DMFA).

$^1$H NMR (DMSO-d$_6$): 1.29 (2H, m, C$^\gamma$H$_2$ Lys), 1.42 (9H, s, —CO—OC(CH$_3$)$_3$), 1.55 (2H, m, C$^\delta$H$_2$ Lys), 1.78 (2H, m, C$^\beta$H$_2$ Lys), 4.42 (1H, m, C$^\alpha$H Lys), 5.34 (2H, s, —CO—OCH$_2$C$_6$H$_4$Cl), 6.76 (1H, d, NH Lys), 7.05-7.20 (4H, m, —CO—OCH$_2$C$_6$H$_4$Cl), 7.39 (1H, t, N$^\epsilon$H Lys).

b) The preparation of bis-(N-t-butyloxycarbonyl-N$^\epsilon$-(2-chlorobenzyloxycarbonyl)-lysine) hexamethylenediamide, (Boc-Lys(2-Cl—Z)—NH)$_2$—(CH$_2$)$_6$ 200 mg (1.72 mmol) hexamethylenediamine was added to a solution of 2 g (3.66 mmol) Boc-Lys(2-Cl—Z)—OPfp in 20 ml ethyl acetate. The reaction mix was stirred for 1 h, thereupon it was evaporated, taken up in 100 ml ethyl acetate and washed successively with 1N H$_2$SO$_4$, sat. NaCl, 3% K$_2$CO$_3$, and sat. NaCl again, then it was dried over anhydrous Na$_2$SO$_4$ and evaporated. The resulting crystalline solid was washed with hexane and dried in vacuo to yield 1.45 g (96%) of the product. R$_f$ 0.56 (H); m.p. 109-114° C.; [α]$^{20}_D$ -12.0° (c=0.4; DMFA).

$^1$H NMR (DMSO-d$_6$): 1.29 (8H, m, 2 C$^\gamma$H$_2$ Lys, —NHCH$_2$CH$_2$CH$_2$CH$_2$CH$_2$CH$_2$NH—), 1.42 (18H, s, 2 —CO—OC(CH$_3$)$_3$), 1.55 (8H, m, 2 C$^\delta$H$_2$ Lys, —NHCH$_2$CH$_2$CH$_2$CH$_2$CH$_2$CH$_2$NH—), 1.79 (4H, m, 2 C$^\beta$H$_2$ Lys), 2.96 (4H, m, 2 C$^\epsilon$H$_2$ Lys), 3.20 (4H, m, —NHCH$_2$CH$_2$CH$_2$CH$_2$CH$_2$CH$_2$NH—), 4.53 (2H, m, C$^\alpha$H Lys), 5.34 (4H, s, 2 —CO—OCH$_2$C$_6$H$_4$Cl), 6.76 (2H, d, 2 NH Lys), 7.39 (2H, t, N$^\epsilon$H Lys), 8.01 (2H, t, —NHCH$_2$CH$_2$CH$_2$CH$_2$CH$_2$CH$_2$NH—).

c) The preparation of bis-(N$^\epsilon$-(2-chlorobenzyloxycarbonyl)-lysine) hexamethylenediamide dihydrochloride, (H-Lys(2-Cl—Z)—NH)$_2$—(CH$_2$)$_6$.2HCl 10 ml 4N HCl in dioxane was added to a solution of 1.42 g (1.71 mmol) (Boc-Lys(2-Cl—Z)—NH)$_2$—(CH$_2$)$_6$ in 10 ml dioxane. When the reaction was complete (TLC control), the solution was evaporated dry to yield the product as a foam (solidified oil). It was used in the next step without any further treatment.

$^1$H NMR (DMSO-d$_6$): 0.95-1.75 (20H, m, 2 —CH$_2$$^\beta$CH$_2$$^\gamma$CH$_2$$^\delta$— Lys, —NHCH$_2$CH$_2$CH$_2$CH$_2$CH$_2$CH$_2$NH—), 2.98 (4H, m, —NHCH$_2$CH$_2$CH$_2$CH$_2$CH$_2$CH$_2$NH—), 3.09 (4H, m, 2 C$^\epsilon$H$_2$ Lys), 3.70 (2H, m, 2 C$^\alpha$H Lys), 5.07 (4 H, s, 2 —CO—OCH$_2$C$_6$H$_4$Cl), 7.37 (2H, t, —NHCH$_2$CH$_2$CH$_2$CH$_2$CH$_2$CH$_2$NH—), 7.45 (8H, m, 2 —CO—OCH$_2$C$_6$H$_4$Cl), 8.23 (6H, m, 2 N$^+$H$_3$ Lys), 8.59 (2H, t, 2 N$^\epsilon$H Lys).

d) The preparation of bis-(N-t-butyloxycarbonyl-O-benzyl-seryl-N$^\epsilon$-(2-chlorobenzyloxycarbonyl)-lysine) hexamethylenediamide, (Boc-Ser(OBzl)-Lys(2-Cl—Z)—NH)$_2$—(CH$_2$)$_6$ To a solution of (H-Lys(2-Cl—Z)—NH)$_2$—(CH$_2$)$_6$.2HCl (1.32 mmol) in 10 ml DMFA first 0.46 ml (2.64 mmol) DIEA (pH 8) was added followed by 2.44 g (2.64 mmol) Boc-Ser(OBzl)-OPfp. The reaction mixture was stirred at room temperature for 1 h and allowed to stand overnight. On the next day 0.5 ml DETMDA was added to the reaction mix and stirred for 15 min. Then it was diluted with 150 ml ethyl acetate, washed successively with water, 3% H$_2$SO$_4$, 2% K$_2$CO$_3$, and sat. NaCl, dried over anhydrous Na$_2$SO$_4$ and evaporated. The residue was recrystallized from methanol to yield 0.75 g (45%) of the product as a white powder. R$_f$ 0.44 (C); m.p. 143-151° C.; [α]$^{20}_D$ −2.5° (c=0.4; DMFA).

$^1$H NMR (DMSO-d$_6$): 0.93-1.83 (38H, m, 2 —CO—OC(CH$_3$)$_3$, 2 —CH$_2$$^\beta$CH$_2$$^\gamma$CH$_2$$^\delta$— Lys, —NHCH$_2$CH$_2$CH$_2$CH$_2$CH$_2$CH$_2$NH—), 2.93 (8H, m, 2 C$^\epsilon$H$_2$ Lys, —NHCH$_2$CH$_2$CH$_2$CH$_2$CH$_2$CH$_2$NH—), 3.59 (4H, m, 2 C$^\beta$H$_2$ Ser), 4.20 (4H, m, 2 C$^\alpha$H Lys, 2 C$^\alpha$H Ser), 4.47 (4H, s, 2 —CH$_2$C$_6$H$_5$ Ser(OBzl)), 5.07 (4H, s, 2 —CO—OCH$_2$C$_6$H$_4$Cl), 7.00 (2H, d, NH Ser), 7.19-7.50 (20H, m, 2 —CH$_2$C$_6$H$_5$ Ser(OBzl), 2 —CO—OCH$_2$C$_6$H$_4$Cl, —NHCH$_2$CH$_2$CH$_2$CH$_2$CH$_2$CH$_2$NH—), 7.77 (2H, t, N$^\epsilon$H Lys), 7.91 (2H, d, NH Lys).

e) The preparation of bis-(O-benzyl-seryl-N$^\epsilon$-(2-chlorobenzyloxycarbonyl)-lysine) hexamethylenediamide ditrifluoroacetate, (H-Ser(OBzl)-Lys(2-Cl—Z)—NH)$_2$—(CH$_2$)$_6$.2TFA 0.34 g (Boc-Ser(OBzl)-Lys(2-Cl—Z)—NH)$_2$—(CH$_2$)$_6$ was dissolved in 32 ml TFA and stirred for 40 min, then the reaction mix was evaporated. 15 ml benzene was added twice to the residue and evaporated again to yield 0.42 g of a beige-coloured powder. The powder was recrystallized from ether to yield 0.25 g (72%) of the product as a white powder that was chromatographically homogeneous. R$_f$ 0.33 (C), R$_f$ 0.67 (E); m.p. 117-122° C.; [α]$^{20}_D$ +4.75° (c=0.4; DMFA).

f) The preparation of bis-(N-monosuccinyl-O-benzyl-seryl-N$^\epsilon$-(2-chlorobenzyl-oxycarbonyl)-lysine) hexamethylenediamide, (HOOC(CH$_2$)$_2$CO-Ser(OBzl)-Lys(2-Cl—Z)—NH)$_2$—(CH$_2$)$_6$ 0.23 g (0.178 mmol) (H-Ser(OBzl)-Lys(2-Cl—Z)—NH)$_2$—(CH$_2$)$_6$.2TFA was suspended in 5 ml DMFA. 0.055 ml (0.40 mmol) TEA was added to the suspension and stirred for 30 min, then 0.108 g (1.078 mmol) succinic anhydride was added. The reaction mixture was stirred for 1 h, making the suspension to become clear, and was allowed to stand overnight. When the starting compound disappeared (TLC control), the reaction mix was diluted with water. The resulting white precipitate was filtered off, washed with ether and dried in vacuo to yield 0.18 g (91%) of the product. R$_f$ 0.12 (C); m.p. 178-180° C.; [α]$^{20}_D$ −11.25° (c=0.4; DMFA).

$^1$H NMR (DMSO-d$_6$): 0.95-1.78 (20H, m, 2 —CH$_2$$^\beta$CH$_2$$^\gamma$CH$_2$$^\delta$— Lys, —NHCH$_2$CH$_2$CH$_2$CH$_2$CH$_2$CH$_2$NH—), 2.42 (8H, m, 2 HOOCCH$_2$CH$_2$CO), 2.97 (8H, m, 2 C$^\epsilon$H$_2$ Lys, —NHCH$_2$CH$_2$CH$_2$CH$_2$CH$_2$CH$_2$NH—), 3.60 (4H, m, 2 C$^\beta$H$_2$ Ser), 4.14 (4H, m, 2 C$^\alpha$H Lys), 4.44 (2H, m, 2 C$^\alpha$H Ser), 4.45 (4H, s, 2 —CH$_2$C$_6$H$_5$ Ser(OBzl)), 5.07 (4H, s, 2 —CO—OCH$_2$C$_6$H$_4$Cl), 7.20-7.49 (20H, m, 2 —CH$_2$C$_6$H$_5$ Ser(OBzl), 2 —CO—OCH$_2$C$_6$H$_4$Cl, —NHCH$_2$CH$_2$CH$_2$CH$_2$CH$_2$CH$_2$NH—), 7.53 (2H, t, 2 N$^\epsilon$H Lys), 7.89 (2H, d, 2 NH Lys), 8.24 (2H, d, 2 NH Ser).

f) The preparation of bis-(N-monosuccinyl-seryl-lysine) hexamethylenediamide, (HOOC(CH$_2$)$_2$CO-Ser-Lys-NH)$_2$—(CH$_2$)$_6$ (GSB-106

200 mg 10% Pd/C was added to a solution of 96 mg (0.076 mmol) (HOOC(CH$_2$)$_2$CO-Ser(OBzl)-Lys(2-Cl—Z)—NH)$_2$—(CH$_2$)$_6$ in 30 ml methanol and stirred under hydrogen for 11 h. When the hydrogenation was complete (TLC control), the catalyst was filtered off. The filtrate was evaporated, and the residue was dried in vacuo to yield 65 mg (quantitatively) of the product. R$_f$ 0 (C), R$_f$ 0.04 (E). C$_{32}$H$_{58}$N$_8$O$_{12}$.

$^1$H NMR (DMSO-d$_6$): 1.00-1.75 (20H, m, 2 —CH$_2$$^\beta$CH$_2$$^\gamma$CH$_2$$^\delta$— Lys, —NHCH$_2$CH$_2$CH$_2$CH$_2$CH$_2$CH$_2$NH—), 2.42 (8H, m, 2 HOOCCH$_2$CH$_2$CO), 2.74 (4H, m, 2 C$^\epsilon$H$_2$ Lys), 3.00 (4H, m, —NHCH$_2$CH$_2$CH$_2$CH$_2$CH$_2$CH$_2$NH—), 3.52 and 3.63 (4H, 2d, 2 C$^\beta$H$_2$ Ser), 4.14 (2H, m, C$^\alpha$H Lys), 4.27 (2H, m, 2 C$^\alpha$H Ser), 7.68 (2H, t, —NHCH$_2$CH$_2$CH$_2$CH$_2$CH$_2$CH$_2$NH—), 7.72 (br. s, N$^\epsilon$H$_3$$^+$ Lys), 7.95 (2H, d, NH Lys), 8.10 (2H, d, NH Ser), 7.43 (br. s, —OH).

Example 13

The synthesis of bis-(N-(γ-oxybutyryl)-lysyl-lysine) hexamethylenediamide, (HO(CH$_2$)$_3$CO-Lys-Lys-NH)$_2$—(CH$_2$)$_6$ (GSB-120)

a) The preparation of N-t-butyloxycarbonyl-N$^\epsilon$-benzyloxycarbonyl-lysine pentafluorophenyl ester, Boc-Lys(Z)—OPfp 4.84 g (26.285 mmol) pentafluorophenol in 40 ml THF was added to a solution of 10 g (26.285 mmol) Boc-Lys(Z)—OH in 100 ml THF. The solution was cooled to −3° C., and then a solution of 5.42 g (26.285 mmol) DCCD in 40 ml THF was added. The reaction mix was stirred at −5° C. to 0° C. for 1 h 15 min and allowed to stand overnight at +5° C. On the next day the white precipitate of dicyclohexylurea was filtered off, and the filtrate was evaporated. The residue was recrystallized from an ethyl acetate-hexane mixture to yield 12.55 g (87.5%) of the product. R$_f$ 0.56 (F).

b) The preparation of bis-(N-t-butyloxycarbonyl-N$^\epsilon$-benzyloxycarbonyl-lysine) hexamethylenediamide, (Boc-Lys(Z)—NH)$_2$—(CH$_2$)$_6$ 0.50 g (4.31 mmol) hexamethylenediamine in 50 ml DMFA was added to a solution of 4.91 g (9.00 mmol) Boc-Lys(Z)—OPfp in 50 ml DMFA. The reaction mix was stirred for 1 h followed by standing overnight at room temperature. On the next day 0.5 ml DETMDA was added to the reaction mixture and stirred for 30 min. Then the reaction mix was evaporated in half and diluted with 100 ml ethyl acetate. The organic phase was washed with sat. Na$_2$SO$_4$ (4×25 ml), and the aqueous phases were combined and washed with 50 ml ethyl acetate. The ethyl acetate layers were combined and washed successively with 3% H$_2$SO$_4$ (2×50 ml), 3% K$_2$CO$_3$ (2×50 ml), and sat. Na$_2$SO$_4$ (2×50 ml), then were dried over anhydrous Na$_2$SO$_4$ and evaporated to yield 3.59 g (99.16%) of the product. R$_f$ 0.91 (E); m.p. 97-99° C.; [α]$^{20}_D$ −7.25° (c=0.4; DMFA).

c) The preparation of bis-(N$^\epsilon$-benzyloxycarbonyl)-lysine) hexamethylenediamide ditrifluoracetate, (H-Lys(Z)—NH)$_2$—(CH$_2$)$_6$.2TFA 3.59 g (4.27 mmol) (Boc-Lys(Z)—NH)$_2$—(CH$_2$)$_6$ was dissolved in 8 ml TFA, stirred for 30 min and evaporated. The residue was evaporated with diethyl ether 6 more times to yield 3.71 g of the product as an oil. It was used in the next step without any further treatment. R$_f$ 0.29 (E).

d) The preparation of bis-(N-t-butyloxycarbonyl-N$^\epsilon$-benzyloxycarbonyl-lysyl-N$^\epsilon$-benzyloxycarbonyl-lysine) hexamethylenediamide, (Boc-Lys(Z)-Lys(Z)—NH)$_2$—(CH$_2$)$_6$ 2 ml N-methylmorpholine (pH 8) and 5.129 g (9.39 mmol) Boc-Lys(Z)—OPfp were added to a solution of 3.71 g (4.27 mmol) (H-Lys(Z)—NH)$_2$—(CH$_2$)$_6$.2TFA in 30 ml DMFA. The reaction mix was stirred for 45 min and allowed to stand overnight followed by the addition of 0.5 ml DETMDA and stirring for 30 min. Then the reaction mixture was diluted with chloroform to 300 ml. The organic phase was washed with 100 ml water and 3% H$_2$SO$_4$ (2×100 ml). The combined aqueous fractions were extracted in chloroform (2×50 ml). The organic fractions were combined and washed with 3% K$_2$CO$_3$ (2×100 ml). The resulting aqueous fractions were washed with chloroform (2×50 ml). All the organic fractions were combined and dried over anhydrous Na$_2$SO$_4$. As evidenced by TLC, the resulting chloroform solution contained impurities in addition to the target product. In order to purify the product, the chloroform was removed in vacuo, and the residue was taken up in ethyl acetate. Immediately a white amorphous precipitate started to form that still contained impurities. The solvent was removed in vacuo, and the residue was purified by chromatography (eluent: dioxane/water, 10:1; stationary phase: Kieselgel 70-230 mesh, 60 Å (Aldrich); column 21 cm×15 mm) to yield 2.4 g (41%) of the product. R$_f$ 0.90 (E), R$_f$ 0.91 (I); m.p. 179-182° C.; [α]$^{20}_D$ −10.25° (c=0.4; DMFA).

$^1$H NMR (DMSO-d$_6$): 1.12-1.72 (32H, m, 4 —C$\underline{H}_2^\beta$C$\underline{H}_2^\gamma$C$\underline{H}_2^\delta$—Lys$^{1,2}$, —NHCH$_2$C$\underline{H}_2$CH$_2$CH$_2$C$\underline{H}_2$CH$_2$NH—), 1.36 (18H, s, —CO—OC(CH$_3$)$_3$), 2.95 (12H, m, 4 C$^\epsilon$H$_2$ Lys$^{1,2}$, —NHC$\underline{H}_2$CH$_2$CH$_2$CH$_2$CH$_2$C$\underline{H}_2$NH—), 3.84 (2H, m, C$^\alpha$H Lys$^1$), 4.17 (2H, m, 2 C$^\alpha$H Lys$^2$), 4.99 (8H, s, 4 —CO—OC$\underline{H}_2$C$_6$H$_5$), 6.92 (2H, d, 2 NH Lys$^{1,2}$), 7.20 and 7.23 (4H, 2t, 4 N$^\epsilon$H Lys$^{1,2}$), 7.33 (20H, m, 4 —CO—OCH$_2$C$_6$$\underline{H}_5$), 7.68 (2H, d, 2 NH Lys$^2$), 7.83 (2H, t, N$\underline{H}$CH$_2$CH$_2$CH$_2$CH$_2$CH$_2$CH$_2$N$\underline{H}$—).

e) The preparation of bis-(N$^\epsilon$-benzyloxycarbonyl-lysyl-N$^\epsilon$-benzyloxycarbonyl-lysine) hexamethylenediamide ditrifluoracetate, (H-Lys(Z)-Lys(Z)—NH)$_2$—(CH$_2$)$_6$.2TFA 0.639 g (0.47 mmol) (Boc-Lys(Z)-Lys(Z)—NH)$_2$—(CH$_2$)$_6$ was diluted with 3 ml TFA, stirred for 30 min and evaporated. The residue was evaporated 3 more times with ether. The resulting oil was recrystallized from ether to yield 0.597 g (91.25%) of the product as a white powder. R$_f$ 0.71 (E); m.p. 143-148° C.; [α]$^{20}_D$ +10.5° (c=0.4; DMFA).

$^1$H NMR (DMSO-d$_6$): 1.07-1.78 (32H, m, 4 —C$\underline{H}_2^\beta$C$\underline{H}_2^\gamma$C$\underline{H}_2^\delta$— Lys$^{1,2}$, NHCH$_2$C$\underline{H}_2$ CH$_2$CH$_2$CH$_2$CH$_2$NH—), 2.96 (12H, m, 4 C$^\epsilon$H Lys$^{1,2}$, —NHC$\underline{H}_2$CH$_2$CH$_2$CH$_2$CH$_2$C$\underline{H}_2$NH—), 3.78 (2H, m, 2 C$^\alpha$H Lys$^1$), 4.22 (2H, m, 2 C$^\alpha$H Lys$^2$), 4.99 (8H, s, 4 —CO—OC$\underline{H}_2$C$_6$H$_5$), 7.21 and 7.23 (4H, 2t, 4 N$^\epsilon$H Lys$^{1,2}$), 7.33 (20H, m, 4 —CO—OCH$_2$C$_6$$\underline{H}_5$), 8.00 (2H, t, N$\underline{H}$CH$_2$CH$_2$CH$_2$CH$_2$CH$_2$CH$_2$N$\underline{H}$—), 8.07 (6H, m, 2 NH$_3^+$ Lys$^1$), 8.49 (2H, d, 2 NH Lys$^2$).

f) The preparation of bis-(N—(O-benzyl-γ-oxybutyryl)-N$^\epsilon$-benzyloxycarbonyl-lysyl-N$^\epsilon$-benzyloxycarbonyl-lysine) hexamethylenediamide, (BzlO(CH$_2$)$_3$CO-Lys(Z)-Lys(Z)—NH)$_2$—(CH$_2$)$_6$ 0.370 ml N-ethylmorpholine (pH 7.5) and 0.140 ml (0.790 mmol) BzlO(CH$_2$)$_3$COOH were added to a solution of 0.50 g (0.359 mmol) (H-Lys(Z)-Lys(Z)—NH)$_2$—(CH$_2$)$_6$.2TFA and 0.35 g (0.790 mmol) BOP in 10 ml DMFA. The reaction mixture was stirred for 2 days (TLC control was absent due to the fact that the starting compound and DMFA had an identical R$_f$ value). The reaction mix was diluted with 100 ml chloroform followed by 40 ml water. The resulting amorphous precipitate was filtered off and dried in vacuo to yield 0.29 g (53.35%) of the product. R$_f$ 0.06 (E), R$_f$ 0.23 (K); m.p. 204-208° C.; [α]$^{20}_D$ −12.0° (c=0.4; DMFA).

$^1$H NMR (DMSO-d$_6$): 1.11-1.68 (32H, m, 4 —C$\underline{H}_2^\beta$C$\underline{H}_2^\gamma$C$\underline{H}_2^\delta$— Lys$^{1,2}$, —NHCH$_2$C$\underline{H}_2$CH$_2$CH$_2$C$\underline{H}_2$CH$_2$NH—), 1.75 m, 2.20 t, 3.35 t (12H, 2 BzlO—C$\underline{H}_2^\gamma$C$\underline{H}_2^\beta$C$\underline{H}_2^\alpha$CO—), 2.95 (12H, m, 4 C$^\epsilon$H$_2$ Lys$^{1,2}$, —NHC$\underline{H}_2$CH$_2$CH$_2$CH$_2$CH$_2$C$\underline{H}_2$NH—), 4.14 (4H, m, 4 C$^\alpha$H Lys$^{1,2}$), 4.42 (4H, s, 2 —C$_6$H$_5$C$\underline{H}_2$O), 4.98 (8H, s, 4 —CO—OC$\underline{H}_2$C$_6$H$_5$), 7.19 (2H, t, 4 NH Lys$^{1,2}$), 7.31 (30H, m, 2 —C$_6$H$_5$C$\underline{H}_2$O—, 4 —CO—OCH$_2$C$_6$$\underline{H}_5$), 7.74 (4H, m, 2 NH Lys$^1$, —N$\underline{H}$CH$_2$CH$_2$CH$_2$CH$_2$CH$_2$CH$_2$N$\underline{H}$—), 7.95 (2H, d, 2 NH Lys$^2$).

g) The preparation of bis-(N-(γ-oxybutyryl)-lysyl-lysine) hexamethylenediamide, (HO(CH$_2$)$_3$CO-Lys-Lys-NH)$_2$—(CH$_2$)$_6$ (GSB-120)

30 ml methanol was added to 0.165 g (0.109 mmol) ground (BzlO(CH$_2$)$_3$CO-Lys(Z)-Lys(Z)—NH)$_2$—(CH$_2$)$_6$ and 0.450 g Pd/C. The mixture was stirred under hydrogen with heating (in a 48° C. bath) for ~15 h. When the hydrogenation was complete (TLC control), the catalyst was filtered off. The filtrate was evaporated, and the residue was dried in vacuo to give the product in a quantitative yield. R$_f$ 0.0 (E, K, L, M). C$_{38}$H$_{76}$N$_{10}$O$_8$.

$^1$H NMR (DMSO-d$_6$): 1.20-1.60 (36H, m, 4 —C$\underline{H}_2^\beta$C$\underline{H}_2^\gamma$C$\underline{H}_2^\delta$— Lys$^{1,2}$, —NHCH$_2$C$\underline{H}_2$CH$_2$C$\underline{H}_2$C$\underline{H}_2$CH$_2$NH—, 2 BzlO—CH$_2^\gamma$C$\underline{H}_2^\beta$CH$_2^\alpha$CO—), 2.17 (4H, t, 2 BzlO—CH$_2^\gamma$CH$_2^\beta$C$\underline{H}^\alpha$CO—), 2.74 (4H, m, —NHC$\underline{H}_2$CH$_2$CH$_2$CH$_2$CH$_2$C$\underline{H}_2$NH—), 3.01 (8H, m, 4 C$^\epsilon$H$_2$ Lys$^{1,2}$), 3.37 (4H, t, 2 BzlO—C$\underline{H}_2^\gamma$CH$_2^\beta$CH$_2^\alpha$CO—), 4.16 and 4.32 (4H, 2m, 4 C$^\alpha$H Lys$^{1,2}$), 7.80 (2H, br. t, NHCH$_2$CH$_2$CH$_2$CH$_2$CH$_2$CH$_2$N$\underline{H}$—), 7.87 and 8.03 (4H, 2d, 4 NH Lys$^{1,2}$). 4 N$^\epsilon$H$_2$ Lys are exchangeable with HDO.

Example 14

The synthesis of N-monosuccinyl-methionyl-serine amide, HOOC(CH$_2$)$_2$CO-Met-Ser-NH$_2$ (GSB-207)

a) The preparation of N-t-butyloxycarbonyl-methionyl-serine methyl ester, Boc-Met-Ser-OMe 5.7 ml (41 mmol) TEA was added under stirring to 6.38 g (41 mmol) H-Ser-OMe hydrochloride and 15.8 g (41 mmol) Boc-Met-ONp in 50 ml DMFA. The reaction mixture was allowed to stand overnight at room temperature. When the reaction was complete (TLC control), 2 ml DMPDA was added, stirred for 30 min and evaporated. To the residue 150 ml ethyl acetate and 100 ml water were added. The organic phase was washed successively with 3% $K_2CO_3$ (3×60 ml) and 100 ml 2% HCl, dried over anhydrous $Na_2SO_4$ and evaporated. The residue was taken up in 50 ml ether, and heptane was added until turbid. The resulting crystals were filtered off, washed with heptane and dried to yield 11.6 g (80.7%) of the product. $R_f$ 0.67 (L), $R_f$ 0.80 (M); m.p. 65-68° C.; $[\alpha]^{20}_D$ −20.75° (c=0.4; methanol).

$^1$H NMR (DMSO-$d_6$): 1.36 (9H, s, —CO—O(CH$_3$)$_3$), 1.81 (2H, m, C$^\beta$H$_2$ Met), 2.45 (2H, t, C$^\gamma$H$_2$ Met), 3.62 (3H, s, —OCH$_3$), 3.70 (2H, m, C$^\beta$H$_2$ Ser), 4.08 (1H, m, C$^\alpha$H Met), 4.33 (1H, m, C$^\alpha$H Ser), 5.08 (1H, t, —OH Ser), 6.98 (1H, d, NH Met), 8.07 (1H, d, NH Ser).

b) The preparation of N-t-butyloxycarbonyl-methionyl-serine amide, Boc-Met-Ser-NH$_2$ A solution of 4 g (11.4 mmol) Boc-Met-Ser-OMe in 10 ml methanol was saturated with ammonia at 0° C. and allowed to stand for 3 days at room temperature in a sealed flask. Then it was evaporated, and the residue was crystallized with a mixture of 30 ml ether and 5 ml ethanol. The resulting crystals were filtered off and dried to yield 3.19 g (83.4%) of the product. $R_f$ 0.57 (L), $R_f$ 0.71 (M); m.p. 120-121° C.; $[\alpha]^{20}_D$ −12.25° (c=0.4; methanol).

$^1$H NMR (DMSO-$d_6$): 1.38 (9H, s, —CO—O(CH$_3$)$_3$), 1.82 (2H, m, C$^\beta$H$_2$ Met), 2.03 (3H, s, —SCH$_3$ Met), 2.46 (2H, t, C$^\gamma$H$_2$ Met), 3.56 (2H, m, C$^\beta$H$_2$ Ser), 4.0 (1H, m, C$^\alpha$H Met), 4.17 (1H, m, C$^\alpha$H Ser), 4.90 (1H, t, —OH Ser), 7.12 and 7.23 (2H, 2s, NH$_2$ amide), 7.14 (1H, d, NH Met), 7.65 (1H, d, NH Ser).

c) The preparation of N-monosuccinyl-methionyl-serine amide, HOOC(CH$_2$)$_2$CO-Met-Ser-NH$_2$ (GSB-207)

2.99 g (8.9 mmol) Boc-Met-Ser-NH$_2$ was dissolved in 15 ml TFA, stirred for 1 h and evaporated. The residue was crystallized from ether, and the resulting crystals were filtered off and washed with ether. Then it was dissolved in 20 ml 50% ethanol, treated with an Amberlite IRA-900 resin (—OH form) to pH ~10, filtered and evaporated. It was evaporated once more following the addition of DMFA. The residue was dissolved in 10 ml DMFA and 1 g (10 mmol) succinic anhydride was added. The reaction mix was stirred overnight and, when the starting compound disappeared (TLC control), 25 ml water was added thereto. The resulting white precipitate was filtered off, washed with water and dried. The reaction mix was stirred for 2 h and, when the starting compound disappeared (TLC control), it was evaporated. The residue was recrystallized from an ether-ethanol mixture (4:1) by allowing it to stand at −20° C. The resulting crystals were filtered off, washed with a cold ether-ethanol mixture (4:1) and dried to yield 0.96 g (32%, total recovery 21.5%) of the product. $R_f$ 0.11 (L), $R_f$ 0.45 (M); m.p. 101-105° C.; $[\alpha]^{20}_D$ −14.25° (c=0.4; methanol). $C_{12}H_{21}N_3O_6S$.

$^1$H NMR (DMSO-$d_6$): 1.75 and 1.90 (2H, 2m, C$^\beta$H$_2$ Met), 2.03 (3H, s, —SCH$_3$ Met), 2.41 (4H, m, HOOCC$\underline{H}_2$$\underline{H}_2$CO—), 2.44 (2H, m, C$^\gamma$H$_2$ Met), 3.58 (2H, m, C$^\beta$H$_2$ Ser), 4.16 (1H, m, C$^\alpha$H Ser), 4.31 (1H, m, C$^\alpha$H Met), 7.08 and 7.17 (2H, 2s, NH$_2$ amide), 7.75 (1H, d, NH Ser), 8.16 (1H, d, NH Met).

Example 15

The synthesis of bis-(N-monosuccinyl-methionyl-serine) heptamethylenediamide, (HOOC(CH$_2$)$_2$CO-Met-Ser-NH)$_2$—(CH$_2$)$_7$ (GSB-214)

a) The preparation of N-t-butyloxycarbonyl-methionyl-serine hydrazide, Boc-Met-Ser-N$_2$H$_3$ 3 ml hydrazine hydrate was added to a solution of 6.31 g (18 mol) Boc-Met-Ser-OMe (for which the preparation is disclosed in Example 14, section a) in 10 ml methanol and allowed to stand overnight. When the starting compound disappeared (TLC control), 10 ml water was added thereto and allowed to stand at −20° C. The resulting precipitate was filtered off, washed with cold aqueous methanol and dried to yield 6.31 g (100%) of the product. $R_f$ 0.47 (L), $R_f$ 0.66 (M); m.p. 160-162° C.; $[\alpha]^{20}_D$ −21.75° (c=0.4; methanol).

$^1$H NMR (DMSO-$d_6$): 1.37 (9H, s, —CO—O(CH$_3$)$_3$), 1.80 (2H, m, C$^\beta$H$_2$ Met), 2.02 (3H, s, —SCH$_3$ Met), 2.43 (2H, t, C$^\gamma$H$_2$ Met), 3.54 (2H, m, C$^\beta$H$_2$ Ser), 4.0 (1H, m, C$^\alpha$H Met), 4.19 (1H, m, C$^\alpha$H Ser), 4.19 (2H, d, —NH—N$\underline{H}_2$), 4.88 (1H, t, —OH Ser), 7.07 (1H, d, NH Met), 7.69 (1H, d, NH Ser), 9.02 (1H, t, —N$\underline{H}$—NH$_2$).

b) The preparation of bis-(N-t-butyloxycarbonyl-methionyl-serine) heptamethylenediamide, (Boc-Met-Ser-NH)$_2$—(CH$_2$)$_7$ To 5.23 g (14.9 mmol) Boc-Met-Ser-N$_2$H$_3$ in 25 ml DMFA cooled to −20° C. first 50 ml HCl in dioxane (~4M) followed by 1.75 ml (15 mmol) n-butylnitrite were added while keeping the temperature between −20° C. and −30° C. The reaction mixture was incubated for 3 min, and then 7.7 ml (45 mmol) IDEA was added followed by a solution of 0.91 g (7 mmol) heptamethylenediamine in 3 ml DMFA. The reaction mixture was allowed to stand overnight at room temperature followed by the addition of 250 ml ethyl acetate and 200 ml water. The organic phase was washed with 2% HCl (2×100 ml) and 100 ml 3% NaHCO$_3$ and evaporated to ~60 ml. A gradual formation of precipitate was observed which increased when the solution was cooled to −20° C. The precipitate was filtered off at room temperature, washed with ethyl acetate and dried to yield 3.3 g (29%) of the product. $R_f$ 0.59 (L), $R_f$ 0.77 (M); m.p. 160-162° C.; $[\alpha]^{20}_D$ −28.75° (c=0.4; methanol).

$^1$H NMR (DMSO-$d_6$): 1.18-1.40 (10H, m, —NHCH$_2$C$\underline{H}_2$C$\underline{H}_2$C$\underline{H}_2$C$\underline{H}_2$C$\underline{H}_2$NH—), 1.37 (18H, s, 2 —CO—O(CH$_3$)$_3$), 1.80 (4H, m, 2 C$^\beta$H$_2$ Met), 2.02 (6H, s, 2 —SCH$_3$ Met), 2.44 (4H, t, 2 C$^\gamma$H$_2$ Met), 3.02 (4H, m, —NHC$\underline{H}_2$CH$_2$CH$_2$CH$_2$CH$_2$CH$_2$C$\underline{H}_2$NH—), 3.53 (4H, m, 2 C$^\beta$H$_2$ Ser), 3.99 (2H, m, 2 C$^\alpha$H Met), 4.17 (2H, m, 2 C$^\alpha$H Ser), 7.12 (2H, d, 2 NH Met), 7.68 (2H, d, 2 NH Ser), 7.71 (2H, t, —N$\underline{H}$CH$_2$CH$_2$CH$_2$CH$_2$CH$_2$CH$_2$CH$_2$N$\underline{H}$—).

c) The preparation of bis-(N-monosuccinyl-methionyl-serine) heptamethylene-diamide, (HOOC(CH$_2$)$_2$CO-Met-Ser-NH)$_2$—(CH$_2$)$_7$ (GSB-214)

3.14 g (4.1 mmol) (Boc-Met-Ser-NH)$_2$—(CH$_2$)$_7$ was dissolved in 20 ml TFA and stirred for 30 min followed by evaporation. The residue was triturated with diethyl ether, decanted and taken up in 50 ml 50% ethanol. The solution was treated with an Amberlite IRA-900 resin (OH— form) to pH ~10 and evaporated. It was evaporated once more following the addition of DMFA. The residue was dissolved in 10 ml DMFA and 1 g (10 mmol) succinic anhydride was added. The reaction mix was stirred for 2 h and evaporated. The residue was triturated with acetone, filtered off, boiled (without drying) with 30 ml ethanol (incomplete dissolution) and allowed to stand at −20° C. The precipitate was filtered off, washed successively with cold ethanol, ether, and hexane and dried to yield 1.75 g (100%, total recovery 23.4%) of the product. $R_f$ 0.0 (L), $R_f$ 0.57 (M); m.p. 162-163° C.; $[\alpha]^{20}_D$ −9.00° (c=0.4; DMFA). $C_{31}H_{54}N_6O_{12}S_2$.

$^1$H NMR (DMSO-$d_6$): 1.20-1.40 (10H, m, —NHCH$_2$C$\underline{H}_2$C$\underline{H}_2$C$\underline{H}_2$C$\underline{H}_2$C$\underline{H}_2$NH—), 1.76 and 1.89 (4H, 2m, 2C$^\beta$H Met), 2.02 (6H, s, 2 —SCH$_3$ Met), 2.40 (8H, m, 2 HOOCC$\underline{H}_2$C$\underline{H}_2$CO—), 2.42 (4H, m, 2 C$^\gamma$H$_2$ Met), 3.01 (4H, m, —NHC$\underline{H}_2$CH$_2$CH$_2$CH$_2$CH$_2$CH$_2$C$\underline{H}_2$NH—), 3.55 (4H, m, 2 C$^\beta$H$_2$ Ser), 4.17 (2H, m, 2 C$^\alpha$H Ser), 4.30 (2H. m, 2

C$^\alpha$H Met), 7.61 (2H, t, N$\underline{H}$CH$_2$CH$_2$CH$_2$CH$_2$CH$_2$CH$_2$CH$_2$N$\underline{H}$—), 7.76 (2H, d, 2 NH Ser), 8.16 (2H, d, 2 NH Met.).

Example 16

The synthesis of N-acetyl-aspartyl-serine amide, CH$_3$CO-Asp-Ser-NH$_2$ (GBK-108)

a) The preparation of aspartic acid β-benzyl ester, H-Asp(OBzl)-OH

A solution of 167 ml benzyl alcohol, 167 ml diethyl ether and 16.7 ml conc. H$_2$SO$_4$ prepared at room temperature was evaporated without heating, by removing diethyl ether. To this solution at room temperature under vigorous stirring 22.2 g (166.8 mmol) H-Asp-OH was added in small portions. The resulting suspension was stirred vigorously at 20° C. until a completely homogeneous clear solution was obtained which was allowed to stand at room temperature for 2 days. Then 335 ml ethyl alcohol and 85 ml pyridine were added under vigorous stirring. The reaction mixture was stirred at 20° C. for 1 h. A gradual formation of a white finely dispersed precipitate took place. The solution containing the precipitate was allowed to stand at 0° C. for 1 day. Then the precipitate was filtered off and washed with water. The resulting crystalline mass was recrystallized from 335 ml water supplemented with 335 μl pyridine. The recrystallization was performed from a hot solution (80-85° C.) by allowing it to cool to room temperature and to stand for 1 day. The resulting crystals were filtered off, washed with acetone and dried to yield 10.5 g (28%) of the product as white crystals. R$_f$ 0.28 (E), R$_f$ 0.15 (I); m.p. 214-215° C.

$^1$H NMR (DMSO-d$_6$-CF$_3$COOD): 2.95 and 2.99 (2H, 2d, CH$_2$ Asp), 4.24 (1H, m, CH Asp), 5.14 (2H, s, —C$\underline{H}_2$C$_6$H$_5$), 7.35 (5H, m, —CH$_2$C$_6$$\underline{H}_5$), 8.42 (av. s, NH$_2$ amide, OH).

b) The preparation of N-t-butyloxycarbonyl-aspartic acid β-benzyl ester, Boc-Asp(OBzl)-OH 25 ml 1N NaOH was added to a solution of 5.58 g (25.0 mmol) H-Asp(OBzl)-OH in 75 ml of a dioxane-water 2:1 mixture under vigorous stirring. The reaction mixture was then cooled to 0° C. and 6.0 g (27.5 mmol) Boc$_2$O was added. The solution was stirred for 2 h at 20° C. followed by the removal of dioxane under reduced pressure. To the remaining aqueous solution an equal volume of ethyl acetate was added. The mixture was acidified to pH 3 with 10% citric acid. The aqueous phase was separated from the organic phase and washed with ethyl acetate (3×50 ml). The combined organic layers were washed with sat. NaCl and dried over anhydrous Na$_2$SO$_4$. The solvent was evaporated, and the resulting crystals were washed with petroleum ether and dried to yield 6.84 g (85%) of the product as white crystals. R$_f$ 0.88 (E), R$_f$ 0.85 (I); m.p. 97-98° C.; [α]$^{20}_D$ +3.71° (c=0.01; methanol).

c) The preparation of N-t-butyloxycarbonyl-β-benzyl-aspartic acid N-oxysuccinimide ester, Boc-L-Asp(OBzl)-OSu 5.67 g (27.5 mmol) DCCD in 20 ml THF cooled to 0° C. was added to a solution of 8.08 g (25.0 mmol) Boc-Asp(OBzl)-OH and 3.165 g (27.5 mmol) N-hydroxysuccinimide in 60 ml of cold THF under vigorous stirring. The reaction mixture was stirred at 0° C. for 18 h. The white precipitate of dicyclohexylurea was filtered off, and the solvent was removed in vacuo. The oily residue was dissolved in 40 ml CH$_2$Cl$_2$ and allowed to stand at 0° C. for 24 h. The resulting crystals were filtered off, and the filtrate was evaporated to give a crystalline (amorpho-crystalline) product in an almost quantitative yield. R$_f$ 0.33 (C), R$_f$ 0.53 (E), R$_f$ 0.93 (I); m.p. 93-94° C.; [α]$^{20}_D$ +9.29° (c=0.01; methanol).

$^1$H NMR (DMSO-d$_6$): 1.37 (9H, s, —CO—O(CH$_3$)$_3$), 2.79 (4H, br. s, —C$\underline{H}_2$C$\underline{H}_2$— —OSu), 2.88 and 3.01 (2H, 2d, CH$_2$ Asp), 4.77 (1H, m, CH Asp), 5.12 (2H, s, —C$\underline{H}_2$C$_6$H$_5$), 7.36 (5H, m, —CH$_2$C$_6$$\underline{H}_5$), 7.73 (1H, d, NH Asp).

d) The preparation of N-t-butyloxycarbonyl-O-benzyl-serine N-oxysuccinimide ester, Boc-L-Ser(OBzl)-OSu This compound was prepared in the same manner as Boc-L-Asp(OBzl)-OSu.

e) The preparation of N-t-butyloxycarbonyl-O-benzyl-serine amide, Boc-Ser(OBzl)-NH$_2$ 7.0 ml conc. NH$_4$OH was added under vigorous stirring to a solution of 9.81 g (25 mmol) Boc-Ser(OBzl)-OSu in 125 ml DMFA cooled to 0° C. The reaction mixture was stirred vigorously at 0° C. for 24 h. The precipitate was filtered off, and the filtrate was cooled to 0° C. and acidified under stirring to pH ~7 with 50-55 ml 10% citric acid. The solution was evaporated under reduced pressure to ⅕ of the initial volume. The residue was diluted with 100 ml CH$_2$Cl$_2$ and washed with 10% NaHCO$_3$ (3×50 ml) and sat. NaCl (3×50 ml). The organic phase was dried over anhydrous Na$_2$SO$_4$, and the solvent was evaporated. The resulting crystalline mass was washed successively with diethyl ether and petroleum ether and dried in vacuo to yield 5.81 g (79%) of the product. R$_f$ 0.23 (C), R$_f$ 0.91 (E), R$_f$ 0.85 (I); m.p. 98-99° C.; [α]$^{20}_D$ +25.17° (c=0.01; methanol).

f) The preparation of O-benzyl-serine amide hydrochloride, H-Ser(OBzl)-NH$_2$.HCl A solution of gaseous HCl in dioxane (~4 M, 50 ml) was added to 5.5 g (18.8 mmol) Boc-Ser(OBzl)-NH$_2$. The suspension was stirred vigorously at 20° C. for 1.5 h. The resulting crystalline mass was filtered off and washed successively with diethyl ether, CH$_2$Cl$_2$, and petroleum ether and dried in vacuo to yield 3.7 g (85%) of the product as white crystals. R$_f$ 0.0 (C), R$_f$ 0.46 (E), R$_f$ 0.44 (I); m.p. 185-186° C.; [α]$^{20}_D$ +22.94° (c=0.01; methanol).

$^1$H NMR (DMSO-d$_6$): 3.79 (2H, d, CH$_2$ Ser), 3.98 (1H, m, CH Ser), 4.48 and 4.55 (2H, 2d, —C$\underline{H}_2$C$_6$H$_5$), 7.34 (5H, m, —CH$_2$C$_6$$\underline{H}_5$), 7.30 and 7.60 (2H, 2s, NH$_2$ amide), 8.03 (1H, s, HCl), 8.30 (2H, s, NH$_2$ amide).

g) The preparation of N-t-butyloxycarbonyl-β-benzyl-aspartyl-O-benzyl-serine amide, Boc-Asp(OBzl)-Ser(OBzl)-NH$_2$ 2.2 ml (20.0 mmol) N-methylmorpholine in 10 ml DMFA and 4.2 g (10.0 mmol) Boc-Asp(OBzl)-OSu in 20 ml DMFA were added to a solution of 1.85 g (10 mmol) H-Ser(OBzl)-NH$_2$.HCl in 30 ml DMFA under cooling, to 5° C. The reaction mixture was stirred at 20° C. for 48 h. The solvent was distilled off under reduced pressure to ⅕ of the initial volume. The residue was diluted with 100 ml ethyl acetate and acidified under stirring with 50 ml cold 10% citric acid. The mixture was stirred vigorously for 15 min, then the aqueous phase was separated from the organic phase and washed with 50 ml ethyl acetate. The ethyl acetate layers were combined, washed with sat. NaCl, dried over anhydrous Na$_2$SO$_4$ and evaporated. The resulting crystals were taken up in CH$_2$Cl$_2$ and washed successively with 5% NaHCO$_3$ (3×50 ml) and sat. NaCl, dried over anhydrous Na$_2$SO$_4$ and evaporated to yield 3.92 g (78%) of the product in the form of crystals. R$_f$ 0.09 (C), R$_f$ 0.96 (E), R$_f$ 0.93 (I); m.p. 114-117° C.; [α]$^{20}_D$ +17.64° (c=0.01; methanol).

$^1$H NMR (DMSO-d$_6$): 1.35 (9H, s, —CO—O(CH$_3$)$_3$), 2.61 and 2.81 (2H, 2d, C$\underline{H}_2$ Asp), 3.55 and 3.65 (2H, 2d, CH$_2$ Ser), 4.40 (4H, br. s, CH Ser, CH Asp), 4.46 (2H, s, —C$\underline{H}_2$C$_6$H$_5$ Ser(OBzl)), 5.08 (2H, s, —C$\underline{H}_2$C$_6$H$_5$ Asp(OBzl)), 7.27 and 7.43 (2H, 2s, NH$_2$ amide), 7.34 and 7.81 (2H, each d, NH Asp, NH Ser).

h) The preparation of β-benzyl-aspartyl-O-benzyl-serine amide hydrochloride, H-Asp(OBzl)-Ser(OBzl)-NH$_2$.HCl A solution of gaseous HCl in dioxane (~4 M, 50 ml) was added to 3.5 g (7.0 mmol) Boc-Asp(OBzl)-Ser(OBzl)-NH$_2$ at 20° C. The suspension was stirred vigorously at 20° C. for 1.5 h, and the solvent was removed in vacuo. The amorphocrystalline residue was washed successively with ethyl acetate and petroleum ether followed by drying in vacuo to yield 3.0 g (98%) of the product as white crystals. R$_f$ 0.04 (C), R$_f$ 0.68 (E), R$_f$ 0.78 (I); m.p. 147-150° C.; [α]$^{20}_D$ +17.91° (c=0.01; methanol).

$^1$H NMR (DMSO-d$_6$): 2.91 and 3.07 (2H, 2d, CH$_2$ Asp), 3.60 and 3.70 (2H, 2d, CH$_2$ Ser), 4.25 (1H, m, CH Asp), 4.45 (1H, m, CH Ser), 7.30 and 7.55 (2H, 2s, NH$_2$ amide), 8.46 (3H, br. s, NH$_3^+$ Asp), 8.83 (1H, d, NH Ser).

i) The preparation of acetic acid N-oxysuccinimide ester, CH$_3$CO—OSu 2.2 ml (25 mmol) DCCD was added at 5° C. to a solution of 1.43 ml (25 mmol) acetic acid and 2.2 ml (0.25 mmol) N-hydroxysuccinimide in 50 ml dioxane. The reaction mixture was stirred at 20° C. for 20 h. The resulting precipitate was filtered off and washed with dry dioxane. The filtrates were combined and evaporated to yield 3.65 g (93%) of the product as white crystals. R$_f$ 0.41 (C), R$_f$ 0.75 (I); m.p. 103-105° C.

1H NMR (DMSO-d$_6$): 2.34 (3H, s, —CH$_3$CO—), 2.80 (4H, m, —CH$_2$CH$_2$—OSu).

j) The preparation of N-acetyl-β-benzyl-aspartyl-O-benzyl-serine amide, CH$_3$CO-Asp(OBzl)-Ser(OBzl)-NH$_2$ 1.43 ml (13.0 mmol) N-methylmorpholine in 5 ml DMFA and 1.02 g (6.5 mmol) CH$_3$CO—OSu in 15 ml DMFA were added to a solution of 2.83 g (6.5 mmol) H-Asp(OBzl)-Ser(OBzl)-NH$_2$.HCl in 25 ml DMFA under cooling to 5° C. The reaction mixture was stirred at 20° C. for 18 h. The solvent was distilled off under reduced pressure to ⅕ of the initial volume. The residue was diluted with 100 ml ethyl acetate and acidified under stirring with 50 ml cold 10% citric acid. The mixture was stirred vigorously for 15 min, then the aqueous phase was separated from the organic phase and washed with 50 ml ethyl acetate. The ethyl acetate layers were combined, washed with sat. NaCl, dried over anhydrous Na$_2$SO$_4$ and evaporated. The resulting crystalline mass was washed successively with diethyl ether and petroleum ether and dried in vacuo to yield 1.9 g (66%) of the product. R$_f$ 0.0 (C), R$_f$ 0.79 (E), R$_f$ 0.81 (I); m.p. 158-160° C.; [α]$^{20}_D$ -7.26° (c=0.01; methanol).

$^1$H NMR (DMSO-d$_6$): 1.82 (3H, s, CH$_3$CO—), 2.61 and 2.84 (2H, 2d, CH$_2$ Asp), 3.58 and 3.66 (2H, 2d, CH$_2$ Ser), 4.38 (1H, m, CH Ser), 4.47 (2H, s, —CH$_2$C$_6$H$_5$ Ser(OBzl)), 4.73 (1H, m, CH Asp), 5.09 (2H, s, —CH$_2$C$_6$H$_5$ Asp(OBzl)), 7.24 and 7.40 (2H, 2s, NH$_2$ amide), 7.26 and 7.47 (10H, m, 2 —CH$_2$C$_6$H$_5$), 8.0 (1H, d, NH Ser), 8.33 (1H, d, NH Asp).

k) The preparation of N-acetyl-aspartyl-serine amide, CH$_3$CO-Asp-Ser-NH$_2$ (GBK-108

5 ml cyclohexene was added to a solution of 1.77 g (4.0 mmol) CH$_3$CO-Asp(OBzl)-Ser(OBzl)-NH$_2$ in 25 ml ethanol followed by the addition of 1.0 g 10% Pd/C under vigorous stirring at 20° C. The reaction mixture was heated to reflux for 2 h, then cooled to 20° C. The catalyst was filtered off, and the solvent was removed in vacuo. The residue was washed with petroleum ether and dried in vacuo to yield 993 mg (95%, total recovery 11.4%) of the product. R$_f$ 0.0 (C), R$_f$ 0.57 (E), R$_f$ 0.24 (I); m.p. 168-169° C.; [α]$^{20}_D$ -46.36° (c=0.01; methanol). C$_9$H$_{15}$N$_3$O$_6$.

$^1$H NMR (DMSO-d$_6$): 1.84 (3H, s, CH$_3$CO—), 2.47 and 2.68 (2H, 2d, CH$_2$ Asp), 3.54 and 3.62 (2H, 2d, CH$_2$ Ser), 4.11 (1H, m, CH Ser), 4.52 (1H, m, CH Asp), 7.15 and 7.19 (2H, 2s, NH$_2$ amide), 7.82 (1H, d, NH Ser), 8.25 (1H, d, NH Asp).

Example 17

The synthesis of N-acetyl-aspartyl-methionine amide, CH$_3$CO-Asp-Met-NH$_2$ (GBK-201)

a) The preparation of N-t-butyloxycarbonyl-methionine, Boc-Met-OH 2.5 g HaHCO$_3$ in 25 ml water and 14.25 g (65.3 mmol) Boc$_2$O in 50 ml isopropanol were added to a solution of 7.46 g (50.0 mmol) H-Met-OH in 50 ml 1N NaOH. The reaction mixture was stirred vigorously at 20° C. for 2 h, diluted with water to 250 ml and washed with petroleum ether. The aqueous phase was acidified to pH 3-3.5 with citric acid and washed with ethyl acetate (3×100 ml). The combined organic layers were washed with sat. NaCl, dried over anhydrous Na$_2$SO$_4$ and evaporated to yield 10.85 g (87%) of the product. M.p. 135-137° C.

b) The preparation of N-t-butyloxycarbonyl-methionine N-oxysuccinimide ester, Boc-Met-OSu 5.67 g (27.5 mmol) DCCD in 20 ml THF cooled to 0° C. was added to a solution of 5.88 g (25.0 mmol) Boc-Met-OH and 3.165 g (27.5 mmol) N-hydroxysuccinimide in 60 ml of cold THF under vigorous stirring. The reaction mixture was stirred at 0° C. for 18 h. The precipitate was filtered off, and the filtrate was evaporated. The oily residue was dissolved in 40 ml CH$_2$Cl$_2$ and allowed to stand at 0° C. for 24 h. The resulting crystals were filtered off, and the filtrate was evaporated to give a crystalline product in a quantitative yield.

c) The preparation of N-t-butyloxycarbonyl-methionine amide, Boc-Met-NH$_2$ 7.0 ml conc. NH$_4$OH was added under vigorous stirring to a solution of 8.31 g (25 mmol) Boc-Met-OSu in 125 ml DMFA cooled to 0° C. The resulting suspension was stirred vigorously at 0° C. for 24 h. The precipitate was filtered off, and the filtrate was cooled to 0° C. and acidified under stirring to pH ~7 with 50-55 ml 10% citric acid. The solution was evaporated under reduced pressure to ⅕ of the initial volume. The residue was diluted with 100 ml CH$_2$Cl$_2$ and washed successively with 10% NaHCO$_3$ (3×50 ml) and sat. NaCl (3×50 ml). The organic phase was dried over anhydrous Na$_2$SO$_4$ and evaporated. The resulting crystalline mass was washed successively with diethyl ether and petroleum ether and dried in vacuo to yield 4.53 g (73%) of the product. R$_f$ 0.17 (C), R$_f$ 0.88 (E), R$_f$ 0.85 (I); m.p. 120-121° C.; [α]$^{20}_D$ +20.16° (c=0.01; methanol).

d) The preparation of methionine amide hydrochloride, H-Met-NH$_2$.HCl

A solution of gaseous HCl in dioxane (~4 M, 50 ml) was added to 4.4 g (17.7 mmol) Boc-Met-NH$_2$. The solution was stirred vigorously at 20° C. for 1.5 h, and the solvent was removed in vacuo. The resulting crystalline residue was washed successively with diethyl ether, CH$_2$Cl$_2$, and petroleum ether and dried in vacuo to yield 3.2 g (98%) of the product as white crystals. R$_f$ 0.0 (C), R$_f$ 0.43 (E), R$_f$ 0.22 (I); m.p. 193-198° C.; [α]$^{20}_D$ +89.93° (c=0.01; methanol).

e) The preparation of N-t-butyloxycarbonyl-β-benzyl-aspartyl-methionine amide, Boc-Asp(OBzl)-Met-NH$_2$ 2.2 ml (20.0 mmol) N-methylmorpholine in 10 ml DMFA and 4.2 g (10.0 mmol) Boc-Asp(OBzl)-OSu in 30 ml DMFA were added to a solution of 1.85 g (10 mmol) H-Met-NH$_2$.HCl in 30 ml DMFA cooled to 5° C. The reaction mixture was stirred at 20° C. for 48 h. The solution was concentrated under reduced pressure to ⅕ of the initial volume. The residue was diluted with 100 ml ethyl acetate and acidified under stirring with 50 ml cold 10% citric acid. The mixture was stirred vigorously for 15 min, then the aqueous phase was separated from the organic phase and washed with 50 ml ethyl acetate. The ethyl acetate layers were combined, washed with sat. NaCl, dried over anhydrous $Na_2SO_4$ and evaporated. The resulting crystals were taken up in $CH_2Cl_2$ and washed successively with 5% $NaHCO_3$ (3×50 ml) and sat. NaCl, dried over anhydrous $Na_2SO_4$ and evaporated to yield 3.32 g (73%) of the product. $R_f$ 0.17 (C), $R_f$ 0.94 (E), $R_f$ 0.87 (I); m.p. 132-134° C.; $[\alpha]^{20}_D$ −28.26° (c=0.01; methanol).

f) The preparation of 3-benzyl-aspartyl-methionine amide hydrochloride, H-Asp(OBzl)-Met-$NH_2$.HCl A solution of gaseous HCl in dioxane (~4 M, 50 ml) was added to 3.15 g (7.0 mmol) Boc-Asp(OBzl)-Met-$NH_2$ at 20° C. The reaction mixture was stirred vigorously at 20° C. for 1.5 h and evaporated. The amorpho-crystalline residue was washed successively with ethyl acetate and petroleum ether and dried in vacuo to yield 2.65 g (97%) of the product as white crystals. $R_f$ 0.04 (C), $R_f$ 0.68 (E), $R_f$ 0.74 (I); $[\alpha]^{20}_D$ +4.8° (c=0.01; methanol).

g) The preparation of N-acetyl-β-benzyl-aspartyl-methionine amide, $CH_3CO$-Asp(OBzl)-Met-$NH_2$ 1.43 ml (13.0 mmol) N-methylmorpholine in 5 ml DMFA and 1.02 g (6.5 mmol) $CH_3CO$—OSu (for which the synthesis is described in Example 16, section i) in 15 ml DMFA were added to a solution of 2.54 g (6.5 mmol) H-Asp(OBzl)-Ser(OBzl)-$NH_2$.HCl in 25 ml DMFA cooled to 5° C. The reaction mixture was stirred at 20° C. for 18 h. The solution was concentrated under reduced pressure to ⅕ of the initial volume. The residue was diluted with 100 ml ethyl acetate and acidified with 50 ml cold 10% citric acid. The mixture was stirred vigorously for 15 min, then the aqueous phase was separated from the organic phase and washed with 50 ml ethyl acetate. The organic layers were combined, washed with sat. NaCl, dried over anhydrous $Na_2SO_4$ and evaporated. The resulting crystalline mass was washed successively with diethyl ether and petroleum ether and dried in vacuo to yield 1.25 g (49%) of the product. $R_f$ 0.02 (C), $R_f$ 0.80 (E), $R_f$ 0.86 (I); m.p. 142-144° C.; $[\alpha]^{20}_D$ −16.39° (c=0.01; methanol).

h) The preparation of N-acetyl-aspartyl-methionine amide, $CH_3CO$-Asp-Met-$NH_2$ (GBK-201)

30 mg 10% Pd/C was added to a solution of 30 mg (0.0759 mmol) $CH_3CO$-Asp(OBzl)-Met-$NH_2$ in 30 ml methanol and stirred under hydrogen for 7 days constantly adding new portions of the catalyst (10-30 mg each 3-4 times daily). When the reaction was complete (TLC control), the catalyst was filtered off, and the solvent was evaporated to yield 24 mg (87%, total recovery 18.8%) of the product as a crystalline solid. $R_f$ 0.53 (E). $C_{11}H_{19}N_3O_5S$.

$^1$H NMR (DMSO-$d_6$): 1.52 and 1.67 (2H, 2m, $C^\beta H_2$ Met), 1.83 (3H, s, $CH_3CO$—), 1.83 (3H, s, —$SCH_3$ Met), 2.33 (2H, m, $C^\gamma H_2$ Met), 2.58 and 2.76 (2H, 2m, $CH_2$ Asp), 4.06 (1H, m, $C^\alpha H$ Met), 4.8 (1H, m, CH Asp), 7.08 and 7.29 (2H, 2s, $NH_2$ amide), 7.80 (1H, d, NH Met), 8.29 (1H, d, NH Asp).

Example 18

The synthesis of bis-(N-monosuccinyl-glycyl-lysine) hexamethylenediamine, $(HOOC(CH_2)_2CO$-Gly-Lys-$NH)_2$—$(CH_2)_6$ (GK-2w)

a) The preparation of N-benzyloxycarbonyl-$N^\epsilon$-t-butyloxycarbonyl-lysine dicyclohexylammonium salt, Z-Lys(Boc)-OH.DCHA To a solution of 182.6 g (1 mol) lysine hydrochloride in 1000 ml water under stirring first 137.3 g (0.55 mol) $CuSO_4.5H_2O$ dissolved in 600 ml hot water was added followed by conc. NaOH to pH ~9 and followed by the addition of 229 g (1.05 mol) $Boc_2O$ dissolved in a small volume of isopropanol. The reaction mix was stirred at 33-35° C. for 12 h while keeping the pH at ~9 with NaOH. When the starting compound disappeared (TLC control), 206 g EDTA was added at 40-50° C. as an aqueous suspension adjusted to pH ~10 with NaOH. The reaction mix was cooled to room temperature and 133 g (0.7 mol) Z—Cl dissolved in a small volume of water was added dropwise. When H-Lys(Boc)-OH disappeared (TLC control), 1500 ml ethyl acetate was added to the reaction mix and acidified to pH ~3 with conc. HCl, and the $CuSO_4$ was filtered off. The organic layer was washed with water and evaporated. The residue was taken up in 1800 ml diethyl ether and 0.9 mol DCHA was added to crystallize the product in the form of a dicyclohexylammonium salt to yield 294.5 g (0.525 mol, 52.5%) of the product as white crystals. The product was used in the next step without further characterization.

b) The preparation of N-benzyloxycarbonyl-$N^\epsilon$-t-butyloxycarbonyl-lysine N-oxysuccinimide ester, Z-Lys(Boc)-OSu A solution of 294 g (0.525 mol) Z-Lys(Boc)-OH.DCHA in 500 ml ethyl acetate was stirred with 0.6 mol $H_2SO_4$ (5% solution) for 30 min, then the organic layer was separated and the ethyl acetate was evaporated. The residue was dissolved in 1000 ml ethyl acetate and 65.5 g (0.57 mol) HOSu and 185 g (0.9 mol) DCCD were added. The reaction mix was stirred at room temperature for 12 h. When the starting compound disappeared (TLC control), the precipitated dicyclohexylurea was filtered off, and the solvent was removed in vacuo. The resulting oil was recrystallized from a mixture of 150 ml isopropanol and 1.5 l diethyl ether (1:10) to yield 225.7 g (0.473 mol, 90%) of the product as a white crystalline solid. $R_f$ 0.90 (A), $R_f$ 0.83 (B); m.p. 118-122° C.; $[\alpha]^{25}_D$ −20.66° (c=0.41; ethanol).

$^1$H NMR (DMSO-$d_6$): 1.18-1.92 (6H, m, $C^\beta H_2 C^\gamma H_2 C^\delta H_2$ Lys), 1.35 (9H, s, —$C(CH_3)_3$ Boc), 2.79 (4H, m, —$CH_2$—$CH_2$— Su), 2.85-3.04 (2H, m, $C^\epsilon H_2$ Lys), 4.39 (1H, m, $C^\alpha H$ Lys), 5.05 (2H, s, $OCH_2Z$), 6.78 (1H, t, $N^\epsilon H$ Lys), 7.34 (5H, m, $C_6H_5Z$), 7.97-8.12 (1H, d, $N^\alpha H$ Lys).

c) The preparation of bis-(N-benzyloxycarbonyl-$N^\epsilon$-t-butyloxycarbonyl-lysyl) hexamethylenediamide, (Z-Lys(Boc)-$NH)_2$—$(CH_2)_6$ A solution of 2.575 g (5.4 mmol) Z-Lys(Boc)-OSu and 0.299 g (2.6 mmol) hexa-methylenediamine in 14 ml dimethylformamide was stirred at room temperature for 4 h, forming a cloudy solution. The reaction mixture was diluted with 56 ml water and allowed to stand for a few hours. The solidified precipitate was filtered off, washed with water and dried over $P_2O_5$ to yield 2.085 g (96%) of a white crystalline product. $R_f$ 0.90 (A), $R_f$ 0.93 (B); m.p. 138-147° C.; $[\alpha]^{25}_D$ −9.31° (c=0.29; ethanol).

$^1$H NMR (DMSO-$d_6$): 1.05-1.69 (12H, m, 2 $C^\beta H_2$, 2 $C^\gamma H_2$, 2 $C^\delta H_2$ Lys; 8H, m, —$NHCH_2CH_2CH_2CH_2CH_2CH_2NH$—), 1.35 (18H, s, 2 —$C(CH_3)_3$ Boc), 2.87 (4H, m, $2C^\epsilon H_2$ Lys), 3.01 (4H, m, —$NHCH_2CH_2CH_2CH_2CH_2CH_2NH$—), 3.89 (2H, m, 2 $C^\alpha H$ Lys), 5.01 (4H, s, 2 $OCH_2Z$), 6.74 (2H, t, $NHCH_2CH_2CH_2CH_2CH_2CH_2NH$—), 7.13-7.39 (10H, m, 2 $C_6H_5Z$; 2H, d, 2 $N^\alpha H$ Lys), 7.81 (2H, t, 2 $N^\epsilon H$ Lys).

d) The preparation of bis-($N^\epsilon$-t-butyloxycarbonyl-lysyl) hexamethylenediamide, (H-Lys(Boc)-$NH)_2$—$(CH_2)_6$ 1.86 g (2.2 mmol) (Z-Lys(Boc)-$NH)_2$—$(CH_2)_6$ in 25 ml methanol was hydrogenated using 10% Pd/C (0.37 g) at room temperature for 1 h 25 min. When the starting compound disappeared (TLC control), the catalyst was filtered off, and the solvent was removed in vacuo. The resulting oil was dried over $CaCl_2$ and paraffin. It was precipitated with a mixture of petroleum ether and diethyl ether (3:1) and filtered off to yield 0.99 g (78%) of the product as a white powder. $R_f$ 0.48 (A), $R_f$ 0.68 (B); m.p. 70-75° C.; $[\alpha]^{25}_D$ +5.1° (c=1; ethanol).

$^1$H NMR (DMSO-d$_6$): 1.11-1.65 (12H, m, 2 C$^\beta$H$_2$, 2 C$^\gamma$H$_2$, 2 C$^\delta$H$_2$ Lys; 8H, m, —NHCH$_2$CH$_2$CH$_2$CH$_2$CH$_2$CH$_2$NH—; 18H, s, 2 —C(CH$_3$)$_3$ Boc), 2.86 (4H, m, 2 C$^\epsilon$H$_2$ Lys), 3.04 (4H, m, —NHCH$_2$CH$_2$CH$_2$CH$_2$CH$_2$CH$_2$NH—), 3.40 (2H, m, 2 C$^\alpha$H Lys), 6.73 (2H, t, 2 N$^\epsilon$H Lys), 7.78 (2H, t, —NHCH$_2$CH$_2$CH$_2$CH$_2$CH$_2$CH$_2$NH—).

e) The preparation of N-benzyloxycarbonyl-glycine N-oxysuccinimide ester, Z-Gly-OSu 3.22 g (28 mmol) HOSu and 6.36 g (28 mmol) DCCD were added to a solution of 5.28 g (28 mmol) Z-Gly-OH in 80 ml ethyl acetate. The reaction mix was stirred at 10° C. for 2 h. When the starting compound disappeared (TLC control), the precipitated dicyclohexylurea was filtered off, and the solvent was removed in vacuo. The resulting oil was recrystallized from a mixture of 3 ml petroleum ether and 8 ml chloroform to yield 5.87 g (80%) of the product as a white crystalline solid.

f) The preparation of bis-(N-benzyloxycarbonyl-glycyl-N$^\epsilon$-t-butyloxycarbonyl-lysine) hexamethylenediamide, (Z-Gly-Lys(Boc)-NH)$_2$—(CH$_2$)$_6$ 1.103 g (3.8 mmol) Z-Gly-OSu dissolved in 4 ml DMFA was added dropwise to a solution of 0.90 g (1.6 mmol) (H-Lys(Boc)-NH)$_2$—(CH$_2$)$_6$ in 6 ml DMFA and was stirred at room temperature for 2 h 10 min (TLC control). 1.5 ml diethylpropyldiamine was added to the reaction mixture and stirred for a further 30 min followed by the dilution with 70 ml water. The product containing organic impurities was extracted in chloroform (3:1) and washed successively with 25 ml water, 25 ml 2% H$_2$SO$_4$, and 25 ml 3% Na$_2$CO$_3$. The solution was dried over MgSO$_4$ and filtered. The chloroform was evaporated resulting in a mixture of yellowish oil with white crystals. It was recrystallized from diethyl ether (20 ml) to yield 1.26 g (84%) of the product as a white powder. $R_f$ 0.89 (A), $R_f$ 0.95 (B); m.p. 120-126° C.; $[\alpha]^{25}_D$ −11.0° (c=0.1; ethanol).

$^1$H NMR (DMSO-d$_6$): 1.05-1.70 (12H, m, 2 C$^\beta$H$_2$, 2 C$^\gamma$H$_2$, 2 C$^\delta$H$_2$ Lys; 8H, m, —NHCH$_2$CH$_2$CH$_2$CH$_2$CH$_2$NH—), 1.35 (18H, s, 2 —C(CH$_3$)$_3$ Boc), 2.85 (4H, m, 2C$^\epsilon$H$_2$ Lys), 3.00 (4H, m, —NHCH$_2$CH$_2$CH$_2$CH$_2$CH$_2$CH$_2$NH—), 3.65 (4H, d, 2 CH$_2$ Gly), 4.15 (2H, m, 2 C$^\alpha$H Lys), 5.03 (4H, s, 2 OCH$_2$Z), 7.25 (2H, t, —NHCH$_2$CH$_2$CH$_2$CH$_2$CH$_2$CH$_2$NH—), 7.14-7.37 (10H, m, 2 C$_6$H$_5$Z; 2 N$^\alpha$H Lys), 7.81 (2H, t, 2 N$^\epsilon$H Lys).

g) The preparation of bis-(glycyl-N$^\epsilon$-t-butyloxycarbonyl-lysine) hexamethylenediamide, (H-Gly-Lys(Boc)-NH)$_2$—(CH$_2$)$_6$ 1.17 g (1.2 mmol) (Z-Gly-Lys(Boc)-NH)$_2$—(CH$_2$)$_6$ in 20 ml methanol was hydrogenated using 10% Pd/C (0.23 g) at room temperature for 20 min. When the starting compound disappeared (TLC control), the catalyst was filtered off, and the solvent was removed in vacuo. The resulting oil was precipitated with diethyl ether (20 ml) and filtered off. The product as a white powder was used in the next step without further purification.

h) The preparation of bis-(N-monosuccinyl-glycyl-N$^\epsilon$-t-butyloxycarbonyl-lysine) hexamethylenediamide, (HOOC(CH$_2$)$_2$CO-Gly-Lys(Boc)-NH)$_2$—(CH$_2$)$_6$ 0.24 g (2.4 mmol) succinic anhydride was added to a solution of (H-Gly-Lys(Boc)-NH)$_2$—(CH$_2$)$_6$ in 5 ml DMFA. The reaction mixture was stirred at room temperature for 4 h until the reaction was complete (TLC control). Then the reaction mixture was diluted with 20 ml ethyl acetate and 15 ml water. 5 ml 3% Na$_2$CO$_3$ was added to the DMFA/water fraction and saturated with 1.5 g Na$_2$SO$_4$, then 15 ml butanol was added and 10% H$_2$SO$_4$ to pH ~3. The solution was washed with 10% Na$_2$SO$_4$, and the solvent was evaporated completely. The residue was triturated with diethyl ether and filtered off to yield 0.872 g (82%) of the product as a white powder. $R_f$ 0.80 (A), $R_f$ 0.67 (B); m.p. 86-92° C.; $[\alpha]^{25}_D$ −10.4° (c=1; ethanol).

$^1$H NMR (DMSO-d$_6$): 1.11-1.75 (12H, m, 2 C$^\beta$H$_2$, 2 C$^\gamma$H$_2$, 2 C$^\delta$H$_2$ Lys; 8H, m, —NHCH$_2$CH$_2$CH$_2$CH$_2$CH$_2$NH—; 1.35 (18H, s, 2 —C(CH$_3$)$_3$ Boc), 2.36 (4H, m, 2 CH$_2$ Suc), 2.72 (4H, m, 2 C$^\epsilon$H$_2$ Lys), 2.96 (4H, m, —NHCH$_2$CH$_2$CH$_2$CH$_2$CH$_2$CH$_2$NH—), 3.65 (4H, s, 2 CH$_2$ Gly), 4.10 (2H, m, 2 C$^\alpha$H Lys), 6.71 (2H, t, —NHCH$_2$CH$_2$CH$_2$CH$_2$CH$_2$CH$_2$NH—), 7.83 (2H, t, 2 N$^\epsilon$H Lys), 8.13 (2H, d, 2 N$^\alpha$H Lys), 8.87 (2H, t, 2 NH Gly). 2 HOOC(CH$_2$)$_2$CO— are exchangeable with HDO.

i) The preparation of bis-(N-monosuccinyl-glycyl-lysine) hexamethylenediamide, (HOOC(CH$_2$)$_2$CO-Gly-Lys-NH)$_2$—(CH$_2$)$_6$ All the (HOOC(CH$_2$)$_2$CO-Gly-Lys(Boc)-NH)$_2$—(CH$_2$)$_6$ was dissolved in acetic acid and treated with 3 ml 4M HCl/dioxane for 40 min. Then the solvent was decanted, and the residue was washed with diethyl ether by decantation, dissolved in 5 ml water and treated with an Amberlite IRA-410 resin under stirring until the pH was ~5. The purification was performed by the C8 reversed phase HPLC using a 0 to 13% isopropanol gradient in 0.1M acetic acid. The relevant fractions were collected (TLC control), evaporated and dried in vacuo. The residue was freeze-dried in liquid nitrogen and recrystallized from an ethyl acetate-ethanol 3:1 mixture to yield 0.515 g (total recovery 29%) of the final product as a white powder. $R_f$ 0.14 (A), $R_f$ 0.38 (B); m.p. 97-100° C.; $[\alpha]^{25}_D$ −15.7° (c=1; water).

$^1$H NMR (DMSO-d$_6$): 1.06-1.85 (12H, m, 2 C$^\beta$H$_2$, 2 C$^\gamma$H$_2$, 2 C$^\delta$H$_2$ Lys; 8H, m, —NHCH$_2$CH$_2$CH$_2$CH$_2$CH$_2$NH—; 1.35 (18H, s, 2 —C(CH$_3$)$_3$ Boc), 2.26 (4H, m, 2 CH$_2$ Suc), 2.84 (4H, m, 2 C$^\epsilon$H$_2$ Lys), 3.05 (4H, m, —NHCH$_2$CH$_2$CH$_2$CH$_2$CH$_2$CH$_2$NH—), 3.69 (4H, s, 2 CH$_2$ Gly), 4.10 (2H, m, 2 C$^\alpha$H Lys), 7.65 (2H, t, —NHCH$_2$CH$_2$CH$_2$CH$_2$CH$_2$CH$_2$NH—), 8.34 (2H, d, 2 N$^\alpha$H Lys), 8.64 (2H, t, 2 N$^\epsilon$H Gly). 2 HOOC(CH$_2$)$_2$CO— are exchangeable with HDO.

I. Biological Characterization of the Claimed Compounds In Vitro

Materials and Methods

Materials

Culture flasks, tubes, microplates were from either Corning or Costar. DMEM growth medium, Hank's medium, fetal calf serum (FBS), phosphate-buffered saline (PBS), poly-L-lysine, 3-(4,5-dimethylthiazol-2-yl)-2,5-tetrazolium hydrobromide (MTT), dimethylsulfoxide (DMSO) were from ICN. 130 kDa Nerve growth factor from the mouse submandibular gland (NGF-7s) was from Sigma. Tris-HCl was from Serva, and dithiothreitol, sodium dodecylsulfate (SDS), Tween-20, TEMED, acrylamide, methylene bis-acrylamide all were from BioRad. The protease inhibitor mix was from Biomol, Folin reagent from Merck, 1-methyl-4-phenyl-1,2,3,6-tetrahydropyridine (MPTP) from Sigma, electrochemiluminescent reagent ECL from Santa Cruz Biotechnology.

The primary goat polyclonal anti-rat Hsp32 (hemoxygenase-1) antibody M-19 and mouse monoclonal anti-HeLa cell-derived Hsp70 antibody W27 were from Stressgen. The primary mouse monoclonal anti-rat phosphorylated tyrosine kinase A (pTrkA) antibody E6, the secondary horseradish peroxidase conjugated goat monoclonal anti-mouse antibody, and the secondary horseradish peroxidase conjugated goat polyclonal anti-rabbit antibody all were from Santa Cruz Biotechnology. The electrophoresis Mini-Protean 2Cell apparatus and the Semi-dry protein transfer onto PVDF membranes apparatus were from BioRad.

Methods

Cultured Cells

PC12 and HT-22 Cell Cultures

The rat adrenal cortex pheochromocytoma cell line PC12 was obtained from the Cell Culture Museum, RAN Institute of Molecular Genetics. The immortalized mouse hippocampal cell line HT-22 was a gift from Prof. F. Viegant, Utrecht University, the Netherlands.

The cells were grown in DMEM medium containing 5% FBS and 2 mM L-glutamine. The cells were incubated at 37° C. and 5% $CO_2$. The growth medium was changed at 24 hours after inoculation and every 3 days thereafter. The cells were re-plated every week into culture flasks with a total area of 75 $cm^2$.

The Isolation and Growth of Midbrain and Hippocampal Neurons from Rat Embryos

Eighteen days old embryos from MR (Maudsley reactive) rats were used for experiments. The dissection of the brain and the excision of midbrain and hippocampal neurons were carried out in Hank's medium. The isolated neurons were then transferred into centrifuge tubes with DMEM/F-12 medium, resuspended and centrifuged at 1500 rpm for 10 min. The supernatant was poured off, 2 ml DMEM/F-12 was added and re-centrifuged using the same conditions. The procedure for medium exchange was repeated once more, the cells were resuspended, counted and re-plated in 48-well culture plates at a density of 350-400 thousand cells per well.

Preparation of Culture Plates

The experiments employed 96-, 48-, and 6-well culture plates. The wells were treated with poly-L-lysine (0.1 mg/ml) in sterile deionized water (µQ, Millipore) for 30 min followed by washing with sterile water (3×) and drying in a laminar flow box at room temperature.

Cell Plating for Experiments

PC12 and HT-22 cells were seeded in 96-well plates at a density of $3.5 \times 10^3$ per well and in 6-well plates at a density of $500 \times 10^3$ per well. Midbrain and hippocampal neurons were seeded in 48-well culture plates at a density of $350 \times 10^3$ cells per well. All types of cells were plated in DMEM medium. For PC12 and HT-22 cell lines, 5% FBS was added, and for embryonic neuron cultures, 10% FBS was added. The experiments employed cell lines at 3 days after passage and embryonic neuronal cells at 6 days after passage. The cells were grown to confluence, to form a monolayer.

The Production of Differentiated PC 12 Cells for Experiments

The cells were plated at a density of $3.5 \times 10^3$ per well in DMEM with 5% FBS. NGF (100 ng/ml) was added at the time of plating and every 48 hours thereafter. All the experiments using differentiated PC12 cells were performed at day 6 of growth.

The Study of the Ability of Low Molecular Weight Peptide Mimetics of NGF to Induce PC12 Cell Differentiation Undifferentiated PC12 cells were plated at a density of $3.5 \times 10^3$ per well in DMEM with 1% FBS. At the time of plating, either NGF (100 ng/ml, positive control) or a test compound was added to a final concentration of $10^{-5}$ to $10^{-9}$ M in the growth medium. Thereafter, the test peptides and NGF were added to the medium every 24 hours in one series of experiments and every 48 hours in another series, for a total of 6 days. The extent of cell differentiation was estimated on the basis of the shape and size of the cells and the number and length of the processes.

Oxidative Stress Model

To induce an oxidative stress, the cells were placed in a growth medium containing 5% FBS, then a freshly prepared $H_2O_2$ solution was added to a final concentration of 1.5 mM and incubated for 30 min at 37° C. and 5% $CO_2$. Thereafter, the medium was replaced with a new one and the cells were cultured for 4 h under the same conditions.

Parkinson's Disease Model Using PC12 Cell Line

To produce a model for Parkinson's disease, MPTP was used at a final concentration of 1 mM (Shimoke K., Chiba H. Nerve growth factor prevents 1-methyl-1,4-phenyl-1,2,3,6-tetrahydropyridine-induced cell death via the Akt pathway by suppressing caspase-3-like activity using PC12 cells: relevance to therapeutic application for Parkinson's disease. J. Neurosci. Res. 2001, 63, 402-409). MPTP was added to the cell growth medium containing 1% FBS at 24 hours after passage. The peptides were added to the cell growth medium concurrently with MPTP or 24 h before MPTP. Cell viability was determined at 24 h using an MTT test.

Determination of Cultured Cell Viability

The determination of cell viability was carried out by MTT test. MTT is a water soluble tetrazolium salt of yellow color which readily permeates cells. In living cells, MTT is converted into water insoluble formazan crystals of violet color. At the end of an experiment the growth medium was replaced with an MTT solution (0.5 mg/ml) and incubated for 30 min at 37° C. and 5% $CO_2$. The MTT solution was then removed from the wells and DMSO was added to dissolve the formazan precipitate. Then the optical density was measured using a Multiscan (Thermo) spectrophotometer at a wavelength of 600 nm.

Western Blotting Procedure

The amount of Hsp70, Hsp32 and pTrkA was determined in the cytoplasmic fraction of HT-22 neuronal cells. For heat shock proteins, a test compound was added to the culture 24 hours prior to testing, before the cells were washed off the culture liquid with PBS. For pTrkA, a test compound was added to the culture immediately prior to the cell lysis just for 1 or 2 min, before the cells were washed off the culture liquid with PBS. Then the cells were mixed with the lysis buffer (50 mM Tris-HCl, 5 mM EDTA, 1 mM DTT, 1% Triton X-100, pH 7.5) at 4° C. and lysed for 5 min, then scraped off, transferred into a 1.5 ml centrifuge tube and centrifuged at 13000 rpm and 4° C. for 10 min. The supernatant containing cytosolic proteins was assayed by electrophoresis and immunoblotting. Proteins were separated on a 10% polyacrylamide gel (PAAG) and transferred from PAAG onto a PVDF membrane by electroelution for 45 min. Western blots were pre-incubated for 1 h in a TBST solution containing 1% Tween-20 and supplemented with 5% (w/v) skim milk. Western blots were then incubated with the primary polyclonal anti-Hsp32 antibody diluted 1:1000 or primary monoclonal anti-Hsp70 antibody diluted 1:1000 or primary monoclonal anti-phosphorylated tyrosine kinase A antibody diluted 1:1000 for 1 hour. Then the blots were washed and incubated with a secondary antibody conjugated to horseradish peroxidase (diluted 1:2000) for 1 hour. The detection of Hsp70, Hsp32 and pTrkA was carried out by the ECL reaction on a Kodak film.

Statistical data treatment was carried out according to Student's t-test.

Results

1. Differentiation-inducing Activity 1.1. The Effects of NGF Mimetics GK-1 Through GK-5 on the Differentiation of PC12 Cell Line When supplemented with nerve growth factors, PC-12 cells are able to differentiate to a neuronal type, which is the reason behind their use in the studies designed to evaluate the differentiation-inducing activity of various drugs.

The peptides GK-1 through GK-5 were added to a final concentration of $10^{-8}$ to $10^{-5}$ M in the growth medium. NGF was used as a positive control at a final concentration of 100 ng/ml.

The peptide NGF-mimetics GK-1 through GK-4 were found not to induce the differentiation of PC-12 cells at any concentration tested. However, GK-1 at $10^{-5}$ M decreased the differentiation-promoting effect of NGF by 50% (this result was obtained by counting the numbers of differentiated and undifferentiated cells). GK-5 showed a differentiation-promoting effect at $10^{-6}$ M and $10^{-5}$ M.

To study a modulatory potential of the peptides GK-3, GK-4 and GK-5 on the effects of NGF, the peptides were applied at a final concentration of $10^{-6}$ M GK-3, $10^{-7}$ M GK-4, and $10^{-6}$ M GK-5. These peptides at the concentrations studied produced a modulatory action on the differentiation induction by NGF. By measuring the longest processes and their branching points upon a combination of GK-3 and NGF it was found that these values were not significantly different from those found with NGF alone. However, the branching points of these processes were located much further away from the cell body than in the samples with NGF alone (25 µm and 14 µm, respectively), suggesting an increased ability of neurons to regenerate. The effect of GK-3 was observed 4 days after the start of the experiment.

The morphology of the cell population originating from PC12 in the presence of GK-3 and NGF suggested that this peptide may have a beneficial effect on neurons of the peripheral nervous system, in particular, on parasympathetic and sympathetic ganglia as well as on sensory ganglia of the spinal cord. Accordingly, this peptide may be effective in cases where visceral innervation is impaired.

By measuring the longest processes and their branching points upon a combination of GK-4 and NGF it was found that the processes were longer than in the presence of NGF alone (65 µm and 36 µm, respectively). The branching points of these processes were located closer to the cell body than with NGF alone (20 µm and 31 µm, respectively). Upon the combination of GK-4 and NGF mainly three morphological groups of neurons may be singled out in the differentiated cell population: unipolar (trigeminal nerve sensory nucleus), pseudo-unipolar (centered on the spinal cord in intervertebral ganglia) (10%), and intercalary (90%). The central nervous system is by 90% composed of intercalary neurons functioning in the processing and transmitting nerve impulses. One or more intercalary neurons may be present between the afferent (from sensory organs to central parts of the nervous system) and efferent neurons (impulses to organs, such as motor neurons). Their numbers are especially large in the midbrain and hindbrain reticular formation and the basal ganglia. Accordingly, this peptide may be useful in cases where motor functions are impaired in the course of neurodegenerative processes (such as in ischemic and hemorrhagic stroke). Also, there remained some undifferentiated cells. The effect of GK-4 was seen to occur much later than that of GK-3. This is characteristic for the development of intercalary neurons in the so called "embryonal compensation model".

By measuring the longest processes and their branching points upon a combination of GK-5 and NGF it was found that the branching points were not different from those found in the presence of NGF alone but the maximum length of the processes was greater (55 µm and 37 µm, respectively). Therefore, this peptide may be effective in cases where visceral innervation is impaired.

TABLE 1.1

The effects of GK-4 and GK-5 on the differentiation-inducing activity of NGF in PC12 cells

|  | Control | NGF (100 ng/ml) | GK-4 ($10^{-7}$M) + NGF (100 ng/ml) | GK-4 ($10^{-7}$M) + NGF (50 ng/ml) | GK-4 ($10^{-7}$M) + NGF (30 ng/ml) |
|---|---|---|---|---|---|
| Max. length of cell processes, µm on day 6 | 8 ± 0.2 | 36 ± 7.7* | 65 ± 12.2' | 56 ± 13.2' | 52 ± 10.3' |

|  | Control | NGF (100 ng/ml) | GK-4 ($10^{-6}$M) + NGF (100 ng/ml) | GK-4 ($10^{-6}$M) + NGF (50 ng/ml) | GK-4 ($10^{-6}$M) + NGF (30 ng/ml) |
|---|---|---|---|---|---|
| Max. length of cell processes, µm on day 6 | 7 ± 0.6 | 37 ± 7.7* | 55 ± 11.3' | 73 ± 9.5' | 67 ± 4.5' |

*p < 0.05 versus control according to Student's t-test

2. Neuroprotective Activity 2.1. The Effects of Neurotrophin Mimetics on the Viability of HT-22 Neuronal Cell Line GK-2 at concentrations from $10^{-8}$ to $10^{-5}$ M as well as NGF at a concentration of 100 ng/ml added at the time of plating and every 24 hours thereafter for a total of 10 days were found to improve the viability of neurons in the absence of any damaging factors (Table 1.2).

TABLE 1.2

| Group (n = 12) | Optical density |
|---|---|
| Control | 0.283 ± 0.039 |
| NGF, 100 ng/ml | 0.345 ± 0.023* |

TABLE 1.2-continued

| Group (n = 12) | Optical density |
|---|---|
| GK-2, $10^{-5}$M | 0.357 ± 0.051* |
| GK-2, $10^{-8}$M | 0.375 ± 0.063* |

*$p < 0.05$ versus control according to Student's t-test

The NGF mimetic GK-2c reduced the viability of HT-22 cells (FIG. 1.1).

2.2. Characterization of Neuroprotective Effects of the NGF and BDNF Mimetics Using Cultured HT-22 Cell Line Under Oxidative Stress Conditions The claimed compounds affected the viability of hippocampal cells under oxidative stress conditions (Tables 1.3 to 1.8, FIGS. 1 to 5). Thus, the peptides GK-1 and GSB-104 impaired the neuronal survival, whereas the peptides GK-2, GK-2a, GK-2b, GK-2e, GK-2f, GK-3, GK-4, GK-5, GK-6, GSB-106, GSB-104, GBK-108 improved the neuronal survival when added 24 hours prior to the stress exposure in the concentration range of $10^{-8}$ M to $10^{-5}$ M.

TABLE 1.3

| Group (n = 12) | Optical density |
|---|---|
| Control | 0.615 ± 0.073 |
| $H_2O_2$, 1.5 mM | 0.448 ± 0.038* |
| GK-2, $10^{-5}$M | 0.346 ± 0.029^ |
| GK-2, $10^{-8}$M | 0.429 ± 0.060 |
| NGF, 100 ng/ml | 0.449 ± 0.064 |

*$p < 0.05$ versus control,
^$p < 0.05$ versus $H_2O_2$

TABLE 1.4

| Group (n = 12) | Optical density |
|---|---|
| Control | 0.427 ± 0.071 |
| $H_2O_2$, 1.5 mM | 0.350 ± 0.052 |
| GK-2, $10^{-5}$M | 0.422 ± 0.063^ |
| GK-2, $10^{-8}$M | 0.501 ± 0.109^ |
| GK-2, $10^{-9}$M | 0.516 ± 0.068^ |

^$p < 0.05$ versus $H_2O_2$

TABLE 1.5

| Group (n = 12) | Optical density |
|---|---|
| Control | 0.1275 ± 0.021 |
| $H_2O_2$, 1.5 mM | 0.087 ± 0.006* |
| GK-2a, $10^{-5}$M | 0.108 ± 0.019^ |
| GK-2a, $10^{-6}$M | 0.429 ± 0.02 |
| GK-2a, $10^{-7}$M | 0.449 ± 0.024 |
| GK-2a, $10^{-8}$M | 0.106 ± 0.028 |

*$p < 0.05$ versus control,
^$p < 0.05$ versus $H_2O_2$

TABLE 1.6

| Group (n = 12) | Optical density |
|---|---|
| Control | 0.111 ± 0.009 |
| $H_2O_2$, 1.5 mM | 0.093 ± 0.004* |
| NGF, 100 ng/ml | 0.103 ± 0.018 |

TABLE 1.6-continued

| Group (n = 12) | Optical density |
|---|---|
| GK-3, $10^{-5}$M | 0.109 ± 0.019 |
| GK-3, $10^{-6}$M | 0.110 ± 0.014^ |
| GK-3, $10^{-7}$M | 0.099 ± 0.014 |
| GK-3, $10^{-8}$M | 0.091 ± 0.014 |

*$p < 0.05$ versus control,
^$p < 0.05$ versus $H_2O_2$

TABLE 1.7

| Group (n = 12) | Optical density |
|---|---|
| Control | 0.123 ± 0.013 |
| $H_2O_2$, 1.5 mM | 0.097 ± 0.017* |
| NGF, 100 ng/ml | 0.103 ± 0.018 |
| GK-4, $10^{-5}$M | 0.104 ± 0.015 |
| GK-4, $10^{-6}$M | 0.101 ± 0.009 |
| GK-4, $10^{-7}$M | 0.109 ± 0.014^ |
| GK-4, $10^{-8}$M | 0.104 ± 0.016 |

*$p < 0.05$ versus control,
^$p < 0.05$ versus $H_2O_2$

TABLE 1.8

| Group (n = 12) | Optical density |
|---|---|
| Control | 0.097 ± 0.009 |
| $H_2O_2$, 1.5 mM | 0.056 ± 0.009* |
| NGF, 100 ng/ml | 0.071 ± 0.009^ |
| GK-5, $10^{-5}$M | 0.065 ± 0.008 |
| GK-5, $10^{-6}$M | 0.066 ± 0.008^ |
| GK-5, $10^{-7}$M | 0.062 ± 0.009 |
| GK-5, $10^{-8}$M | 0.058 ± 0.007 |

*$p < 0.05$ versus control,
^$p < 0.05$ versus $H_2O_2$

An experiment was conducted where the peptide GK-2 was added immediately after the oxidative stress exposure (Table 1.9). GK-2 demonstrated a therapeutic effect at concentrations between $10^{-8}$ M and $10^{-5}$ M.

TABLE 1.9

The effects of different concentrations of GK-2 added after the oxidative stress on the survival of cultured HT-22 cells

| Group (n = 12) | Optical density |
|---|---|
| Control | 0.344 ± 0.104 |
| $H_2O_2$, 1.5 mM | 0.247 ± 0.015* |
| GK-2, $10^{-5}$M | 0.324 ± 0.070^ |
| GK-2, $10^{-8}$M | 0.345 ± 0.065^ |

*$p < 0.05$ versus control,
^$p < 0.05$ versus $H_2O_2$

When added 30 minutes before GK-2, GK-1 ($10^{-5}$ M) eliminated the neuroprotective effect of GK-2.

2.3. Evaluation of Neuroprotective Effects of GK-2 Using Cultured Midbrain and Hippocampal Neurons from 18 Days-old Rat Embryos Under Oxidative Stress Conditions At a concentration of $10^{-5}$ M, GK-2 was active in primary cultures of midbrain and hippocampal neurons from 18 days-old rat embryos in an oxidative stress model when added 24 hours before the stress exposure (Tables 1.10, 1.11).

TABLE 1.10

The effects of peptide GK-2 on the survival of cultured midbrain
neurons from 18 days-old rat embryos after the oxidative stress

| Group (n = 12) | Optical density |
|---|---|
| Control | 0.497 ± 0.006 |
| H$_2$O$_2$, 1.5 mM | 0.475 ± 0.007* |
| GK-2, 10$^{-5}$M | 0.493 ± 0.005^ |
| GK-2, 10$^{-8}$M | 0.498 ± 0.014 |

*p < 0.05 versus control,
^p < 0.05 versus H$_2$O$_2$

TABLE 1.11

The effects of peptide GK-2 on the survival of cultured hippocampal
neurons from 18 days-old rat embryos after the oxidative stress

| Group (n = 12) | Optical density |
|---|---|
| Control | 0.490 ± 0.004 |
| H$_2$O$_2$, 1.5 mM | 0.480 ± 0.007 |
| GK-2, 10$^{-5}$M | 0.515 ± 0.006^ |
| GK-2, 10$^{-8}$M | 0.503 ± 0.005 |

^p < 0.05 versus H$_2$O$_2$

The results obtained show that the peptide GK-2 has a neuroprotective effect with respect to embryonic hippocampal and midbrain neurons.

2.4. The Activity of GK-2, GK-2a, GK-3, GK-4, and GK-5 in a Cellular Model of Parkinson's Disease GK-2 had a significant protective effect in a cellular model of Parkinson's disease. This effect was displayed only at 10$^{-5}$ M when GK-2 was added concurrently with MPTP, however, when added 24 hours prior to MPTP, it was active at both 10$^{-5}$ M and 10$^{-8}$ M (FIGS. 1.9, 1.10). The peptides GK-2a, GK-3, and GK-4, when added 24 hours prior to MPTP, also had a protective effect in this model of Parkinson's disease (FIG. 1.11). The peptide GK-5 was inactive in this test.

2.5. The Protective Effect of the Claimed Compounds Against Glutamate Cytotoxicity in Cultured HT-22 Cells The peptides GK-2, GK-4 and GSB-106 demonstrated a protective effect against glutamate cytotoxicity in cultured HT-22 cells when added 24 hours prior to glutamate (FIG. 1.12, Table 1.12). The BDNF mimetic GSB-106 was active in the concentration range of 10$^{-8}$ M to 10$^{-5}$ M, with its effect increasing in extent with decreasing concentrations.

TABLE 1.2

| Group (n = 12) | Optical density |
|---|---|
| Control | 0.178 ± 0.010 |
| Glutamate | 0.145 ± 0.013* |
| GK-2, 10$^{-8}$M | 0.179 ± 0.007^ |
| GK-4, 10$^{-7}$M | 0.163 ± 0.008^ |

*p < 0.05 versus control,
^p < 0.05 versus glutamate

3. The Effects of GK-1, GK-2, GK-3, GK-4, and GK-5 on Heat Shock Proteins in Cultured HT-22 Cells It is well known that NGF can activate the synthesis of the heat shock proteins Hsp32 and Hsp70 (Liu, H., Nowak, R., Cao, W., Bloch, K. D. Nerve growth factor induces anti-apoptotic heme oxygenase-1 in rat pheochromocytoma PC 12 cells. J. Neurochem. 2003, 86, 1553-1563; Pollack, S. J. and Harper, S. J. Small molecule Trk receptor agonists and other neurotrophic factor mimetics: Current drug targets. CNS and Neurological Disorders 2002, 1, 59-80), which display neuroprotective effects.

As shown by Western blot analysis on samples taken 24 hours after the peptides were added to cultures of HT-22 hippocampal neuronal cells, GK-1 at concentrations of 10$^{-8}$ M and 10$^{-5}$ M had no effect on the amount of these proteins. GK-2 at concentrations of 10$^{-8}$ M and 10$^{-5}$ M induced an increase in the levels of Hsp70 and Hsp32 proteins (FIGS. 1.13, 1.14). When GK-1 (10$^{-5}$ M) was added 30 minutes before GK-2, no increase in the amount of Hsp32 and Hsp70 was observed (FIGS. 1.13, 1.14). GK-3 at 10$^{-6}$ M resulted in a small increase of Hsp32 but had no effect on Hsp70 (FIGS. 1.15, 1.16). The application of GK-4 (10$^{-7}$ M) resulted in a significant increase in the synthesis of Hsp70 and had no effect on Hsp32 (FIGS. 1.15, 1.16). Conversely, GK-5 (10$^{-6}$ M) produced an increase in the synthesis of Hsp32 and had no effect on Hsp70 (FIGS. 1.15, 1.16).

Thus, it appears that the protective effects of the claimed compounds are associated with the synthesis of heat shock proteins.

4. Effects of the Peptides on Tyrosine Kinase A Phosphorylation in Cultured HT-22 Cells The results of the Western blot analysis of GK-1, GK-2, GK-3, GK-4, and GK-5 effects on tyrosine kinase A phosphorylation relative to NGF suggest that NGF alone during the first minute of exposure to HT-22 cells did not significantly affect the tyrosine kinase A phosphorylation. At the same time, the dipeptides GK-2, GK-3, GK-4, and GK-5 increased the level of phosphorylated tyrosine kinase A during the very first minute (FIGS. 1.17, 1.18, 1.19). Conversely, the peptide GK-1 decreased the TrkA phosphorylation during the first minute (FIG. 1.19). This is consistent with its antagonist activity versus NGF in the in vitro tests (decreasing the cell viability and inhibiting the differentiation-inducing activity of NGF). The other peptides showed an agonist activity.

During the second minute of exposure, NGF demonstrated an increase in the tyrosine kinase A phosphorylation. And the effect of GK-2 was even more pronounced as compared to the first minute (FIG. 1.20).

Thus, the peptides GK-1 through GK-5 appeared to be ligands of the TrkA receptor.

An analysis of the experimental findings on the in vitro activities of the claimed compounds allows one to make the following conclusions:

Both loop 4 and loop 1 mimetics of NGF and BDNF can influence the survival of neurons. Thus, monomeric loop 4 mimetics were found to decrease the neuronal viability and survival under injurious conditions such as oxidative stress, glutamate excitotoxicity and neurotoxic action of MPTP. Dimeric analogs of this loop, however, displayed a neuroptotective activity. This activity was dependent on the spacer length between the dipeptide segments of the mimetics.

In the case of NGF loop 1 mimetics, both monomeric and dimeric analogs demonstrated a neuroptotective activity. In addition to the neuroptotective activity, these mimetics displayed a differentiation-inducing activity or were capable of modulating the differentiation-inducing activity of NGF. Monomeric loop 4 mimetics having a neurodegenerative action were able to inhibit the differentiation-inducing effects of NGF.

All the neurotrophin mimetics having a neuroptotective activity as well as NGF itself can increase the synthesis of heat shock proteins Hsp32 and/or Hsp70 depending on their structure and also increase the amount of the phosphorylated form of TrkA. This indicates that the claimed compounds are indeed the neurotrophin mimetics acting via tyrosine kinase receptors.

II. Biological Characterization of the Claimed Compounds In Vivo

The claimed compounds having a neuroptotective activity identified in the in vitro experiments were also characterized in animal models of neurodegenerative diseases such as stroke, cerebral ischemia, Parkinson's disease, Alzheimer disease. For the experiments using animal models, the compound was chosen most active with respect to its neuroptotective effects, namely GK-2, a dimeric NGF loop 4 mimetic.

The BDNF mimetics were characterized in a classical animal model used to identify antidepressant activity.

1. Anti-stroke Activity 1.1. GK-2 Activity in a Model of Ischemic Insult Induced by a Unilateral Intravascular Occlusion of a Branch of the Middle Cerebral Artery Male outbred rats with an average weight of 270 g were used for this study.

The experimental animals were distributed into the following groups: SO, sham-operated; IS, rats with ischemic cerebral infarction; and IST, animals treated at 1 h, 24 h and 48 h after ischemia with GK-2 in physiological saline intraperitoneally at 1 mg drug per 1 kg body weight (a total of 3 injections). The other groups were treated at the same time points with an equivalent volume of saline lacking the drug.

Before surgery, the animals were anesthetized with chloral hydrate (300 mg/kg i.p.). Cerebral ischemia was induced in rats by inserting a silicon-coated (Shimamura N, Matchett G, Tsubokawa T, Ohkuma H, Zhang J. Comparison of silicon-coated nylon suture to plain nylon suture in the rat middle cerebral artery occlusion model. J. Neurosci. Meth. 2006, 156(1-2): 161-5) nylon suture as described previously (Zea Longa E, Weinstein P R, Carlson S & Cummins R. (1989) Reversible middle cerebral artery occlusion without craniectomy in rats. Stroke 20: 84-91). The occlusion lasted for 60 min followed by removing the suture to restore the blood flow in the middle cerebral artery basin. During and after the operation the animal's body temperature was maintained at 37.5° C. Sham-operated animals were subjected to the same procedure except for the vessel transection and suture insertion.

The behavioral tests were performed one day prior to surgery which was set as the baseline. Following surgery, the neurological deficit was assessed on days 4 and 7 using the limb-placing test and on day 7 using the cylinder test (Schallert T, Fleming S M, Leasure J L, Tillerson J L, Bland S T. CNS plasticity and assessment of forelimb sensorimotor outcome in unilateral rat models of stroke, cortical ablation, parkinsonism and spinal cord injury. Neuropharmacology, 2000, 39(5):777-87). The animal behavior was analyzed using a double blind protocol. In the cylinder test, the asymmetry in the use of animal's forelimbs is assessed during a spontaneous exploration of the cylinder walls.

To assess the sensorimotor recovery of rat limbs, a modification of the limb-placing test was used (De Ryck M, Van Reempts J, Borgers M, Wauquier A, Janssen P A. Photochemical stroke model: flunarizine prevents sensorimotor deficits after neocortical infarcts in rats. Stroke, 1989, 20(10): 1383-90). The test employs the forelimb and hindlimb responses to tactile and proprioceptive stimuli. The test comprised 7 different tests for the left and right sides of the body. The following scoring system was used to assess abnormalities in the limb function: 2, the rat fulfilled the test completely; 1, the rat fulfilled the test with a delay of more than 2 seconds and/or incompletely; 0, the rat did not respond to limb stimulation.

The brains of the experimental animals were studied by nuclear magnetic resonance tomography (NMRT) at 7 days after surgery. The NMRT experiments were carried out using a Biospec 70/30 instrument (Bruker, Germany) with a magnetic field induction of 7 T and a gradient system of 105 mT/m.

Radio-frequency (RF) signals were transmitted by a linear transmitter having an inner diameter of 72 mm and detected by a surface receiver coil for the rat brain. T2-weighted images were acquired using a spin echo-based pulse pattern, RARE (Rapid Acquisition with Relaxation Enhancement), with the following settings: TE, 6000 ms; TE, 63.9 ms; section thickness, 0.5 mm; field, 4.2×3.1 cv; matrix size, 256×384; resolution, 0.164×0.164 mm/pixel. A total scanning time was 4 min 48 sec. Animals were anesthetized with chloral hydrate and placed in a positioning device equipped with a stereotaxis and thermoregulation system. During the NMR examination the ECG, breathing rate and rectal temperature were measured using an activity control unit, Small Animal Monitoring and Gating System (SA Instruments Inc., USA). NMR images were analyzed using an ImageJ 1.38x software (National Institutes of Health, USA).

Using the image analysis software, the infarct area was measured for each section, including the cortex and subcortical structures. The infarct volume (V) was determined according to the formula:

$$V = d \times \Sigma A_i,$$

where $\Sigma A_i$ is the sum of injured areas in all sections; and d is the section thickness.

On T2-weighted NMR images acquired at 7 days post-ischemia the infarct volume and % brain swelling were determined (Barone F C, Clark R K, Feuerstein G, Lenkinski R E, Sarkar S K. Quantitative comparison of magnetic resonance imaging (MRI) and histological analyses of focal ischemic damage in the rat. Brain Res. Bull. 1991, 26(2): 285-91). Statistical data treatment was performed using a Statistica 6.0 computer software (StatSoft, USA). Normal distribution of a trait in the sample was evaluated using the Shapiro-Wilk W-test. Statistical significance of differences in behavioral tests was evaluated using the Mann-Whitney U-test. The data were expressed as the mean±SE.

Results

One day prior to ischemia (day −1), the baseline neurological status was assessed for all animals using the limb-placing test and the cylinder test. Then GK-2 was administered intraperitoneally in physiological saline at 1 mg drug per 1 kg body weight at 1 h, 24 h and 48 h post-ischemia (a total of 3 injections). The other groups were treated at the same time points with an equivalent volume of physiological saline lacking the drug. On day 4 the animals were evaluated using the limb-placing test, while on days 4 and 7 using both the limb-placing test and the cylinder test as well as by NMRT of the brain. When the rat brain was studied by NMRT at 7 days after ischemia, the lesion area was defined as an increased signal (hyperintensity) on T2-weighted images relative to the intact white matter, due to the development of cytotoxic swelling. The results showed that by that time the swelling of the affected hemisphere was small and represented only 3% relative to the contralateral hemisphere. In the control group, the swelling of the affected hemisphere was observed in 46% of the animals, while in the GK-2 treatment group only in 9% of the animals. The differences in the number of animals with swelling between the IS and IST groups were statistically significant (p=0.019 according to the two-tailed test for differences between two ratios). The mortality rate was 3 animals each in both the control and the treatment group. According to morphometric analysis of NMRT images, the size of the ischemic lesion in control animals treated with saline was 266±20 mm$^3$ (n=12 animals). In the GK-2 treatment group there was a trend towards a decrease in the lesion size, with its volume being 222±16 mm$^3$ (n=12) (FIG. 2.1). On average, the lesion volume was reduced by 16.5%.

The quantitative data indicating a reduced lesion volume in rats injected with GK-2 was fully correlated with the data on sensorimotor limb deficits in these animals obtained in behavioral tests. The limb-placing test showed that the GK-2 treatment in the post-ischemic period resulted in a significant reduction of neurological deficit in ischemic animals. While intact rats scored 14 in the limb-placing test, the ischemic rats scored 3.00±0.38 and 4.46±0.40 on day 4 and day 7 post-ischemia, respectively. The drug administration for 3 times led to a significant improvement of the score to 5.90±0.62 on day 4 and up to 7.67±0.75 on day 7 post-ischemia, respectively. The results of the behavioral tests are shown in FIG. 2.2.

In the cylinder test, the independent use of the contra- and ipsilateral forelimbs prior to ischemia was roughly similar in the IS and IST groups. At 7 days after surgery, the use of the affected limb (contralateral to the lesioned cerebral hemisphere) and the simultaneous use of 2 forelimbs were significantly reduced. The reduction was much less pronounced in rats treated with GK-2 after ischemia (FIG. 2.3).

Thus, GK-2 clearly displays a marked anti-ischemic activity as represented by a reduced volume of the brain lesion and a significant reduction of neurological deficits in animals treated with the drug in the post-ischemic period.

1.2. GK-2 Activity in a Model of Ischemic Insult Induced by a Bilateral Photo-thrombosis of Blood Vessels in the Prefrontal Cortex of Rat Brain Male outbred rats weighing 180-200 g were used.

Experimental stages: surgery for photothrombosis, evaluation of motor activity (before and at 9 days after photothrombosis); PAR conditioning and the retention test at 9 days after photothrombosis; animal sacrifice, excision and fixation of the brain; morphologic examination and ischemic zone volume calculation.

The test substance was administered intraperitoneally at a dose of 1 mg/kg using the following regimen: at 1 h after surgery, at 24 h after the first administration, at 4 days and 6 days after the first administration.

PAR conditioning was performed according to the following protocol: The latency time (LT) was defined as the time between the start of testing and the moment of crossing the hole dividing the light and dark compartments. On day 1 the rat was placed in the light compartment (a 100 W light bulb) and, having explored it for a certain time (LT to learning), crossed into the dark compartment. Thereafter the door leading to this compartment was closed, and the rat was allowed to stay there for 5 min. One hour later the procedure was repeated by taking the rat out of the dark compartment. On the next day this procedure was repeated twice with a 1 h interval. During the second visit by the rat to the dark compartment the door was closed and electric current was passed through the metal bars in the floor (1.3 mA, 50 Hz, 5 sec). The PAR conditioning was considered established when the LT was at least 300 sec. Animals with lower LT values were excluded from the experiments.

A bilateral focal ischemic infarction of the prefrontal cortex of the rat brain (the Fr1 and Fr2 fields according to the atlas of Paxinos and Watson, 1986) was produced by the photoinduced thrombosis method (Watson et al., 1985). Animals were anesthetized with chloral hydrate (300 mg/kg i.p.). The photosensitive dye Bengal red (Sigma Chemical Co.) was injected into the jugular vein (3% solution, 40 mg/kg). The animal's head was clamped in the stereotaxis device, and the periosteum was removed after a longitudinal incision of the skin.

A light guide (the output light beam diameter 3 mm) was placed at a distance of 1 mm from the skull surface using the following coordinates: 2.00 mm rostral of the bregma and 2.00 mm lateral of the sagittal suture. Cold light illumination (a xenon lamp source, 25 V, 250 W) was carried out for 15 min at either side. Sham-operated animals were subjected to the same procedure except for the Bengal red injection. To assess their functional status, the animals were evaluated for their motor activity (MA) in a RODEO-1 automatic unit with an observation time of 5 min. The MA was analyzed before and at 9 days after the photothrombosis of the prefrontal cortex.

For the morphometric measurement of the ischemic area ant the lesion volume, the brains of experimental animals were fixed by immersion in a 2:7:1 formaldehyde-alcohol-acetic acid mixture. The fixed material was transferred into 700 alcohol for 24 h and sectioned in distilled water using a Series 1000 sectioning system vibratome (Technical Product International Inc., USA) to a thickness of 100 µm. Every other serial section was mounted successively on a gelatin-coated slide and stained with 0.2% methylene blue. Then the slides were processed according to a standard histological procedure: dehydrated in alcohol at ascending concentrations, clarified in xylene and embedded in paraffin. The slides were scanned using a slide attachment of an Epson Perfection V100 Photo Scanner. This method enables to produce a file of the brain section image in a delicate blue color, on which an ischemic lesion area is clearly seen as dark-colored on edges and light-colored in the middle. Sometimes the necrotic tissue was disintegrated, therefore the lesion was taken to be represented by the missing tissue area. The ischemic lesion area was calculated using computer software for image analysis in relative units and was correlated to a scanned square with a 10 mm side to give the area in mm$^2$.

The volume of photoinduced thrombosis lesion was determined according to the formula: $V = \Sigma S_n \times d$, where d is the thickness of two sections (200 µm); $S_n$ is the calculated area of ischemic lesion for a serial section in mm$^2$; $\Sigma$ refers to the sum of ischemic lesion volumes for all n sections.

The protection effectiveness rate (PER) was calculated according to the formula: $PER = (V_0 - V_s)/V_0 \times 100\%$, where $V_0$ is the mean volume of lesions in animals treated with saline; $V_s$ is the mean volume of lesions in animals treated with the test substance. This parameter makes it possible to compare the effectiveness of different substances in different models of ischemia.

Results

The experimental animals were distributed into 3 groups:
1. Trained+sham-operated
2. Trained+photothrombosis of the prefrontal cortex
3. Trained+photothrombosis of the prefrontal cortex+GK-2

Prior to surgery, the experimental animals were conditioned for passive avoidance reflex (PAR) up to a latency time (LT) of 300 sec.

TABLE 2.1

The latency time of PAR at 8 days after photothrombosis of the prefrontal cortex (sec)

| Sham-operated | Photothrombosis + saline | Photothrombosis + GK-2 |
|---|---|---|
| 300 | 20 | 300 |
| 300 | 30 | 300 |
| 300 | 103 | 300 |
| 300 | 38 | 300 |
| 300 | 105 | 300 |
|  |  | 300 |
|  |  | 300 |
|  |  | 300 |
|  |  | 300 |
| 300    n = 5 | 59.2    n = 5 | 300    n = 9 |

After the photothrombosis, the latency time to crossing into the dark compartment was reduced from 300 sec to 59.2 sec. In GK-2 treated rats the conditioned reflex was fully restored, i.e. the latency time was at least 300 sec (Table 2.1).

Thus, the data obtained in the pathophysiological evaluation clearly indicate a marked anti-amnestic effect of the drug GK-2 under conditions of the local brain ischemia.

The lesion volume in both left and right hemispheres as well as the lesion size per rat and the mean lesion volume were reduced in the treated animals (FIG. 2.4).

In addition to anti-amnestic effect demonstrated by a 100% retention of the PAR established prior to the photoinduced thrombosis of the prefrontal cortex, GK-2 also possesses a significant neuroprotective activity, i.e. the protection effectiveness rate (PER) was calculated to be 61%.

1.3. GK-2 Activity in a Model of Hemorrhagic Stroke

Methods

The experiments were carried out on male white outbred rats weighing 220-250 g. The animals were housed in a standard animal facility and had free access to water and food. The local cerebral hemorrhage (post-traumatic intracerebral hemorrhage) as a hemorrhagic stroke (HS) model was produced by the method of Makarenko (Makarenko A. N. et al., Zh. V. N. D. 2002, 52(6), 765-768).

To produce the stroke, rats were anesthetized with chloral hydrate (400 mg/kg i.m.) followed by craniotomy. The cerebral tissue in the region of internal capsule was destroyed followed (in 2-3 min) by the injection of blood (0.02-0.03 ml) taken from under the animal's tongue. In this way a local autohemorrhagic bilateral stroke in the region of internal capsule was modeled without a significant damage to the overlying brain structures and the neocortex.

The neurological deficits, changes in the coordination of movements, muscle tone, orientation and exploratory behavior of the rats were recorded at 24 h after surgery.

The rats were monitored for 14 days after surgery. Animal's physical condition and behavioral features were recorded at 1, 3, 7 and 14 days.

The animals were distributed into 3 groups. Group 1 comprised sham-operated (SO) rats with craniotomy alone, group 2 comprised animals with HS, and group 3 comprised rats with HS treated with GK-2 (1 mg/kg at 3 h after surgery and every 48 hours thereafter for a total of 6 administrations). Group 1 and group 2 animals were treated with physiological saline in an equivalent volume.

Changes in animals' physical condition and behavior were evaluated by conventional methods. The neurological status was assessed by scoring neurological deficits according to MacGrow's stroke scoring system as modified by I. V. Gannushkina; by the muscle tone and coordination of movements monitoring methods; cognitive function was assessed by the passive avoidance conditioned reflex (PAR); and orientation and exploratory behavior by using the open field test. Also the drug's effect on the survival of rats was monitored.

The statistical data treatment was carried out by calculating the mean value and the confidence interval for p<0.05. The statistical significance was assessed according to Student's t-test and the $\chi^2$-test.

Results

GK-2 completely prevented the loss of animals when administered at a dose of 1 mg/kg immediately after surgery and every other day thereafter for 14 days, while the mortality rate in the control group was 40% (Table 2.2). The number of animals with impaired coordination of movements was two-fold lower in the GK-2 treatment group than in the HS group and was similar to that in the sham-operated group (Table 2.3). The number of animals with weakened muscle tone in the GK-2 treatment group was not significantly different from that in the sham-operated group and on average was two-fold lower than in the HS group (Table 2.4).

HS produces an impairment of the burrowing reflex which is not observed in animals treated with GK-2 (Table 2.5). Passive avoidance conditioning was also impaired in the HS group: 100% rats entered the dark compartment oblivious of the electric current shock. In the case of rats treated with GK-2, at 1 through 7 days the number of animals that entered the dark compartment was not different from that in the sham-operated group. And the latency to the first visit in the treatment group was not different from that in the sham-operated group. On day 3, however, there was a significant difference in latency between the treatment group and the HS group (Table 2.6). Thus, GK-2 can restore the learning ability impaired by HS.

GK-2 reduced the extent of neurological deficits to the level of the sham-operated rats on days 1, 3, 7 as shown by slowness of movements and limb weakness, and on day 3 as shown by the paresis of 1 to 4 limbs (Table 2.7).

At 1 day and 7 days after surgery GK-2 restored the general indices of motor activity and exploratory behavior impaired by HS to the level observed in the sham-operated rats (Table 2.8).

As shown by the cruciform maze test, HS induced an increased anxiety in rats which was significantly relieved by GK-2 starting on day 1 through the whole length of the observation period (Table 2.9).

Thus, GK-2 possesses a marked anti-stroke activity in rats with hemorrhagic stroke.

TABLE 2.2

The effect of GK-2 on animal survival following HS

| Animal group | Number of rats lost within 14 days after HS | | | | | | | | | |
|---|---|---|---|---|---|---|---|---|---|---|
| | Total loss | | Day 1 | | Day 3 | | Day 7 | | Day 14 | |
| | abs. | % | abs. | % | abs. | % | abs. | % | abs. | % |
| Sham-operated | 0/10 | 0 | 0/10 | 0 | 0/10 | 0 | 0/10 | 0 | 0/10 | 0 |
| Stroke | 4/10* | 40 | 2/10 | 20 | 0/8 | 0 | 1/8 | 12.5 | 1/7 | 14.3 |
| Stroke + GK-2 (1 mg/kg) | 0/10# | 0 | 0/10 | 0 | 0/10 | 0 | 0/10 | 0 | 0/10 | 0 |

*$p \leq 0.05$ versus sham-operated,
$p \leq 0.05$ versus stroke (exact Fisher test)

TABLE 2.3

The effect of GK-2 on the coordination of movements in the rotarod test following HS

| Animal group | Number of rats missing the rotating rod (3 rpm) during 2 min | | | | | | | |
|---|---|---|---|---|---|---|---|---|
| | Day 1 | | Day 3 | | Day 7 | | Day 14 | |
| | abs. | % | abs. | % | abs. | % | abs. | % |
| Sham-operated | 3/10 | 30 | 2/10 | 20 | 0/10 | 0 | 0/10 | 0 |
| Stroke | 6/8 | 75 | 5/8 | 62.5 | 3/7 | 43 | 1/6 | 17 |
| Stroke + GK-2 (1 mg/kg) | 4/10 | 40 | 3/10 | 30 | 2/10 | 20 | 0/10 | 0 |

TABLE 2.4

The effect of GK-2 on the muscle tone in the horizontal bar test following HS

| Animal group | Number of rats failing to mount the horizontal bar | | | | | | | |
|---|---|---|---|---|---|---|---|---|
| | Day 1 | | Day 3 | | Day 7 | | Day 14 | |
| | abs. | % | abs. | % | abs. | % | abs. | % |
| Sham-operated | 3/10 | 30 | 2/10 | 20 | 0/10 | 0 | 0/10 | 0 |
| Stroke | 6/8 | 75 | 3/8 | 37.5 | 3/7 | 43 | 1/6 | 17 |
| Stroke + GK-2 (1 mg/kg) | 4/10 | 40 | 2/10 | 20 | 1/10 | 10 | 0/10 | 0 |

TABLE 2.5

The effect of GK-2 on the learning ability

| Animal group | Latency to entering the dark compartment (burrowing reflex) (sec) |
|---|---|
| Sham-operated | 13.3 ± 2.10 |
| Stroke | 40.2 ± 13.2* |
| Stroke + GK-2 (1 mg/kg) | 27.9 ± 10.4 |

*$p < 0.05$ versus sham-operated (Student's t-test)

TABLE 2.6

The effect of GK-2 on the PAR conditioning in rats with post-traumatic intracerebral hemorrhage

| Animal group | PAR retention after conditioning | |
|---|---|---|
| | Latency to entering the dark compartment (sec) | Number of rats entering the dark compartment (%) |
| Day 1 | | |
| Sham-operated | 95.0 ± 23.9 | 60 |
| Stroke | 24.5 ± 6.10 | 100 |
| Stroke + GK-2 (1 mg/kg) | 85.5 ± 25.9 | 60 |
| Day 3 | | |
| Sham-operated | 74.0 ± 24.5 | 70 |
| Stroke | 18.3 ± 3.30 | 100 |
| Stroke + GK-2 (1 mg/kg) | 88.0 ± 25.8# | 60 |
| Day 7 | | |
| Sham-operated | 97.2 ± 27.6 | 50 |
| Stroke | 17.6 ± 6.30 | 100 |
| Stroke + GK-2 (1 mg/kg) | 45.5 ± 22.5 | 80 |
| Day 14 | | |
| Sham-operated | 93.5 ± 8.0 | 60 |
| Stroke | 8.0 ± 2.0* | 100 |
| Stroke + GK-2 (1 mg/kg) | 45.0 ± 16.4 | 90 |

*$p < 0.05$ versus sham-operated,
$p < 0.05$ versus stroke (Student's t-test)

TABLE 2.7

The effect of GK-2 on neurological deficits in rats following HS using the MacGrow scale Relative number of animals with neurological deficits (%)
Animal group

| Neurological symptoms | Day 1 SO | Day 1 HS | Day 1 GK-2 (1 mg/kg) | Day 3 SO | Day 3 HS | Day 3 GK-2 (1 mg/kg) | Day 7 SO | Day 7 HS | Day 7 GK-2 (1 mg/kg) | Day 14 SO | Day 14 HS | Day 14 GK-2 (1 mg/kg) |
|---|---|---|---|---|---|---|---|---|---|---|---|---|
| Floppiness & slowness of movements | 40 | 100 | 40 | 30 | 100 | 30 | 0 | 43 | 0 | 0 | 0 | 0 |
| Limb weakness | 30 | 75 | 30 | 30 | 75 | 30 | 0 | 43 | 0 | 0 | 0 | 0 |
| Ring movements | 0 | 50 | 20 | 0 | 37.5 | 10 | 0 | 0 | 0 | 0 | 0 | 0 |
| Paresis of 1 to 4 limbs | 0 | 37.5 | 20 | 0 | 25 | 0 | 0 | 0 | 0 | 0 | 0 | 0 |
| Paralysis of 1 to 4 limbs | 0 | 0 | 0 | 0 | 0 | 0 | 0 | 0 | 0 | 0 | 0 | 0 |

TABLE 2.8

The effect of GK-2 on exploratory behavior and motor activity of rats in the open field test following HS

| Animal group | Horizontal motor activity | Vertical motor activity | Exploration of openings | Cumulative index |
|---|---|---|---|---|
| Day 1 | | | | |
| Sham-operated | 14.1 ± 2.1 | 5.0 ± 1.1 | 10.3 ± 1.4 | 30.3 ± 4.2 |
| Stroke | 4.4 ± 1.01* | 1.25 ± 0.9* | 1.9 ± 0.8* | 7.5 ± 1.9* |
| Stroke + GK-2 (1 mg/kg) | 9.9 ± 2.1# | 3.7 ± 0.9 | 3.6 ± 0.7 | 17.2 ± 3.5# |
| Day 3 | | | | |
| Sham-operated | 9.3 ± 1.6 | 4.6 ± 1.1 | 4.0 ± 1.0 | 17.9 ± 2.7 |
| Stroke | 3.0 ± 1.0* | 1.1 ± 0.5* | 3.1 ± 0.5 | 7.2 ± 1.6* |
| Stroke + GK-2 (1 mg/kg) | 5.6 ± 1.4 | 2.4 ± 0.6 | 3.7 ± 0.9 | 11.7 ± 2.4 |
| Day 7 | | | | |
| Sham-operated | 8.6 ± 1.5 | 4.1 ± 0.8 | 3.7 ± 0.7 | 16.4 ± 12.8 |
| Stroke | 3.7 ± 1.1* | 1.0 ± 0.7* | 2.9 ± 0.6 | 7.6 ± 1.5* |
| Stroke + GK-2 (1 mg/kg) | 8.1 ± 1.6 | 4.4 ± 0.7# | 4.3 ± 0.9 | 16.8 ± 2.7# |
| Day 14 | | | | |
| Sham-operated | 9.1 ± 1.7 | 5.1 ± 1.1 | 5.0 ± 0.5 | 19.2 ± 3.0 |
| Stroke | 1.8 ± 0.5* | 1.0 ± 0.4* | 2.8 ± 0.7* | 5.7 ± 1.4* |
| Stroke + GK-2 (1 mg/kg) | 7.5 ± 1.7# | 2.8 ± 0.9 | 3.2 ± 0.9 | 13.5 ± 2.9 |

*$p < 0.05$ versus sham-operated,
$p < 0.05$ versus stroke (Student's t-test)

TABLE 2.9

The effect of GK-2 on animal behavior in the cruciform maze test following HS

| Animal group | Latency to entering an arm (sec) | Length of time (sec) spent in: the middle | Length of time (sec) spent in: open arms | Length of time (sec) spent in: closed arms | Number of crossings into: the middle | Number of crossings into: open arms | Number of crossings into: closed arms |
|---|---|---|---|---|---|---|---|
| Day 1 | | | | | | | |
| Sham-operated | 6.1 ± 1.1 | 46.8 ± 20.8 | 11.6 ± 7.7 | 241.6 ± 27.8 | 1.9 ± 0.5 | 0.9 ± 0.3 | 2.4 ± 0.5 |
| Stroke | 62.8 ± 34.7 | 95.3 ± 43.8 | 0 | 204.8 ± 43.8 | 0.25 ± 0.2* | 0* | 1.1 ± 0.1* |
| Stroke + GK-2 (1 mg/kg) | 4.9 ± 1.05 | 27.5 ± 7.4 | 51.3 ± 27.9 | 221.2 ± 28.5 | 1.5 ± 0.4# | 1.6 ± 0.4# | 1.9 ± 0.4 |
| Day 3 | | | | | | | |
| Sham-operated | 5.1 ± 1.7 | 18.6 ± 11.4 | 6.2 ± 2.7 | 275.2 ± 10.9 | 0.6 ± 0.3 | 0.6 ± 0.2 | 1.4 ± 0.3 |
| Stroke | 164.4 ± 51.4* | 165.0 ± 51.1* | 1.3 ± 1.2 | 133.7 ± 50.6* | 0.12 ± 0.12 | 0.12 ± 0.12 | 0.5 ± 0.2* |
| Stroke + GK-2 (1 mg/kg) | 7.1 ± 1.9# | 15.1 ± 4.9# | 10.3 ± 4.4 | 274.6 ± 5.7# | 0.5 ± 0.2 | 0.8 ± 0.2# | 1.2 ± 0.1# |
| Day 7 | | | | | | | |
| Sham-operated | 3.0 ± 0.6 | 8.3 ± 2.9 | 13.3 ± 3.9 | 278.4 ± 4.6 | 0.7 ± 0.2 | 1.4 ± 0.2 | 1.4 ± 0.2 |
| Stroke | 67.4 ± 41.8 | 67.4 ± 41.8 | 8.6 ± 7.0 | 238.3 ± 40.4 | 0* | 0.4 ± 0.2* | 1.0 ± 0.2 |
| Stroke + GK-2 (1 mg/kg) | 2.5 ± 0.3 | 8.0 ± 2.2 | 9.2 ± 1.9 | 283.0 ± 2.9 | 0.8 ± 0.4 | 1.1 ± 0.2 | 1.5 ± 0.2 |

TABLE 2.9-continued

The effect of GK-2 on animal behavior in the cruciform maze test following HS

| Animal group | Latency to entering an arm (sec) | Length of time (sec) spent in: | | | Number of crossings into: | | |
|---|---|---|---|---|---|---|---|
| | | the middle | open arms | closed arms | the middle | open arms | closed arms |
| Day 14 | | | | | | | |
| Sham-operated | 3.1 ± 0.8 | 18.1 ± 12.5 | 29.7 ± 15.0 | 252.2 ± 28.1 | 0.7 ± 0.15 | 1.1 ± 0.2 | 1.3 ± 0.2 |
| Stroke | 54.3 ± 49.2 | 57.7 ± 48.6 | 0.8 ± 0.8 | 241.5 ± 48.4 | 0.2 ± 0.2* | 0.2 ± 0.2* | 0.8 ± 0.2 |
| Stroke + GK-2 (1 mg/kg) | 2.6 ± 0.4 | 16.4 ± 8.5 | 8.8 ± 2.3# | 274.8 ± 9.9 | 1.4 ± 0.3 | 1.1 ± 0.3# | 1.6 ± 0.4 |

*p < 0.05 versus sham-operated,
p < 0.05 versus stroke (Student's t-test)

The results obtained show that the test compound GK-2 can be useful in the treatment of both ischemic and hemorrhagic insults. Thus it would make it possible to undertake the treatment of stroke patients even before the differential diagnostics, i.e. at the most important first stages of the disease.

2. Anti-ischemic Activity

Ageing and progressive neurodegenerative and neurovascular diseases are accompanied by a reduced cerebral blood flow. Insufficient blood supply to the brain tissues may result in the neuronal death and the consequent neurological deficits and impairment of various cognitive functions. Thus, for instance, it was shown that some cognitive functions are impaired in patients with diseases of the carotid artery (Bakker F. C., Klijn C. J., Jennekens-Schinkel A., Kapelle L. J. Cognitive disorders in patients with occlusive disease of the carotid artery: a systematic review of the literature. Neurology, 2000, 247(9), 669-676). A bilateral ligation of the rat carotid artery was used as a model for permanent cerebral hypoxia and related neuronal death and cognitive deficits (Bennett S. A. L., Tenniswood M., Chen Jia-Hua, Davidson C. M., Keyes M. T., Fortin T., Pappas B. A. Chronic cerebral hypoperfusion elicits neuronal apoptosis and behavioral impairment. NeuroReport, 1998, 9, 161-166). Therefore, behavioral tests were chosen that can reveal cognitive pathology induced by ischemia (the open field test and the object recognition test) in accordance with the suggestions in Sarti et al., 2002 (Sarti C., Pantoni L., Bartolini L., Inzitari D. Cognitive impairment and chronic cerebral hypoperfusion: what can be learned from experimental models. J. Neurol. Sci. 2002, 203-204, 263-266).

2.1. GK-2 Activity in a Model of Ischemia Induced by a Bilateral Ligation of the Carotid Artery The experiments were conducted on male outbred rats weighing 350-420 g. The test compound was administered intraperitoneally at a dose of 1 mg/kg. On day 1 the animals were given the first injection of the test compound. 24 hours later (day 2) they underwent surgery for a bilateral ligation of the carotid artery. Following another 24 h (day 3) the animals were given the second injection of the test compound. 96 hours later (day 7) they were given the third injection of the test compound. Following another 24 h (day 8) the animals were tested in an open field test (Jackson H. F., Broadhurst P. L. The effects of parachlorophenylalanine and stimulus intensity on open-field test measures in rats. Neuropharmacology, 1982, 21, 1279-1282). On the next day (day 9) they were allowed to explore new objects (a modification of the test described in Ennaceur A., Delacour J. A new one-trial test for neurobiological studies of memory in rats. 1: Behavioral data. Behavioral Brain Research, 1988, 31, 47-59). On day 11 the animals were given the fourth injection of the test compound. The animals were sacrificed by decapitation 120 hours after the last injection of the test compound (day 16).

The rats were distributed into 3 groups (n≥8 for each group) at random. Group 1 (sham-operated) comprised animals that were anesthetized followed by a sham operation and subsequently received 4 injections of physiological saline according to the experimental set-up; Group 2 (ligation) comprised animals that were anesthetized followed by surgery for a bilateral ligation of the carotid artery and subsequently received 4 injections of saline according to the experimental set-up; Group 3 (ligation+test compound) comprised animals that were anesthetized followed by surgery for a bilateral ligation of the carotid artery and subsequently received 4 injections of the test compound according to the experimental set-up.

Following decapitation, the animal's brain was quickly removed and placed in an ice-cold physiological saline (0.9% NaCl) for 2 min. Then the brain was taken out of the saline and placed on ice covered with a filter paper for the isolation of various regions. The hippocampus, striatum, and cortex were excised and transferred into an ice-cold serum. For the cortex and the hippocampus, the volume of serum was 4 ml, for the striatum, 2 ml. Thereafter the brain regions in their respective sera were passed through a 40 μm nylon filter (Millipore) to produce a homogeneous mass. The resulting cell suspension was centrifuged at room temperature for 5 min in a Thermo Jouan centrifuge at 1500 rpm. The supernatant was poured off, and the cells were resuspended in 10 ml DMEM containing 10% FBS. The cells were then counted in a Goryaev chamber.

For the viability assay $2 \times 10^6$ cells/ml were used. Each well of a 96-well plate was filled with a 100 μl sample and 10 μl MTT was added. The plate was incubated for 30 min in a thermostat set at 37° C. until a blue-violet color developed. To dissolve the formazan crystals, 100 μl DMSO was added to each well. The absorbance at 600 nm was measured in a Multiscan spectrophotometer (Thermo). Each sample was measured against its own blank lacking MTT. The statistical treatment of experimental results was carried out using a Statistica 6.0 software package according to the Mann-Whitney U-test, the exact Fisher test for independent samples, and Wilcoxon paired test for dependent samples. The data were expressed as the median value±interquartile interval (FIGS. 2.5 through 2.9).

Permanent cerebral ischemia/hypoxia induced by a bilateral ligation of the carotid artery affected the exploratory behavior of rats in the open field test. The components of the exploratory behavior most sensitive to this intervention were the horizontal motor activity and the vertical motor activity.

FIG. 2.5 shows that the ligation led to a reduced horizontal motor activity in the open field test. GK-2 restored it to the level found in the sham-operated rats. The ligation also led to a reduced vertical motor activity in the open field test, and GK-2 restored it to the level found in the sham-operated rats.

In the object exploration test, the ligation resulted in a reduced total object smelling time (FIG. 2.7). The lower level of this index in the ligation group was due to a reduction in the object exploration during the first minute of testing (FIG. 2.8). FIGS. 2.7 and 2.8 also show that the ligation group treated with GK-2 was not different from the sham-operated rats, i.e. GK-2 prevented the decline in these measures induced by the ligation. Thus, GK-2 was able to improve the episodic memory in rats and their ability to perceive novelty.

The experimental results demonstrate that the viability of the hippocampal and striatal cells was not different between the sham-operated group and the ligation group. At the same time, the ligation was found to produce a greater adverse effect on the cortical cells (FIG. 2.9). However, the viability of the cortical cells in the ligation group was enhanced by the GK-2 treatment (FIG. 2.9).

In summary, the results obtained indicate that GK-2 possesses anti-ischemic properties and that it can be useful in hypoxic conditions.

3. Anti-parkinsonian Activity of GK-2

At present, one of the most common neurodegenerative diseases is Parkinson's disease which is underlied by the attenuation of dopaminergic neurons function in the brain (Hirsch E C, Herrero M T. Neurochemical correlates of parkinsonism. Role of dopaminergic lesions. Adv. Neurol. 1997, 74, 119-126). The disease not only develops spontaneously in old age but also can be provoked by neuroleptics such as haloperidol (Hardie R. J., Lees A. J. Neuroleptic-induced Parkinson's syndrome: clinical features and results of treatment with levodopa. Journal of Neurology, Neurosurgery and Psychiatry, 1988, 51, 850-854).

There are two approaches to in vivo modeling the inhibition of DA neurotransmission. The first approach involves tests that model the catalepsy and other extrapyramidal disorders induced by dopaminergic substances. Catalepsy is generally elicited by treatment with various neuroleptics, mostly haloperidol (Sanberg P. R. Haloperidol-induced catalepsy is mediated by postsynaptic dopamine receptors. Nature, 1980, 284(5755), 472-473). The second approach involves a selective damage to DA neurons that can be induced by neurotoxins such as MPTP (Snyder S., D'Amato R. J. MPTP: a neurotoxin relevant to the pathophysiology of Parkinson's disease. The 1985 George C. Cotzias lecture. Neurology, 1986, 36(2), 250-258).

3.1. Prevention of the Haloperidol-induced Catalepsy in the Rat

The experiments were conducted on white male outbred rats weighing 250-280 g. Haloperidol (1.0 mg/kg i.p.), a D1/D2 dopamine receptor blocker, was used to induce catalepsy. The intensity of catalepsy was assessed by measuring the time during which the animal maintained an assumed posture. The measurements were performed 60 minutes after the haloperidol injection. The test compound was administered intraperitoneally at selected doses (0.01, 0.1, 1.0 and 5.0 mg/kg) 24 hours prior to haloperidol. Control animals were treated with an equivalent volume of distilled water. Statistical data treatment was carried out using the exact Fisher test. The results are shown in Table 2.10 below.

TABLE 2.10

The effect of GK-2 on the intensity of haloperidol-induced catalepsy

| GK-2 dose (mg/kg) | Number of rats (n) | Intensity of catalepsy (% of control) |
|---|---|---|
| Control (phys. saline) | 15 | 100 |
| 0.01 | 10 | 14* |
| 0.1 | 10 | 98 |
| 1.0 | 10 | 25* |
| 5.0 | 10 | 13* |

*$p < 0.05$ versus control

In this study GK-2 was found to attenuate haloperidol-induced catalepsy significantly at doses of 0.01, 1.0 and 5.0 mg/kg. These results suggested that the test compound possesses dopamine-positive (antiparkinsonian) properties.

3.2. Prevention of the MPTP-induced Akinesia in the Mouse

The test compound was administered intraperitoneally to male C57B1/6 mice weighing 22-25 g at a preselected dose of 1.0 mg/kg at 24 hours prior to the MPTP injection (30 mg/kg i.p.). The animals were placed in the open-field device 60 min after the MPTP injection. Animal's horizontal and vertical motor activities were monitored for 2 minutes. Passive control group was represented by animals treated with distilled water instead of MPTP. Active control group was represented by animals treated with distilled water instead of GK-2 followed by MPTP. The treatment group was treated with GK-2 followed by MPTP. Statistical data treatment was carried out using the Mann-Whitney U-test. The results are shown in Table 2.11 below.

TABLE 2.11

The effect of GK-2 pretreatment on the MPTP-induced akinesia in mice in the open-field test

| Experimental group | Number of sectors crossed (% of passive control) |
|---|---|
| Passive control (n = 10) | 100 |
| Active control (n = 10) | 8* |
| Treatment group (n = 10) | 38*+ |

*$p < 0.05$ versus passive control,
+$p < 0.05$ versus active control

The experiments showed that the test compound could effectively prevent the MPTP-induced behavioral abnormalities under pretreatment conditions leading to the suggestion of potential antiparkinsonian activity for the test compound.

3.3. Enhancement of the Apomorphine-induced Stereotypy in the Rat

Psychostimulants (in particular apomorphine) can induce stereotyped behavior in rodents (Lal S., Sourkes T. L. Ontogeny of stereotyped behaviour induced by apomorphine and amphetamine in the rat. Arch. Int. Parmacodyn. Ther. 1973, 202 (1), 171-182). A potentiation of the apomorphine effects indicates that the test compound can elicit a stimulatory influence on DA neurotransmission (Khabriev R. U. A Manual on Experimental (Preclinical) Studies of New Pharmacological Substances. Moscow, 2000, p. 147-152).

The experiments were carried out on male outbred rats weighing 250-300 g. The test compound was administered intraperitoneally at a preselected dose of 1.0 mg/kg at 24 hours prior to the apomorphine injection or concurrent with apomorphine. The control group was treated with distilled water according to the same regimen. Apomorphine was dissolved at 1 mg/ml in distilled water supplemented with 0.01% ascorbic acid and was administered subcutaneously in the neck area. Immediately after the apomorphine injection, the animals were placed in the observation chambers and the observation started 5 minutes later. The observation was carried out according to guidance set out in the manual (Khabriev R. U. A Manual on Experimental (Preclinical) Studies of New Pharmacological Substances. Moscow, 2000, p. 149). Oral stereotypy (smelling, licking, biting) was recorded using the following scoring system: 1, isolated stereotyped movements; 2, brief (episodic) stereotypy; 3, continuous stereotypy. To record a continuous, deep and very intensive stereotypy, an additional score of 4 was introduced to the existing scale (deep stereotypy was characterized in that the animals were unresponsive to external stimuli). Stereotypy was recorded once for 5 min within a period of 60 min. At the end of an experiment the cumulative score for each animal was calculated for the entire testing period. Differences between experimental groups were assessed according to the Mann-Whitney U-test. The data were expressed as the median value±interquartile interval (FIG. 2.10).

The experiments showed that the test compound enhanced the intensity of apomorphine-induced oral stereotypy under pretreatment conditions thus confirming its dopamine-positive properties.

4. The Effects of GK-2 in Experimental Models of Alzheimer's Disease

Besides Parkinson's disease, neurodegenerative diseases include Alzheimer's disease (AD) as well. According to the 'cholinergic hypothesis', the progressive development of cognitive deficit in AD patients is due to reduced functional parameters of the cholinergic system and the degeneration of cholinergic neurons in the forebrain nucleus basalis (Bartus R. T., Dean R. L., Pontecorvo M. J., Flicker C. The cholinergic hypothesis: a historical overview, current perspective, and future directions. Ann. New York Acad. Sci. 1985, 44, 332-358). Basic animal models that simulate the behavioral and cholinergic deficits of AD in the absence of its pathomorphological pattern include the hippocampal deafferentation model (Krugel U., Bigl V., Eschrich K., Bigl M. Deafferentation of the septo-hippocampal pathway in rats as a model of the metabolic events in Alzheimer's disease. Int. J. Devl. Neuroscience, 2001, 19, 263-277). This model was used to assess the efficacy of the compound GK-2. The cholinergic deficits were also simulated using the scopolamine-induced amnesia model.

4.1. Prevention of the Exploratory Behavior Impairment in the Rat Induced by the Transection of the Septo-hippocampal Pathway (Fimbria-Fornix)

The experiments were carried out on male Wistar rats weighing 280-400 g. Animals were anesthetized and scalped followed by being placed in the stereotaxis device. A skewed incision was made in the skull 1 mm wide: the start point for incision was at the level of bregma (AP=0.0) and 2 mm lateral of it (L=±2); the end point for incision was 2 mm caudal of bregma and 1 mm lateral of it (AP=2.0, L=±1). Following the sawing of the skull bone, the dura mater was incised carefully in the sawcut area. A sterile curved needle was inserted into the incision to a depth of 6.2 mm from the bone surface (DV=−6.2). By the simultaneous use of two screws in the stereotaxis device, the needle was moved slowly almost to the end point of the skewed incision. Then the needle was lifted slowly from the incision. The procedure was repeated twice on each hemisphere. Sham operation was similar to the transection procedure except that the needle was inserted to a depth of 3 mm from the bone surface (DV=−3.0). The first injection of the test compound (1 mg/kg i.p.) in the treatment group or of distilled water in the control group was made 2 hours after the transection. Further injections were made every 48 hours. In the course of the experiment each animal received 7 injections of the test compound.

To detect behavioral abnormalities induced by the transection of the septo-hippocampal pathway, the open-field test was used. The choice of this test was based on the following studies: 1) Lamprea M. R., Cardenas F. P., Silveira R., Walsh T. J., Morato S. Effects of septal cholinergic lesion on rat exploratory behavior in an open-field. Braz. J. Med. Biol. Res. 2003, 36(2), 233-238; 2) Cassel J. S., Kelche C., Peterson G. M., Ballough G. P., Goepp I., Will B. Graft-induced behavioral recovery from subcallosal septohippocampal damage in rats depends on maturity stage of donor tissue. Neuroscience, 1991, 45(3), 571-586. Animals were tested in the open-field device 48 hours after the last injection of the test compound (at 14 days after surgery). Differences between experimental groups were assessed according to the Wilcoxon paired test. The experimental results are shown in Table 2.12. The data are expressed as the median values for the respective samples.

TABLE 2.12

Effects of the chronic GK-2 treatment on the horizontal motor activity of rats in the open-field test

| Group | 1st minute | 2nd minute | 3rd minute | 4th minute |
|---|---|---|---|---|
| Control | 15 | 11.5 | 11* | 2* |
| Sham-operated | 21 | 14 | 9.5* | 9* |
| Transection | 11.5 | 12 | 19 | 11.5 |
| Transection + GK-2 | 12.5 | 11.5 | 15.5 | 6.5* |

*$p < 0.05$ versus first minute

The table shows that habituation to the open-field device conditions was impaired in the transection group as shown by an almost unchanged level of horizontal motor activity during the entire testing period. Similar results were obtained in the studies cited above. In the transection+GK-2 treatment group a restoration of the habituation ability was observed. These results allow one to suggest that the test compound possesses a neuroprotective activity towards the cholinergic system.

In order to confirm this suggestion, we performed an additional study using scopolamine as a pathologic agent which is an antagonist of muscarinic acetylcholine receptors.

4.2. Prevention of the Scopolamine-induced Working Memory Impairment in the Rat

Male Wistar rats weighing 190-220 g were used for this experiment. The test compound was administered intraperitoneally at a dose of 1.0 mg/kg at 24 hours prior to the scopolamine injection (1.0 mg/kg s.c.). The control group was treated with distilled water according to the same regimen. Scopolamine was injected 60 min before placing the animals in a T-shaped maze. Following a further 120 min the animals were subjected to testing in accordance with the original protocol (Deacon R. M. J., Rawlins J. N. P. T-maze alternation in the rodent. Nature Protocols, 2006, 1(1), 7-12).

Differences between experimental groups were assessed according to the exact Fisher test. The experimental results are shown in FIG. 2.11.

The experiment demonstrated that the test compound could prevent the scopolamine-induced working memory impairments under pretreatment conditions.

Thus, a comprehensive analysis of the available data on the basis of conventional methods of pharmacological assessment allows one to conclude that the biological effects spectrum of GK-2, a low molecular weight dimeric NGF (nerve growth factor) mimetic, includes anti-stroke, anti-parkinsonian, anti-ischemic, anti-amnestic and neuroprotective activities.

5. Antidepressant Activity 5.1. Effects of BDNF Mimetics in the Behavioral Despair Test According to Porsolt In order to detect a potential antidepressant activity of the peptide BDNF mimetics, the behavioral despair test was used in the original version (Porsolt R. D., Anton G., Blavet N., Jalfre M. Behavioral despair in rats: a new model sensitive to antidepressants. European Journal of Pharmacology, 1978, 47, 379-391).

For these experiments, male Balb/c mice weighing 20-22 g were used. On day 1, the animals were placed in a narrow vessel filled with water at 22° C. for 10 min. 60 min later a test compound was administered intraperitoneally (GSB-106 at 1 mg/kg, GBK-108 and GBK-201 at 0.01, 0.1, 1.0, 10.0 mg/kg). 24 hours later the animals were placed again in the same conditions to record the retention time of the characteristic immobile posture (abandoning any active defensive and exploratory behavior) for a 5 min test period. Imipramine was administered 60 min prior to the 5 min test period (on day 2). The control groups were treated with distilled water. Each experimental group comprised at least 6 mice. Differences between experimental groups were assessed according to the Mann-Whitney U-test and the exact Fisher test. The data were expressed as the median value±interquartile interval.

The experimental results are shown in FIGS. 2.12 and 2.13.

FIG. 2.13 shows that imipramine and GSB-106 displayed antidepressant properties by reducing the immobility time in the test. Conversely, GBK-201 (at 0.01 and 0.1 mg/kg i.p.) and GBK-108 (at 10 mg/kg i.p.) increased the immobility time in the test. An increased immobility time in the behavioral despair test according to Porsolt is inherent to substances possessing neuroleptic activities.

Thus, the dimeric BDNF mimetics having a neuroprotective activity exhibited antidepressant activity in the Porsolt test. The monomeric BDNF mimetics that reduce the viability of neurons exhibited prodepressant activity.

The invention claimed is:

1. A compound

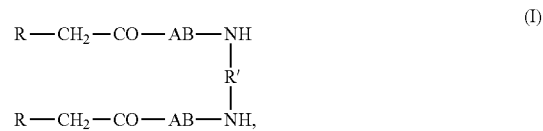

wherein
R is HO(O)C—$CH_2$—;
A is Ser; B is Lys; and
R' is —$(CH_2)_6$—.

2. A compound of formula (1)

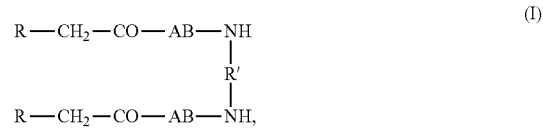

where AB is a dipeptide fragment of a neurotrophic factor, and wherein
AB is SerLys, R is HO(O)C—$CH_2$—; and
R' is a bivalent radical —$(CH_2)_m$—, where m>1.

3. The compound according to claim 2 which is Bis(monosuccinyl-L-Seryl-L-Lysine)hexamethylenediamide.

4. The compound according to claim 2 where m is 6.

* * * * *